Figure 4:
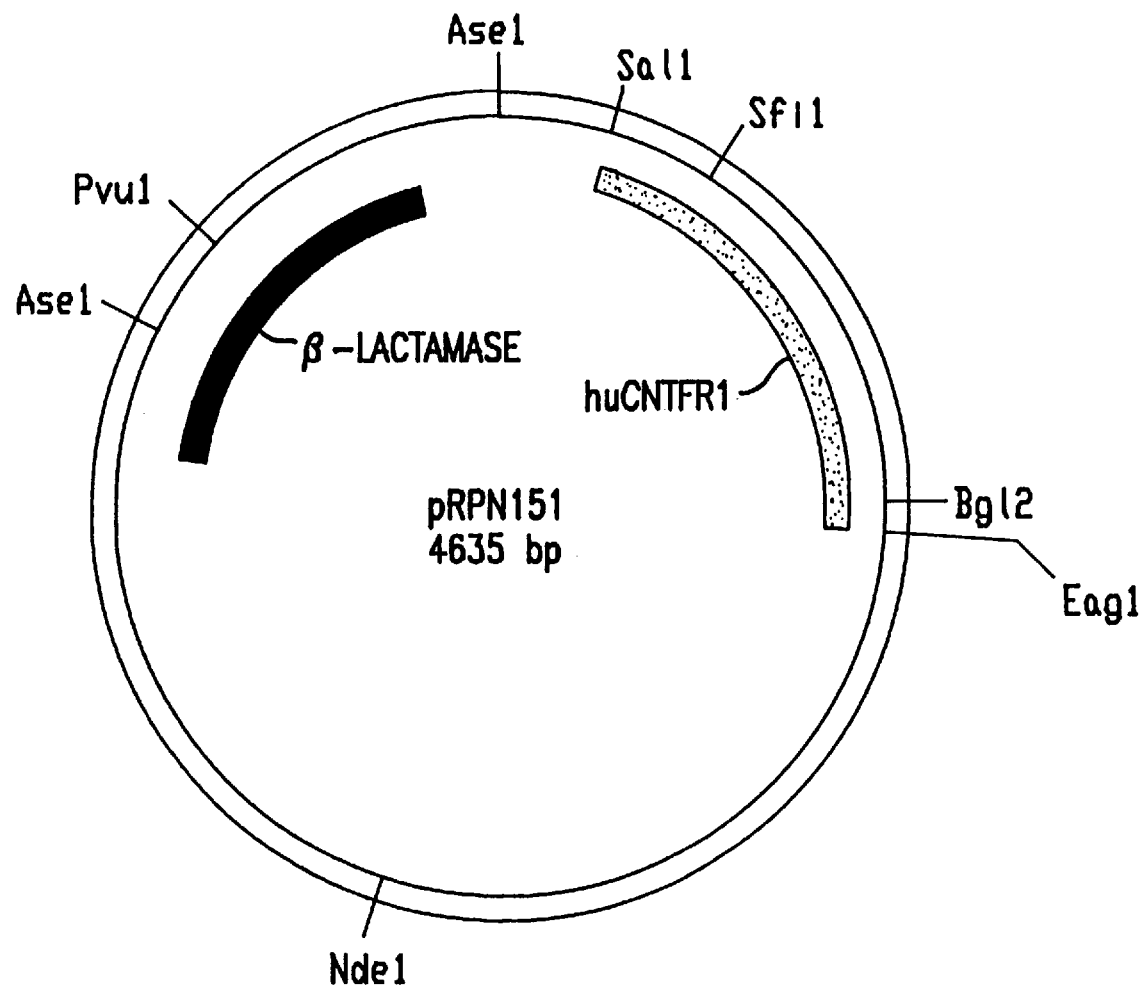

United States Patent [19]
Stahl et al.

[11] Patent Number: 5,955,290
[45] Date of Patent: Sep. 21, 1999

[54] ASSAY SYSTEMS USING THE CNTF SIGNAL TRANSDUCTION PATHWAY

[75] Inventors: Neil Stahl, Carmel; George D. Yancopoulos, Briarcliff Manor, both of N.Y.; James N. Ihle, Memphis, Tenn.

[73] Assignees: Regeneron Pharmaceuticals, Inc., Tarrytown, N.Y.; St. Jude Children's Research Hospital, Memphis, Tenn.

[21] Appl. No.: 08/603,010

[22] Filed: Feb. 16, 1996

Related U.S. Application Data

[63] Continuation of application No. 08/118,968, Sep. 9, 1993, abandoned, which is a continuation-in-part of application No. 08/097,997, Jul. 29, 1993, and application No. 07/865,878, Apr. 8, 1992, Pat. No. 5,332,672, which is a continuation-in-part of application No. 07/801,562, Dec. 2, 1991, abandoned.

[51] Int. Cl.$^6$ ...................................................... C12Q 1/00
[52] U.S. Cl. .................. 435/7.21; 435/15; 435/69.1; 435/252.3; 435/254.11; 435/325; 530/350; 530/351
[58] Field of Search ................... 435/7.21, 7.2, 435/15, 326, 69.1, 252.3, 254.11; 530/350, 351

[56] References Cited

PUBLICATIONS

Ip et al., Cell, vol. 69, p. 1121, 1992.
Stahl et al., Journal of Biol. Chem., vol. 268, p. 7628, 1993.
Velazquez et al., Cell, vol. 70, p. 313, 1992.
Wilks et al., Mol. Cell. Biol., vol. 11, p. 2057, 1991.
Witthuchor et al., Cell., vol. 74, p. 227, 1993.

*Primary Examiner*—John Ulm
*Assistant Examiner*—Sally P. Teng
*Attorney, Agent, or Firm*—Gail M. Kempler

[57] ABSTRACT

The present invention provides for a stable, biologically active CNTF/receptor complex, and hybrids or mutants thereof. The invention is also based in part on the discovery that the CNTF/receptor complex promotes differentiation through a signal transduction pathway on target cells that do not express the CNTF receptor. The invention further provides for a specific CNTFR mutant that promotes signal transduction without binding CNTF. The invention also provides for a CNTF/receptor blocking mutant, a mutant possessing a high binding affinity to CNTF, but possessing no signal transducing function. The present invention also identifies receptor components shared by the IL-6, CNTF, LIF and OSM signal transduction pathways, and the assay systems based on the use of such components.

20 Claims, 39 Drawing Sheets

```
                                                                                                                                  GTGCA
CAATCCCCATTAGTAGAGAATGCCAGTGGGTTTAGTCTCTTTGAGAGTCACATCTCCTTATTTG

GACCAGTATAGACAGAAGTAAACCCAGCTGACTTGTTTCCTGGGACAGTTGAGTTAAGGG

M   A   F   T   E   H   S   P   L   T   P   H   R   R   D   L   C   S   R   S
ATGGCTTTCACAGAGCATTCACCGCTGACCCCTCACCGTCGGGACCTCTGTAGCCGCTCT

I   W   L   A   R   K   I   R   S   D   L   T   A   L   T   E   S   Y   V   K
ATCTGGCTAGCAAGGAAGATTCGTTCAGACCTGACTGCTCTTACGGAATCCTATGTGAAG

H   Q   G   L   N   K   N   I   N   L   D   S   A   D   G   M   P   V   A   S
CATCAGGGCCTGAACAAGAACATCAACCTGGACTCTGCGGATGGGATGCCAGTGGCAAGC

T   D   Q   W   S   E   L   T   E   A   E   R   L   Q   E   N   L   Q   A   Y
ACTGATCAGTGGAGTGAGCTGACCGAGGCAGAGCGACTCCAAGAGAACCTTCAAGCTTAT

R   F   H   V   L   L   A   R   L   L   E   D   Q   Q   V   H   F   T   P
CGTACCTTTCCATGTTTTGTTGGCCAGGCTCTTAGAAGACCAGGTGCATTTTACCCCA
```

FIG. 1A

```
T   E   G   D   F   H   Q   A   I   H   T   L   L   L   Q   V   A   A   F   A
ACCGAAGGTGACTTCCATCAAGCTATACATACCCTTCTCCAAGTCGCTGCCTTTGCA

Y   Q   I   E   E   L   M   I   L   L   E   Y   K   I   P   R   N   E   A   D
TACCAGATAGAGGAGTTAATGATACTCCTGGAATACAAGATCCCCGCAATGAGGCTGAT

G   M   P   I   N   V   G   D   G   G   L   F   E   K   K   L   W   G   L   K
GGGATGCCTATTAATGTTGGAGATGGTGGTCTCTTTGAGAAGAAGCTGTGGGGCCTAAAG

V   L   Q   E   L   S   Q   W   T   V   R   S   I   H   D   L   R   F   I   S
GTGCTGCAGGAGCTTTCACAGTGGACAGTAAGGTCCATGACCTTCGTTTCATTTCT

S   H   Q   T   G   I   P   A   R   G   S   H   Y   I   A   N   N   K   K   M
TCTCATCAGACTGGGATCCCAGCACGTGGGAGCCATTATATTGCTAACAACAAGAAAATG

TAGCAGTTAGTCCCTCCTTCCTCTCCTTACTTTCCTTCTCTAATGGAATATGCGTAGTT
```

FIG. 1B

```
        10              20              30              40              50              60              70              80
CCTCGAGATC CATTGTGCTC AAAGGGCGGC GGCAGCGGAG GCGGGGGCTC CAGCCGGCGC GCGGCGAGGC GGGCCGGCGC TCGGCGGTGG
GGAGCTCTAG GTAACACGAG TTTCCCGCCG CCGTCGCCTC CGCCGCGCGG CGGCCGGCGG GCGGCGTCCG AGCCGCCACC
        90              100             110             120             130             140             150
GATCCGGCGG GCGGTGCTAG CTCCGGCTC CCTGCCTCGC TGCCTCGCGG GGGCGGTCGG AAGGCGGGC
CTAGGCCGCC CGCCACGATC GAGGCGGGAG GGACGGAGCG AGCGACGGCC CCCGCCAGCC TTCCGCCG
        160             170             180             190             200             210             220             230
                 GCGAAGCCCG GGTGGCCCGA GGGCGCGACT CTAGCCTTGT CACCTCATCT TGCCCCTTG GTTTGGAAG TCCTGAAGAG
                 CGCTTCGGC CCACCGGGCT CCCGCGCTGA GATCGGAACA GTGGAGTAGA ACGGGGAAC CAAAACTTC AGGACTTCTC
        240             250             260             270             280             290             300
TTGGTCTGGA GGAGGAGGAG GACATTGATC TGCTTGGTGT GTGGCCAGTG GTGAAGAG ATG GCT GCT CCT GTC
AACCAGACCT CCTCCTCCTC CTGTAACTAC ACGAACCACA CACCGGTCAC CACTTCTC TAC CGA CGA GGA CAG
                                                                      Met Ala Ala Pro Val>
        310     320     330     340     350     360
CCG TGG GCC TGC TGT GCT GTG CTT GCC GCC GCC GCA GTT GTC GCC CAG AGA CAC AGT CCA
GGC ACC CGG ACG ACA CGA GAA CGG CGG CGG CGT CAA CAG ATG ATG CGG GTC TCT GTG TCA GGT
Pro Trp Ala Cys Cys Ala Val Leu Ala Ala Ala Ala Val Val Tyr Ala Gln Arg His Ser Pro
370                     380             390             400             410             420             430
CAG GAG GCA CCC CAT GTG CTC CAG TAC GAG CGC CTG GGC TCT GAC GTG ACA CTG CCA TGT GGG ACA
GTC CTC CTC CGT GGG GTA CAC GAG CTC ATG CTC GCG GAC CTG CAC CTG GAC GGT ACA CCC TGT
Gln Glu Ala Pro His Val Gln Leu Tyr Glu Arg Leu Gly Ser Asp Val Thr Leu Pro Cys Gly Thr>
        440     450     460     470     480     490
GCA AAC TGG GAT GCT GCG GTG ACG TGG CGG GTA AAT GGG ACA GAC CTG GCC CCT GAC CTG CTC AAC
CGT TTG ACC CTA CGA CGC CAC CGC CAT TTA CCC TGT CTG GAC CGG GGA CTG GAC GAG TTG
Ala Asn Trp Asp Ala Ala Val Thr Trp Arg Val Asn Gly Thr Asp Leu Ala Pro Asp Leu Leu Asn
500                             510             520             530             540             550             560
GGC TCT CAG CTG GTG CTC CAT GTG CTG GAA CTG GGC CAC CTG TAC GCC TTC CAC
CCG AGA GTC GAC CAC GAG GTA CAC CCG GAC CTT GAC CTT GAC CCG GTG TCA CCG GAG ATG CGG ACG AAG GTG
Gly Ser Gln Leu Val Leu His Gly Leu Glu Leu Gly His Ser Gly Leu Tyr Ala Cys Phe His>
```

FIG.2A

FIG. 2B

```
            570             580             590             600             610             620
CGT GAC TCC TGG CAC CTG CGC CAC CAA GTC CAT GTG GGC TTG CCG CCG CGG GAG CCT GTG
GCA CTG AGG ACC GTG GAC GCG GTT CAG GTA CAC CCG AAC GGC GCC CTC GGA CAC
Arg Asp Ser Trp His Leu Arg His Gln Val Leu Leu His Val Gly Leu Pro Pro Arg Glu Pro Val
630             640             650             660             670             680             690
CTC AGC TGC CGC TCC AAC ACT TAC CCC AAG GGC TTC TAC TGC AGC TGG CAT CTG CCC ACC CCC
GAG TCG ACG GCG AGG TTG TGA ATG GGG TTC CCG AAG ATG ACG TCG ACC GTA GAC GGG TGG GGG
Leu Ser Cys Arg Ser Asn Thr Tyr Pro Lys Gly Phe Tyr Cys Ser Trp His Leu Pro Thr Pro>
        700             710             720             730             740             750
ACC TAC ATT CCC AAC ACC TTC AAT GTG CTG ACT GTG CTG CAT GGC TCC AAA ATT ATG GTC TGT GAG AAG
TGG ATG TAA GGG TTG TGG AAG TTA CAC TGA CAC GAC GTA CCG AGG TTT TAA TAC CAG ACA CTC TTC
Thr Tyr Ile Pro Asn Thr Phe Asn Val Thr Val His Gly Ser Lys Ile Met Val Cys Glu Lys
    760             770             780             790             800             810
GAC CCG GCC CTC AAG AAC CGC TGC CAC ATT CGC TAC ATG CAC CTG TTC TCC ACC ATC AAG TAC
CTG GGT CGG GAG TTC TTG GCG ACG GTG TAA GCG ATG TAC GTG AAG AGG TGG TAG TTC ATG
Asp Pro Ala Leu Lys Asn Arg Cys His Ile Arg Tyr Met His Leu Phe Ser Thr Ile Lys Try>
820             830             840             850             860             870             880
AAG GTC TCC ATA AGT GTC AGC AAT GCC CTG GGC CAC AAT GCT ATC ACC TTT GAC GAG TTC
TTC CAG AGG TAT TCA CAG TCG TTA CGG GAC CCG GTG TTA CGA TAG TGG AAA CTG CTC AAG
Lys Val Ser Ile Ser Val Ser Asn Ala Leu Gly His Asn Ala Thr Ala Ile Thr Phe Asp Glu Phe
        890             900             910             920             930             940
ACC ATT GTG AAG CCT GAT CCT CCA GAA AAT GTG GCC CGG CCA GTG CCC AGC AAC CCT CGC
TGG TAA CAC TTC GGA CTA GGA GGT CTT TTA CAC CGG GCC GGT CAC GGG TCG TTG GGA GCG
Thr Ile Val Lys Pro Asp Pro Pro Glu Asn Val Ala Arg Pro Val Pro Ser Asn Pro Arg>
950             960             970             980             990             1000             1010
CGG CTG GAG GTG ACG TGG CAG ACC CCC TCG GAC CCT GAG TCT TTT CCT GAG TCA AAG TTC
GCC GAC CTC CAC TGC ACC GTC TGG GGG AGC CTG GAC CTG GGA CTC AGA AAA GGA CTC AAG TTC
Arg Leu Glu Val Thr Trp Gln Thr Pro Ser Thr Pro Asp Pro Glu Ser Phe Pro Leu Lys Phe
```

```
     1020          1030          1040          1050          1060          1070
TTT CTG CGC TAC CGA CCC CTC ATC CTG GAC CAG CAT GTG GAG CTG TCC GAC GGC ACA
AAA GAC GCG ATG GCT GGG GAG TAG GAC CTG GTC ACC GTA CAC CTC GAC AGG CCG TGT
Phe Leu Arg Tyr Arg Pro Leu Ile Leu Asp Gln His Val Glu Leu Ser Asp Gly Thr>

1080          1090          1100          1110          1120          1130          1140
GCA CAC ACC ATC ACA GAT CTA GCC TAC GCC GGG CCC TTC CTC ATG AAG GAG TAC ATT ATC CAG GTG GCA GCC AAG GAC AAT
CGT GTG TGG TAG TGT CTA GAT CGG ATG CGG CCC GGG AAG GAC TAC TTC CTC ATG TAA TAG GTC CAC CGT CGG TTC CTG TTA
Ala His Thr Ile Thr Asp Ala Tyr Ala Gly Pro Phe Leu Met Lys Glu Tyr Ile Ile Gln Val Ala Ala Lys Asp Asn
                    1150          1160          1170          1180          1190          1200
GAG ATT GGG ACA TGG AGT GAC TGG AGC GTA GCC CAC GCT CGG GTG CCC TGG ACT GAG GAA CCG
CTC TAA CCC TGT ACC TCA CTG ACG TCG CAT CGG GTG CGA TGC GGG ACC TGA CTC CTT GGC
Glu Ile Gly Thr Trp Ser Asp Trp Ser Val Ala His Ala Arg Val Pro Trp Thr Glu Glu Pro>

1210          1220          1230          1240          1250          1260          1270
CGA CAC CTC ACC ACG GAG GCC CAG GCT GCG ACC GAG ACC ACC AGC TCC CTG GCA CCC
GCT GTG GAG TGG TGC CTC CGG GTC CGA CGC TGG CTC TGG TCG TGG TCG AGG GAC CGT GGG
Arg His Leu Thr Thr Glu Ala Gln Ala Ala Glu Thr Thr Ser Thr Ser Ser Leu Ala Pro
                    1280          1290          1300          1310          1320          1330
CCA CCT ACC ACG AAG ATC TGT GAC CCT GGG GAG CTG GGC AGC CCG GGA CCC TGC GCA CCC
GGT GGA TGG TGC TTC TAG ACA CTG GGA CCC CTC GAC CCG TCG GGC CCT GGG ACG CGT GGG
Pro Pro Thr Thr Lys Ile Cys Asp Pro Gly Leu Gly Ser Gly Gly Gly Pro Cys Ala Pro>

1340          1350          1360          1370          1380          1390          1400
TTC TTG GTC AGC GTC CCC ATC ACT CTG GCC CTG GCT GCC ACT GCC AGC AGT CTC TTG
AAG AAC CAG TCG CAG GGG TAG TGA GAC CGG GAC CGA CGG CGG TGA CGG TCG TCA GAG AAC
Phe Leu Val Ser Val Pro Ile Thr Leu Ala Leu Ala Ala Thr Ala Ser Ser Leu Leu
                    1410          1420          1430          1440          1450          1460          1470
ATC TGAGCC CGGCACCCCA TGAGGACATG CAGAGACACCT GCAGAGGAGC AGGAGGCCGG AGCTGAGCCT
TAG ACTCGG GCCGTGGGGT ACTCCTGTAC GTCTCGTGGA CGTCTCCTCG TCCTCCGGCC TCGACTCGGA
Ile>
```

FIG.2C

```
     1480       1490       1500       1510       1520       1530       1540       1550
GCAGACCCCG GTTTCTATTT TGCACACGGG CAGGAGGACC TTTTGCATTC TCTTCAGACA CAATTTGTTGG AGACCCCGGC
CGTCTGGGGC CAAAGATAAA ACGTGTGCCC GTCCTCCTGG AAAACGTAAG AGAAGTCTGT GTTAAACACC TCTGGGGCCG
     1560       1570       1580       1590
GGGCCCGGGC CTGCCGCCCC CCAGCCCTGC CGCACCAAGC T
CCCGGGCCCG GACGGCGGGG GGTCGGGACG GCGTGGTTCG A
```

FIG.2D

Sense:        5' CGCAGTGTCGACAGCaCAGCGTCACAGTCCACAaGAaGCACCC 3'  EVD-30:43mer
                 SalI Anti-sense:   3' GCCCCCTGGGACGCGTGGGATTAGCCGGCCAGG 5'  EVD-31:35mer
                                             EagI

FIG. 3

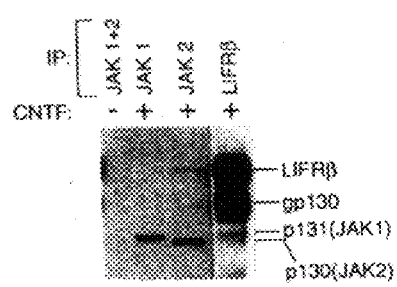
Fig. 23A EW-1 Cells
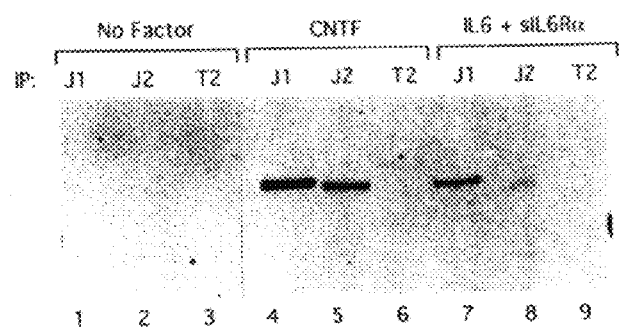
Fig. 23B EW-1 Cells
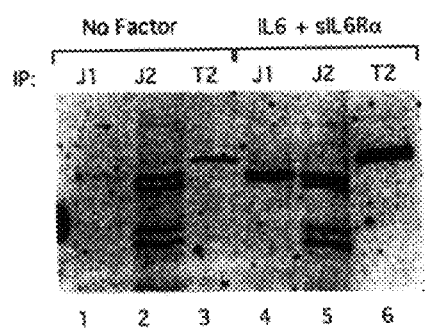
Fig. 23C U266 Cells
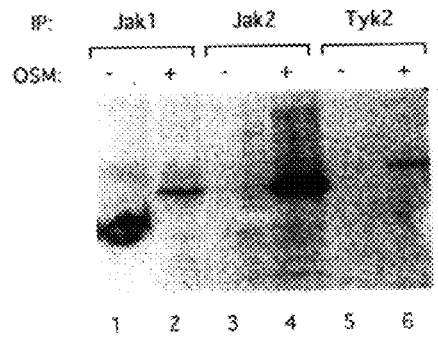
Fig. 23D SK-MES Cells

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 782 base pairs
      (B) TYPE: nucleic acid
      (C) STRANDEDNESS: single
      (D) TOPOLOGY: unknown (ii) MOLECULE TYPE: DNA (ix) FEATURE:
      (A) NAME/KEY: CDS
      (B) LOCATION: 126..725

(xi) SEQUENCE DESCRIPTION: SEQ ID NO:1:

```
GTGCACAATC CCATTAGTAG AGAATGCCAG TGGGTTTAGT CTTTGAGAGT CACATCTCTT        60

ATTTGGACCA GTATAGACAG AAGTAAACCC AGCTGACTTG TTTCCTGGGA CAGTTGAGTT       120

AAGGG ATG GCT TTC ACA GAG CAT TCA CCG CTG ACC CCT CAC CGT CGG           167
      Met Ala Phe Thr Glu His Ser Pro Leu Thr Pro His Arg Arg
      1               5                   10

GAC CTC TGT AGC CGC TCT ATC TGG CTA GCA AGG AAG ATT CGT TCA GAC          215
Asp Leu Cys Ser Arg Ser Ile Trp Leu Ala Arg Lys Ile Arg Ser Asp
15                  20                  25                  30

CTG ACT GCT CTT ACG GAA TCC TAT GTG AAG CAT CAG GGC CTG AAC AAG          263
Leu Thr Ala Leu Thr Glu Ser Tyr Val Lys His Gln Gly Leu Asn Lys
                35                  40                  45

AAC ATC AAC CTG GAC TCT GCG GAT GGG ATG CCA GTG GCA AGC ACT GAT          311
Asn Ile Asn Leu Asp Ser Ala Asp Gly Met Pro Val Ala Ser Thr Asp
            50                  55                  60

CAG TGG AGT GAG CTG ACC GAG GCA GAG CGA CTC CAA GAG AAC CTT CAA          359
Gln Trp Ser Glu Leu Thr Glu Ala Glu Arg Leu Gln Glu Asn Leu Gln
        65                  70                  75

GCT TAT CGT ACC TTC CAT GTT TTG TTG GCC AGG CTC TTA GAA GAC CAG          407
Ala Tyr Arg Thr Phe His Val Leu Leu Ala Arg Leu Leu Glu Asp Gln
    80                  85                  90

CAG GTG CAT TTT ACC CCA ACC GAA GGT GAC TTC CAT CAA GCT ATA CAT          455
Gln Val His Phe Thr Pro Thr Glu Gly Asp Phe His Gln Ala Ile His
95                  100                 105                 110

ACC CTT CTT CTC CAA GTC GCT GCC TTT GCA TAC CAG ATA GAG GAG TTA          503
Thr Leu Leu Leu Gln Val Ala Ala Phe Ala Tyr Gln Ile Glu Glu Leu
                115                 120                 125
```

```
ATG ATA CTC CTG GAA TAC AAG ATC CCC CGC AAT GAG GCT GAT GGG ATG      551
Met Ile Leu Leu Glu Tyr Lys Ile Pro Arg Asn Glu Ala Asp Gly Met
        130                 135                 140

CCT ATT AAT GTT GGA GAT GGT GGT CTC TTT GAG AAG AAG CTG TGG GGC      599
Pro Ile Asn Val Gly Asp Gly Gly Leu Phe Glu Lys Lys Leu Trp Gly
145                 150                 155

CTA AAG GTG CTG CAG GAG CTT TCA CAG TGG ACA GTA AGG TCC ATC CAT      647
Leu Lys Val Leu Gln Glu Leu Ser Gln Trp Thr Val Arg Ser Ile His
    160                 165                 170

GAC CTT CGT TTC ATT TCT TCT CAT CAG ACT GGG ATC CCA GCA CGT GGG      695
Asp Leu Arg Phe Ile Ser Ser His Gln Thr Gly Ile Pro Ala Arg Gly
175                 180                 185                 190

AGC CAT TAT ATT GCT AAC AAC AAG AAA ATG TAGCAGTTAG TCCCTTCTCT        745
Ser His Tyr Ile Ala Asn Asn Lys Lys Met
                195                 200

CTTCCTTACT TTCTCTTCTA ATGGAATATG CGTAGTT                              782

(2) INFORMATION FOR SEQ ID NO:2:

(i) SEQUENCE CHARACTERISTICS:
        (A) LENGTH: 200 amino acids
        (B) TYPE: amino acid
        (D) TOPOLOGY: unknown (ii) MOLECULE TYPE: protein (xi) SEQUENCE DESCRIPTION: SEQ ID NO:2:

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

(2) INFORMATION FOR SEQ ID NO:3:

(i) SEQUENCE CHARACTERISTICS:
        (A) LENGTH: 1591 base pairs
        (B) TYPE: nucleic acid
        (C) STRANDEDNESS: double
```

(D) TOPOLOGY: unknown (ii) MOLECULE TYPE: DNA (cDNA)

(ix) FEATURE:
         (A) NAME/KEY: CDS
         (B) LOCATION: 289..1404

(xi) SEQUENCE DESCRIPTION: SEQ ID NO:3:

```
CCTCGAGATC CATTGTGCTC AAAGGGCGGC GGCAGCGGAG GCGGCGGCTC CAGCCGGCGC      60

GGCGCGAGGC TCGGCGGTGG GATCCGGCGG GCGGTGCTAG CTCCGCGCTC CCTGCCTCGC     120

TCGCTGCCGG GGGCGGTCGG AAGGCGCGGC GCGAAGCCCG GGTGGCCCGA GGGCGCGACT     180

CTAGCCTTGT CACCTCATCT TGCCCCCTTG GTTTTGGAAG TCCTGAAGAG TTGGTCTGGA     240

GGAGGAGGAG GACATTGATG TGCTTGGTGT GTGGCCAGTG GTGAAGAG ATG GCT GCT      297
                                                  Met Ala Ala
                                                    1

CCT GTC CCG TGG GCC TGC TGT GCT GTG CTT GCC GCC GCC GCC GCA GTT      345
Pro Val Pro Trp Ala Cys Cys Ala Val Leu Ala Ala Ala Ala Ala Val
      5                  10                  15

GTC TAC GCC CAG AGA CAC AGT CCA CAG GAG GCA CCC CAT GTG CAG TAC      393
Val Tyr Ala Gln Arg His Ser Pro Gln Glu Ala Pro His Val Gln Tyr
 20                  25                  30                  35

GAG CGC CTG GGC TCT GAC GTG ACA CTG CCA TGT GGG ACA GCA AAC TGG      441
Glu Arg Leu Gly Ser Asp Val Thr Leu Pro Cys Gly Thr Ala Asn Trp
                 40                  45                  50

GAT GCT GCG GTG ACG TGG CGG GTA AAT GGG ACA GAC CTG GCC CCT GAC      489
Asp Ala Ala Val Thr Trp Arg Val Asn Gly Thr Asp Leu Ala Pro Asp
             55                  60                  65

CTG CTC AAC GGC TCT CAG CTG GTG CTC CAT GGC CTG GAA CTG GGC CAC      537
Leu Leu Asn Gly Ser Gln Leu Val Leu His Gly Leu Glu Leu Gly His
         70                  75                  80

AGT GGC CTC TAC GCC TGC TTC CAC CGT GAC TCC TGG CAC CTG CGC CAC      585
Ser Gly Leu Tyr Ala Cys Phe His Arg Asp Ser Trp His Leu Arg His
     85                  90                  95

CAA GTC CTG CTG CAT GTG GGC TTG CCG CCG CGG GAG CCT GTG CTC AGC      633
Gln Val Leu Leu His Val Gly Leu Pro Pro Arg Glu Pro Val Leu Ser
100                 105                 110                 115

TGC CGC TCC AAC ACT TAC CCC AAG GGC TTC TAC TGC AGC TGG CAT CTG      681
Cys Arg Ser Asn Thr Tyr Pro Lys Gly Phe Tyr Cys Ser Trp His Leu
                120                 125                 130

CCC ACC CCC ACC TAC ATT CCC AAC ACC TTC AAT GTG ACT GTG CTG CAT      729
Pro Thr Pro Thr Tyr Ile Pro Asn Thr Phe Asn Val Thr Val Leu His
            135                 140                 145

GGC TCC AAA ATT ATG GTC TGT GAG AAG GAC CCA GCC CTC AAG AAC CGC      777
Gly Ser Lys Ile Met Val Cys Glu Lys Asp Pro Ala Leu Lys Asn Arg
        150                 155                 160

TGC CAC ATT CGC TAC ATG CAC CTG TTC TCC ACC ATC AAG TAC AAG GTC      825
Cys His Ile Arg Tyr Met His Leu Phe Ser Thr Ile Lys Tyr Lys Val
165                 170                 175

TCC ATA AGT GTC AGC AAT GCC CTG GGC CAC AAT GCC ACA GCT ATC ACC      873
Ser Ile Ser Val Ser Asn Ala Leu Gly His Asn Ala Thr Ala Ile Thr
180                 185                 190                 195

TTT GAC GAG TTC ACC ATT GTG AAG CCT GAT CCT CCA GAA AAT GTG GTA      921
Phe Asp Glu Phe Thr Ile Val Lys Pro Asp Pro Pro Glu Asn Val Val
                200                 205                 210

GCC CGG CCA GTG CCC AGC AAC CCT CGC CGG CTG GAG GTG ACG TGG CAG      969
Ala Arg Pro Val Pro Ser Asn Pro Arg Arg Leu Glu Val Thr Trp Gln
            215                 220                 225

ACC CCC TCG ACC TGG CCT GAC CCT GAG TCT TTT CCT CTC AAG TTC TTT     1017
Thr Pro Ser Thr Trp Pro Asp Pro Glu Ser Phe Pro Leu Lys Phe Phe
```

-continued

```
                230                       235                       240
CTG CGC TAC CGA CCC CTC ATC CTG GAC CAG TGG CAG CAT GTG GAG CTG        1065
Leu Arg Tyr Arg Pro Leu Ile Leu Asp Gln Trp Gln His Val Glu Leu
245                     250                     255

TCC GAC GGC ACA GCA CAC ACC ATC ACA GAT GCC TAC GCC GGG AAG GAG        1113
Ser Asp Gly Thr Ala His Thr Ile Thr Asp Ala Tyr Ala Gly Lys Glu
260                     265                     270                 275

TAC ATT ATC CAG GTG GCA GCC AAG GAC AAT GAG ATT GGG ACA TGG AGT        1161
Tyr Ile Ile Gln Val Ala Ala Lys Asp Asn Glu Ile Gly Thr Trp Ser
                280                     285                     290

GAC TGG AGC GTA GCC GCC CAC GCT ACG CCC TGG ACT GAG GAA CCG CGA        1209
Asp Trp Ser Val Ala Ala His Ala Thr Pro Trp Thr Glu Glu Pro Arg
                    295                     300                     305

CAC CTC ACC ACG GAG GCC CAG GCT GCG GAG ACC ACG ACC AGC ACC ACC        1257
His Leu Thr Thr Glu Ala Gln Ala Ala Glu Thr Thr Thr Ser Thr Thr
                310                     315                     320

AGC TCC CTG GCA CCC CCA CCT ACC ACG AAG ATC TGT GAC CCT GGG GAG        1305
Ser Ser Leu Ala Pro Pro Pro Thr Thr Lys Ile Cys Asp Pro Gly Glu
325                     330                     335

CTG GGC AGC GGC GGG GGA CCC TGC GCA CCC TTC TTG GTC AGC GTC CCC        1353
Leu Gly Ser Gly Gly Gly Pro Cys Ala Pro Phe Leu Val Ser Val Pro
340                     345                     350                 355

ATC ACT CTG GCC CTG GCT GCC GCT GCC GCC ACT GCC AGC AGT CTC TTG        1401
Ile Thr Leu Ala Leu Ala Ala Ala Ala Thr Ala Ser Ser Leu Leu
                360                     365                     370

ATC TGAGCCCGGC ACCCCATGAG GACATGCAGA GCACCTGCAG AGGAGCAGGA            1454
Ile

GGCCGGAGCT GAGCCTGCAG ACCCCGGTTT CTATTTTGCA CACGGGCAGG AGGACCTTTT     1514

GCATTCTCTT CAGACACAAT TTGTGGAGAC CCCGGCGGGC CGGGCCTGC CGCCCCCAG       1574

CCCTGCCGCA CCAAGCT                                                    1591
```

(2) INFORMATION FOR SEQ ID NO:4:

(i) SEQUENCE CHARACTERISTICS:
        (A) LENGTH: 372 amino acids
        (B) TYPE: amino acid
        (D) TOPOLOGY: unknown (ii) MOLECULE TYPE: protein (xi) SEQUENCE DESCRIPTION: SEQ ID NO:4:

```
Met Ala Ala Pro Val Pro Trp Ala Cys Cys Ala Val Leu Ala Ala Ala
1               5                   10                  15

Ala Ala Val Val Tyr Ala Gln Arg His Ser Pro Gln Glu Ala Pro His
            20                  25                  30

Val Gln Tyr Glu Arg Leu Gly Ser Asp Val Thr Leu Pro Cys Gly Thr
        35                  40                  45

Ala Asn Trp Asp Ala Ala Val Thr Trp Arg Val Asn Gly Thr Asp Leu
    50                  55                  60

Ala Pro Asp Leu Leu Asn Gly Ser Gln Leu Val Leu His Gly Leu Glu
65                  70                  75                  80

Leu Gly His Ser Gly Leu Tyr Ala Cys Phe His Arg Asp Ser Trp His
                85                  90                  95

Leu Arg His Gln Val Leu Leu His Val Gly Leu Pro Pro Arg Glu Pro
            100                 105                 110

Val Leu Ser Cys Arg Ser Asn Thr Tyr Pro Lys Gly Phe Tyr Cys Ser
        115                 120                 125

Trp His Leu Pro Thr Pro Thr Tyr Ile Pro Asn Thr Phe Asn Val Thr
```

```
              130                 135                 140
Val Leu His Gly Ser Lys Ile Met Val Cys Glu Lys Asp Pro Ala Leu
145                 150                 155                 160

Lys Asn Arg Cys His Ile Arg Tyr Met His Leu Phe Ser Thr Ile Lys
                165                 170                 175

Tyr Lys Val Ser Ile Ser Val Ser Asn Ala Leu Gly His Asn Ala Thr
            180                 185                 190

Ala Ile Thr Phe Asp Glu Phe Thr Ile Val Lys Pro Asp Pro Pro Glu
        195                 200                 205

Asn Val Val Ala Arg Pro Val Pro Ser Asn Pro Arg Arg Leu Glu Val
    210                 215                 220

Thr Trp Gln Thr Pro Ser Thr Trp Pro Asp Pro Glu Ser Phe Pro Leu
225                 230                 235                 240

Lys Phe Phe Leu Arg Tyr Arg Pro Leu Ile Leu Asp Gln Trp Gln His
                245                 250                 255

Val Glu Leu Ser Asp Gly Thr Ala His Thr Ile Thr Asp Ala Tyr Ala
            260                 265                 270

Gly Lys Glu Tyr Ile Ile Gln Val Ala Ala Lys Asp Asn Glu Ile Gly
        275                 280                 285

Thr Trp Ser Asp Trp Ser Val Ala Ala His Ala Thr Pro Trp Thr Glu
    290                 295                 300

Glu Pro Arg His Leu Thr Thr Glu Ala Gln Ala Ala Glu Thr Thr Thr
305                 310                 315                 320

Ser Thr Thr Ser Ser Leu Ala Pro Pro Thr Thr Lys Ile Cys Asp
                325                 330                 335

Pro Gly Glu Leu Gly Ser Gly Gly Pro Cys Ala Pro Phe Leu Val
            340                 345                 350

Ser Val Pro Ile Thr Leu Ala Leu Ala Ala Ala Ala Thr Ala Ser
        355                 360                 365

Ser Leu Leu Ile
    370

(2) INFORMATION FOR SEQ ID NO:5:

(i) SEQUENCE CHARACTERISTICS:
        (A) LENGTH: 43 base pairs
        (B) TYPE: nucleic acid
        (C) STRANDEDNESS: single
        (D) TOPOLOGY: unknown (ii) MOLECULE TYPE: DNA (ix) FEATURE:
        (A) NAME/KEY: modified_base
        (B) LOCATION: 22
        (D) OTHER INFORMATION: /mod_base= i
            /label= n (xi) SEQUENCE DESCRIPTION: SEQ ID NO:5:

CGCAGTGTCG ACAGCACAGC GNCACAGTCC ACAAGAAGCA CCC                    43

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: unknown (ii) MOLECULE TYPE: DNA (iv) ANTI-SENSE: YES
```

-continued (xi) SEQUENCE DESCRIPTION: SEQ ID NO:6:

GGACGCCGGC CGATTAGGGT GCGCAGGGTC CCCCG                35

ASSAY SYSTEMS USING THE CNTF SIGNAL TRANSDUCTION PATHWAY

This application is a continuation of U.S. Ser. No. 08/118,968 filed on Sep. 9, 1993, now abandoned, which is a continuation-in-part of U.S. patent application Ser. No. 08/097,997 filed on Jul. 29, 1993 and a continuation-in-part of U.S. patent application Ser. No. 07/865,878 filed on Apr. 8, 1992, which issued as U.S. Pat. No. 5,332,672 on Jul. 26, 1994, and which is a continuation-in-part of U.S. patent application Ser. No. 07/801,562 filed on Dec. 2, 1991, now abandoned.

1. INTRODUCTION

The present invention provides for assay systems that may be used to detect and/or measure cytokine activity of ciliary neurotrophic factor (CNTF) as well as other cytokines, such as interleukin-6 (IL-6), oncostatin M (OSM) and leukemia inhibitory factor (LIF) that share receptor components with CNTF. The invention further provides for assay systems that may be used to detect agents that act as agonists or antagonists of CNTF and factors that share receptor components with CNTF.

2. BACKGROUND OF THE INVENTION

2.1. CILIARY NEUROTROPHIC FACTOR

Ciliary neurotrophic factor (CNTF), as its name implies, is a protein that is specifically required for the survival of embryonic chick ciliary ganglion neurons in vitro [Manthorpe et al., J. Neurochem. 34:69–75 (1980)]. CNTF has been cloned and synthesized in eukaryotic as well as bacterial expression systems, as described in International Application No. PCT/U.S. 90/05241, filed Sep. 14, 1990 which published as WO 91/04316 on Apr. 4, 1991 by Sendtner et al., incorporated by reference in its entirety herein.

Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain [Hughes et al., Nature 335:70–73 (1988)]. Furthermore, it has been observed to promote the survival of embryonic chick dorsal root ganglion sensory neurons [Skaper and Varon, Brain Res. 389:39–46 (1986)].

Several novel activities of CNTF have also been discovered, including its ability to support the survival and differentiation of motor neurons and hippocampal neurons, and to increase the rate of hippocampal astrocyte proliferation (International Application No. PCT/US 90/05241 which published as WO 91/04316 on Apr. 4, 1991, supra).

2.2. CILIARY NEUROTROPHIC FACTOR RECEPTOR

The CNTF receptor (CNTFR or CNTFRα) has been cloned and expressed in eukaryotic cells, as described in U.S. patent application Ser. No. 07/700,677, entitled "The Ciliary Neurotrophic Factor Receptor," filed May 15, 1991 now abandoned by Davis, et al. and International Application No. PCT/US 91/03896, filed Jun. 3, 1991 which published as WO 91/19009 on Dec. 12, 1991, incorporated by reference in their entirety herein.

The sequence of CNTFR reveals that, unlike most receptors which contain an extracellular domain, a hydrophobic transmembrane domain, and a cytoplasmic domain, CNTFR does not appear to have a cytoplasmic domain. Additionally, the transmembrane hydrophobic domain is proteolytically processed, with the mature form of CNTFR becoming anchored to the cell surface by an unconventional linkage, referred to as a glycophosphatidyl inositol (GPI) linkage (Id.). GPI-linked proteins such as CNTFR may be released from the cell surface through cleavage of the GPI anchor by the enzyme phosphatidylinositol-specific phospholipase C. Of other known receptor sequences, CNTFR is related to a number of receptors, referred to herein as the CNTF/ IL-6/ LIF receptor family, including IL-6,LIF, G-CSF and oncostatin M (OSM) [Bazan, Neuron 7:197–208 (1991); Rose and Bruce, Proc. Natl. Acad. Sci. 88:8641–8645, (1991)], but appears to be most closely related to the sequence of the receptor for IL-6. However, IL-6 has not been shown to be a GPI-linked protein [e.g., Taga, et al., Cell 58:573–581 (1989); Hibi, et al., Cell 63:1149–1157 (1989)].

The cloning, sequencing and expression of the CNTF receptor (CNTFR) led to the discovery that CNTFR and CNTF may form a complex that interacts with a membrane bound, signal transducing component, thus suggesting therapeutic activity of a soluble CNTF/CNTFR receptor complex (see, for example, copending application U.S. Ser. No. 801,562 filed Dec. 2, 1991 now abandoned by Yancopoulos, et al. entitled "Cell Free Ciliary Neurotrophic Factor/ Receptor Complex", now abandoned, which is incorporated by reference in its entirety herein).

One such signal transducing component involved in high affinity binding of CNTF and the subsequent functional response of the cell has been identified as gp130, a β component common to the IL-6, Oncostatin M, LIF family of receptors [Fukunaga et al., EMBO J. 10:2855–2865 (1991); Gearing et al., EMBO J. 10:2839–2848 (1991); Gearing et al. Science 255:1434–1437 (1992); Ip, et al., Cell 69:1121–1132 (1992)]. A further β component identified as being involved in binding and signal transduction in response to LIF (LIFRβ) appears to be the same or similar to a β component necessary for response to CNTF. (As a consequence of the identification of β components necessary for binding and signal transduction of CNTF, what was originally generally termed CNTFR is currently referred to as CNTFRα).

IL-6 is a pleiotropic cytokine which acts on a wide variety of cells, exerting growth promotion and inhibition and specific gene expression sometimes accompanied by cellular differentiation; its has been implicated as being involved in several diseases including inflammation, autoimmunities and lymphoid malignancies [Kishimoto, et al. Science 258:593- (1992). LIF, G-CSF and OSM are all broadly acting factors that, despite having unique growth-regulating activities, share several common actions with IL-6 during hemopoiesis as well as in other processes. For example, all can inhibit the proliferation and induce the differentiation of the murine myeloid leukemia cell line, M1 [Rose and Bruce, Proc. Natl. Acad. Sci. 88:8641–8645 (1991)]. LIF and Oncostatin M induced tyrosine phosphorylations and gene activations in neuronal cells which are indistinguishable from responses induced by CNTF (Ip, et al. 1992, Cell 69:1121–1132). In copending application U.S. Ser. No. 801,562 filed Dec. 2, 1991 by Yancopoulos, et al. entitled "Cell Free Ciliary Neurotrophic Factor/Receptor Complex", which is incorporated by reference in its entirety herein, CNTF and CNTFRα are combined to form a stable, biologically active complex that can be used as a differentiation or proliferation factor in cell types that express signal transducing receptor components belonging to the CNTF/

IL-6/LIF receptor family. As described in U.S. application Ser. No. 07/865,878 filed on Apr. 8, 1992 entitled "Cell-Free Ciliary Neurotrophic Factor/Receptor Complex", which is incorporated by reference in its entirety herein, signal transduction can be initiated by treatment of cells expressing both gp130 and LIFRβ with a soluble CNTF/CNTFRα complex. Alternatively, target cells not previously responsive to CNTF, but expressing LIFRB and gp130 (such as LIF-responsive cells) can be made responsive to CNTF by attaching the CNTFRα to the cells and subsequently treating with CNTF.

Although the events surrounding CNTF binding and receptor activation have recently been elucidated [Davis, et al. Science 253:59–63 (1991); Ip, et al., Cell 69:1121–1132 (1992); Stahl et al., Cell 74:587–590 (1993); Davis et al., Science 260:1805–1018 (1993)], the mechanism by which signal transduction is initiated inside the cell is more poorly understood. Like the other distantly related receptors for the extended cytokine family—which includes Interleukin (IL)-3, IL-5, GM-CSF, G-CSF, EPO, GH, and the interferons [(Bazan, J. F. Proc. Natl. Acad. Sci. U.S.A. 87:6934–6938 (1990); Bazan, J. F. Neuron 7:197–208 (1991)]—the CNTF receptor β subunits gp130 and LIFRβ do not have protein tyrosine kinase domains in their cytoplasmic regions (Hibi et al., Cell 63:1149–1157 (1990); Gearing et al., EMBO J. 10:2839–2848 (1991). In spite of this, CNTF-induced dimerization of the β subunits somehow results in the rapid accumulation of a set of tyrosine phosphorylated proteins called the CLIPs [Ip, et al., Cell 69:1121–1132 (1992)].

Although, as described above, two of the more prominent CLIPs were identified as the β subunits themselves, most of the others have yet to be characterized. The activation of cytoplasmic tyrosine kinase(s) appears to be essential for CNTF action since inhibitors that block the tyrosine phosphorylations also block subsequent downstream events such as gene inductions [Ip, et al., Cell 69:1121–1132 (1992)].

A possible clue to the identity of the cytoplasmic tyrosine kinase(s) activated by the CNTF family of factors came from the finding that other distantly related cytokines resulted in the activation of the Jak/Tyk family of kinases (Firmbach-Kraft et al., Oncogene 5:1329–1336 (1990); Wilks et al., Mol. Cell. Biol 11:2057–2065 (1991); Harpur et al., Oncogene 7:1347–1353 (1992). This family of non-receptor cytoplasmic protein tyrosine kinases consists of 3 known members—Jak1, Jak2, and Tyk2—which are all equally related to each other and share the unusual feature of having two potential kinase domains and no Src homology 2 (SH2) domains. Elegant studies involving complementation of a genetic defect in a cell line unresponsive to IFNα resulted in the identification of Tyk2 as a required component of the IFNα signaling cascade [(Velazquez et al., Cell 70:313–322 (1992)]. More recently, the receptors for cytokines such as EPO, GM-CSF, and GH were shown to associate with and activate Jak2 [Argetsinger et al., Cell 74:237–244 (1993); Silvennoinen et al., Proc. Natl. Acad. Sci U.S.A., 90 8429 (1993) Witthuhn et al., Cell 74:227–236 (1993)]. The kinase was shown to bind to the membrane proximal cytoplasmic region of the receptor, and mutations of this region that prevented Jak2 binding also resulted in the loss of EPO induced proliferation, suggesting that Jak2 plays a critical role in EPO signaling. Jak1 has not been reported to be significantly activated by any of these receptor systems.

The identification of hemopoietic factors that share receptor components with CNTF would enable the utilization of CNTF and its specific receptor components for activation of targeted cells that are normally responsive to such hemopoietic factors.

3. SUMMARY OF THE INVENTION

The present invention provides for assay systems that may be used to detect and/or measure CNTF activity, or activity of other cytokines, such as LIF, Oncostatin M or IL-6 that utilize receptor components in common with CNTF (hereinafter the "CNTF receptor family"). The present invention also provides for assay systems that may be used to identify agents that act as agonists or antagonists of members of the CNTF receptor family. It is based, in part, on the discovery that CNTF receptor family members utilize, as part of their signal transduction pathway, the CLIP signal transduction pathways and the Jak family of kinases.

The present invention further relates to a cell-free CNTF/receptor complex. It is based, in part, on the discovery that cell-free CNTF/receptor complex is biologically active on a broader spectrum of cell types than those that express the CNTF receptor. In a specific embodiment of the invention, the CNTF/receptor acts as a differentiation factor in cell types that express receptors belonging to the CNTF/IL-6/LIF receptor family.

The present invention is further based on the ability of CNTF and cell-free CNTFR to form a stable, biologically active CNTF/receptor complex under normal physiological buffer conditions. In one specific nonlimiting embodiment of the invention, equimolar amounts (e.g., 80 mM) of recombinant CNTF and CNTFR are mixed under normal physiological buffer conditions (100 mM Tris-Hcl, 50 mM NaCl, pH 8.0) to form a stable, biologically active CNTF/receptor complex. This CNTF/receptor complex may be purified via gel filtration and utilized in assays described infra.

The invention further provides for hybrid or mutant proteins related to the CNTF/receptor complex which function as either agonists or antagonists of cellular differentiation factors. For example, in one specific embodiment, a hybrid or mutant CNTFR may be unable to bind CNTF but be capable of signal transduction. This hybrid or mutant may be utilized to promote or enhance the differentiation, proliferation, growth or survival of cells that are responsive to the CNTF/receptor complex, including cells that express receptors that are members of the CNTF/ IL-6/LIF receptor family independent of CNTF levels. In an alternative, non-limiting embodiment, a mutant receptor may exhibit an increased binding affinity for CNTF, but be unable to effectively induce signal transduction. Such a mutant may be useful in binding to and neutralizing CNTF without eliciting secondary effects on cell differentiation.

The invention also provides for in vitro or in vivo diagnostic methods and for assay systems for use in testing target cells for sensitivity to a particular treatment involving the CNTF/receptor.

The invention further provides for therapeutic methods for treating not only CNTF-related disorders but also disorders of differentiation and/or proliferation related to any target cell which is responsive to cell-free CNTF/receptor complex or related compounds.

The present invention also provides for a method of producing substantially purified, biologically active CNTFR or related molecules in bacteria.

The present invention is also based on the discovery that CNTF and LIF act on neuronal cells via the IL-6 transducing receptor component gp130 and a gp130-like second receptor component(referred to as LIFβ), together which, when bound to CNTF and CNTFR initiate signal transduction using a signalling pathway comparable to IL-6. Based on this discovery, the invention provides for the utilization of CNTF and CNTFR to induce a response in cells that are normally responsive to LIF or IL-6 (presumably because they express gp130 and LIFRβ).

The present invention also provides for a method of targeting cells with CNTFR(CNTFRα) so that CNTF can be used to selectively initiate signal transduction in such cells.

The invention further provides for the use of CNTF in place of LIF to prevent differentiation of cultured embryonic stem cells.

4. DESCRIPTION OF THE FIGURES

FIGS. 1A and 1B. Nucleic acid sequence (SEQ ID NO:1) of human CNTF and the deduced amino acid sequence (SEQ ID NO:2).

FIGS. 2A–2D. Nucleic acid sequence (SEQ ID NO:3) of CNTFR encoding cDNA and deduced amino acid sequence (SEQ ID NO:4).

FIG. 3. DNA sequences of the PCR primers used in the construction of pRPN151. Small characters indicate positions at which the DNA sequence was modified in order to optimize expression without modification of the protein sequence. Sense:(SEQ ID NO:5) Anti Sense:(SEQ ID NO:6).

FIG. 4. Physical and restriction map of pRPN151. The length of the plasmid in base pairs (bp), the positions of a few unique restriction sites, as well as the physical location of the hCNTFR (dotted bar) and the beta lactamase (solid bar) genes are shown.

Figure 5A:
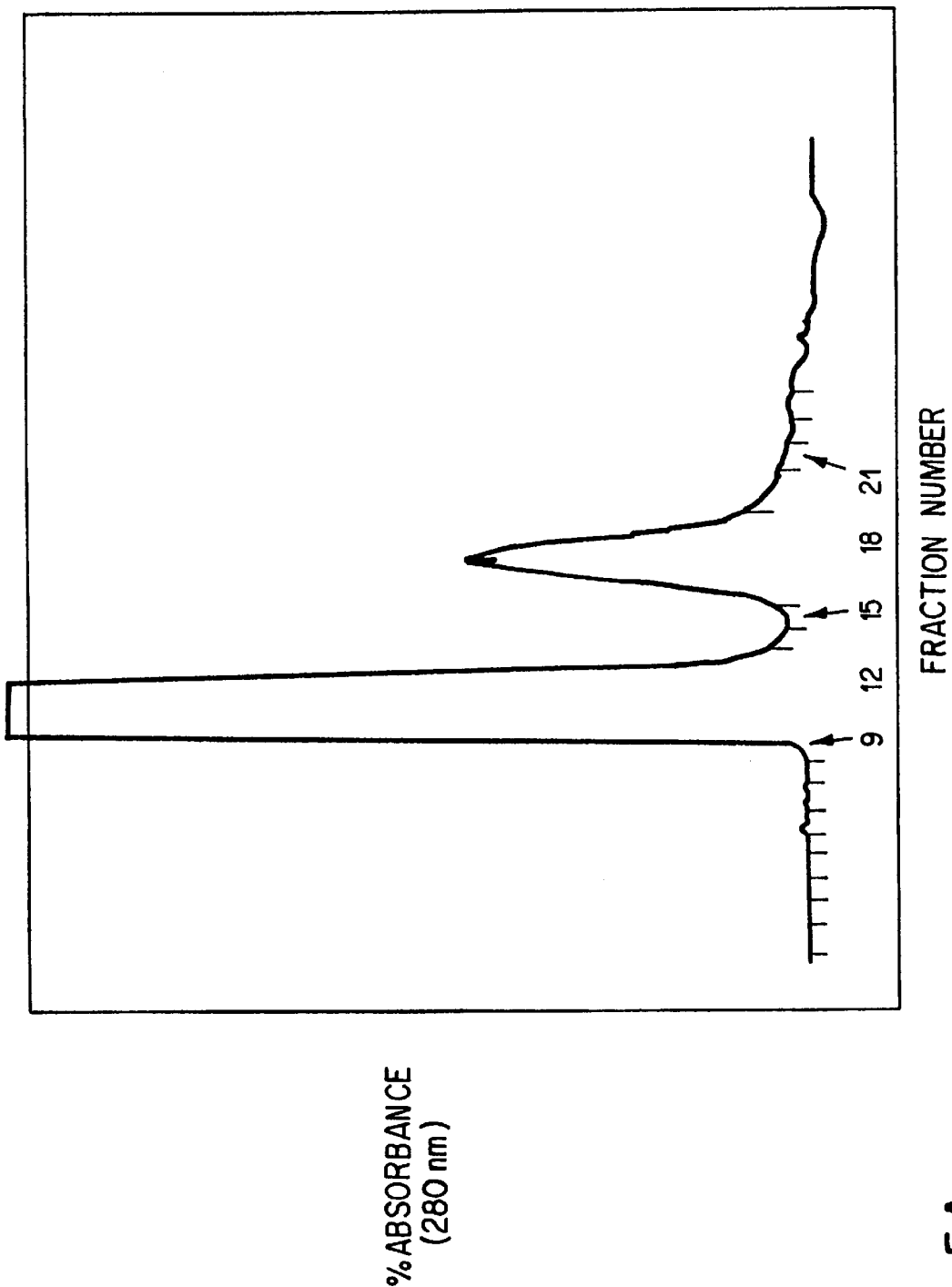
Figure 5B:
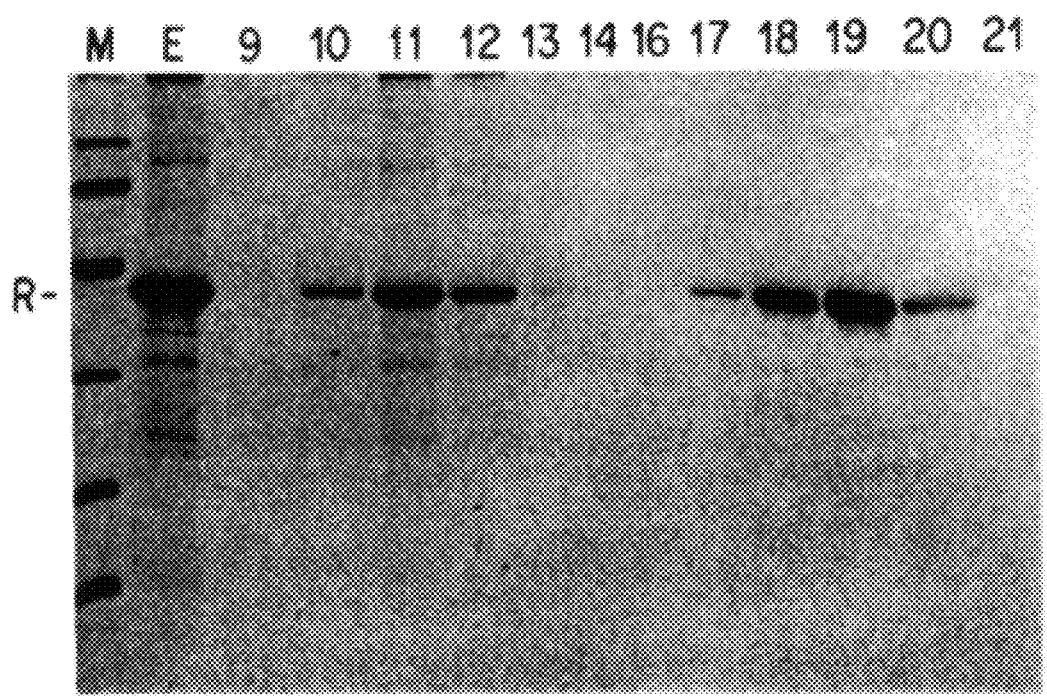

FIGS. 5A and 5B. Isolation of active receptor by gel filtration. FIG. 5A Elution profile of an S100-HR column, monitored by absorbance at 280 nm. Nucleic acids contribute approximately 50% to the absorbance of the major peak but less than 10% to the smaller one. 5B Proteins eluting in fractions 9–14 (20 μl per lane) and 16–21 (200 μl per lane), were analyzed by SDS-PAGE. Total protein extract applied to the column (lane E) is also shown, along with size markers of 14, 21, 31, 45, 66 and 90 kD (lane M). R-, indicates the position of the receptor band at 40 kD.

Figure 6:
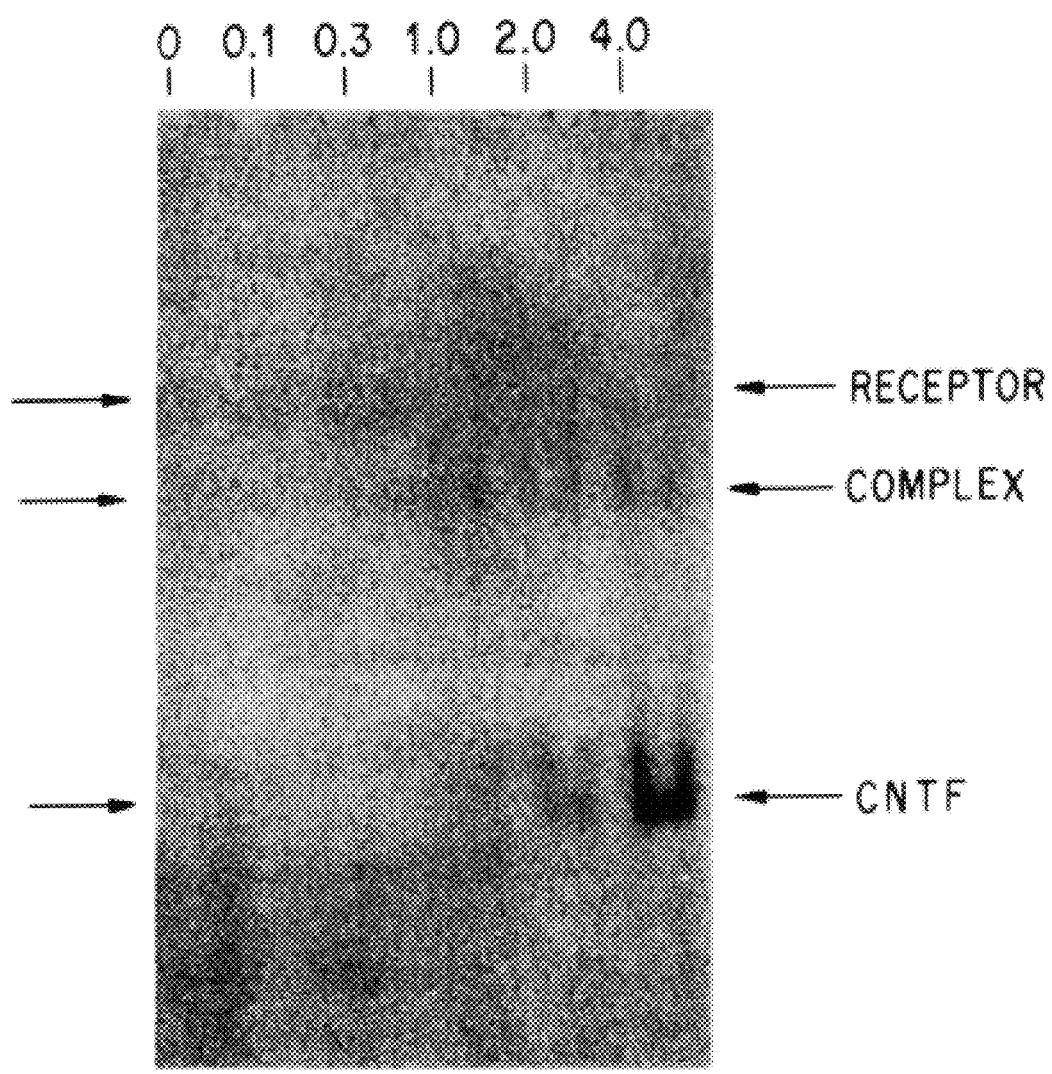

FIG. 6. Receptor ligand complex formation by native PAGE. A constant amount of receptor (1 μg) was mixed with the indicated amounts (in μg) of rat CNTF and analyzed by native PAGE. The positions of the bands corresponding to CNTFR, CNTF, and the CNTF/receptor complex are indicated.

Figure 7A:
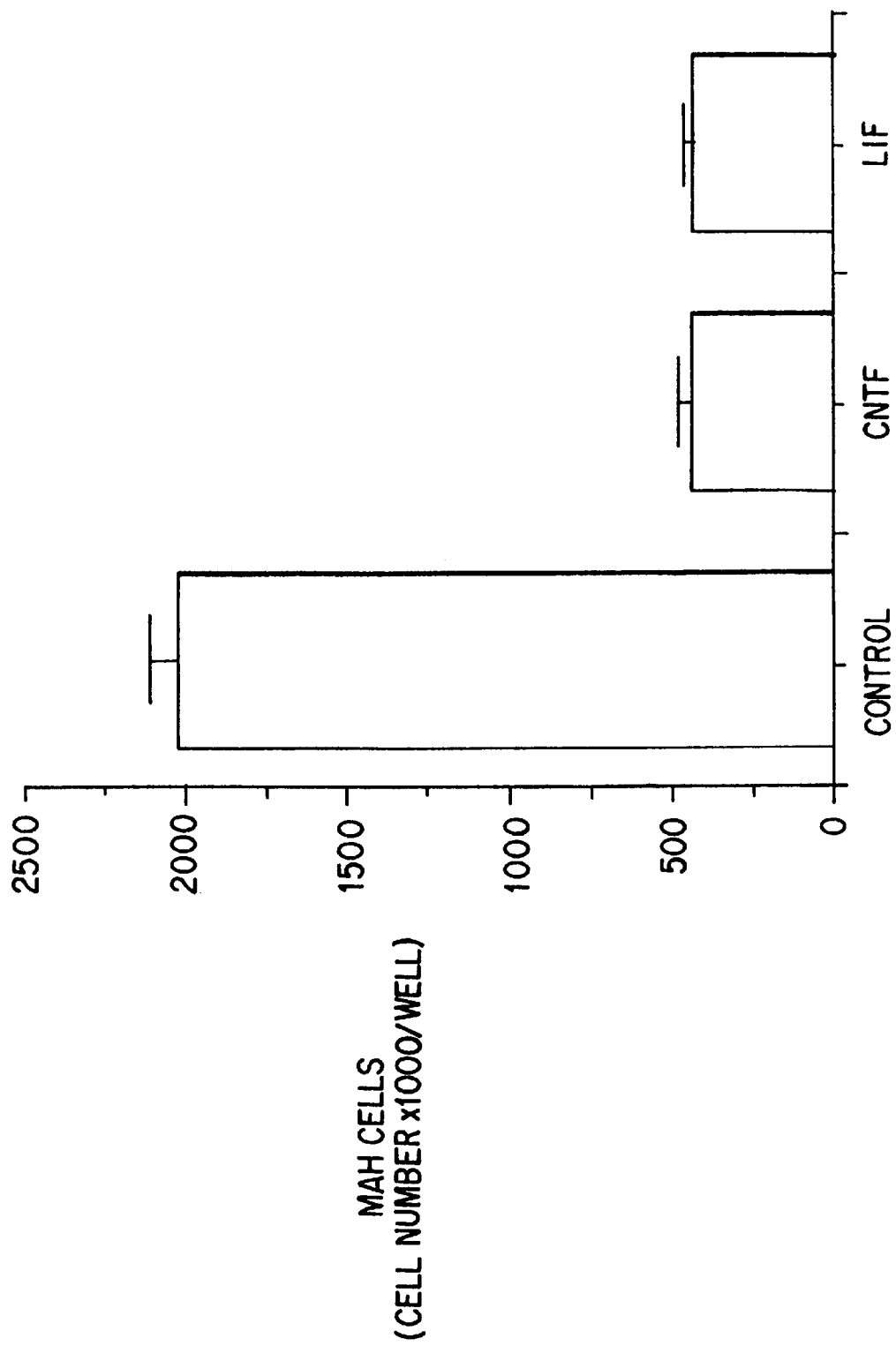
Figure 7B:
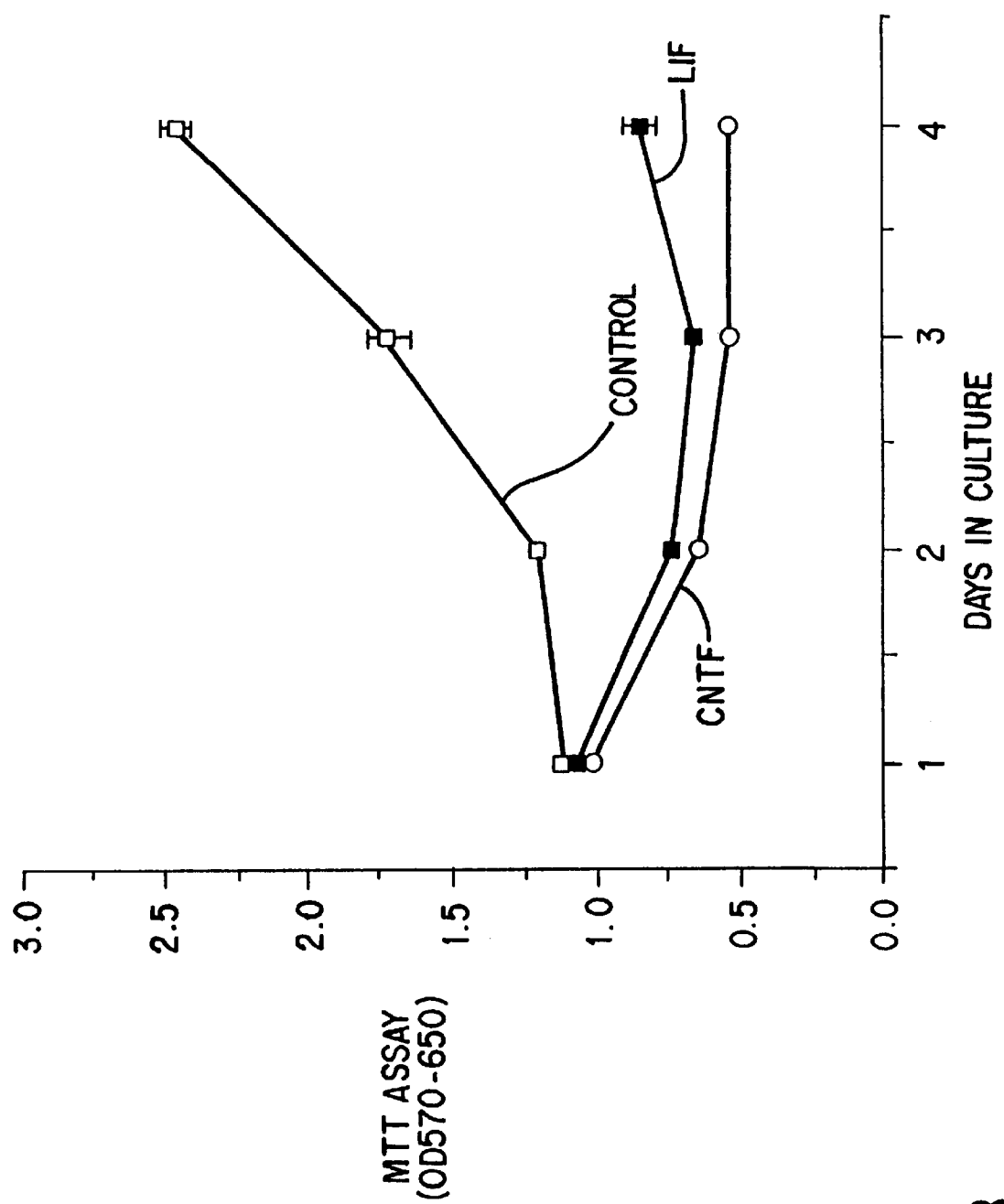
Figure 7C:
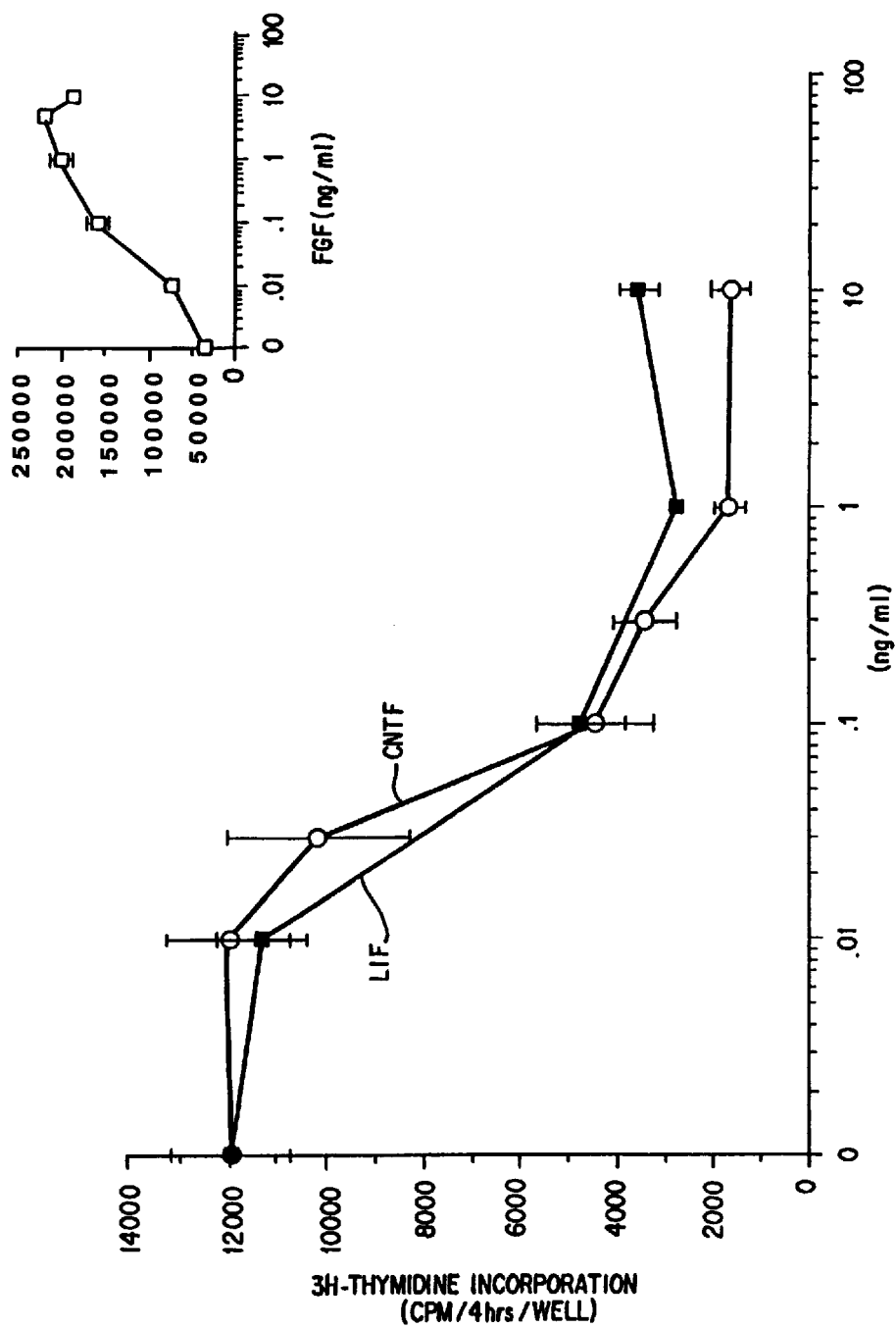

FIGS. 7A–7C. Growth of MAH cells following treatment with CNTF, LIF and FGF. FIG. 7A. MAH cells were plated at a density of 250K/35 mm dish, treated with CNTF (10 ng/ml), or LIF (1 ng/ml) for 4 days in culture. At the end of the culture period, the number of phase-bright cells were counted. FIG. 7B. MAH cells were plated at a density of 6K/6 mm well, treated with CNTF(10 ng/ml), or LIF(1 ng/ml) for 1–4 days, and the number of vital cells were assayed using MTT dye. FIG. 7C. Various concentrations of CNTF, LIF and FGF were added to MAH cells. The culture period was continued for 4 days for CNTF and LIF, and for 3 days for FGF prior to $^3$H-thymidine incorporation assay. Plating density was at 6K/6 mm well for CNTF and LIF, and 40K/16 mm well for FGF.

Figure 8A:
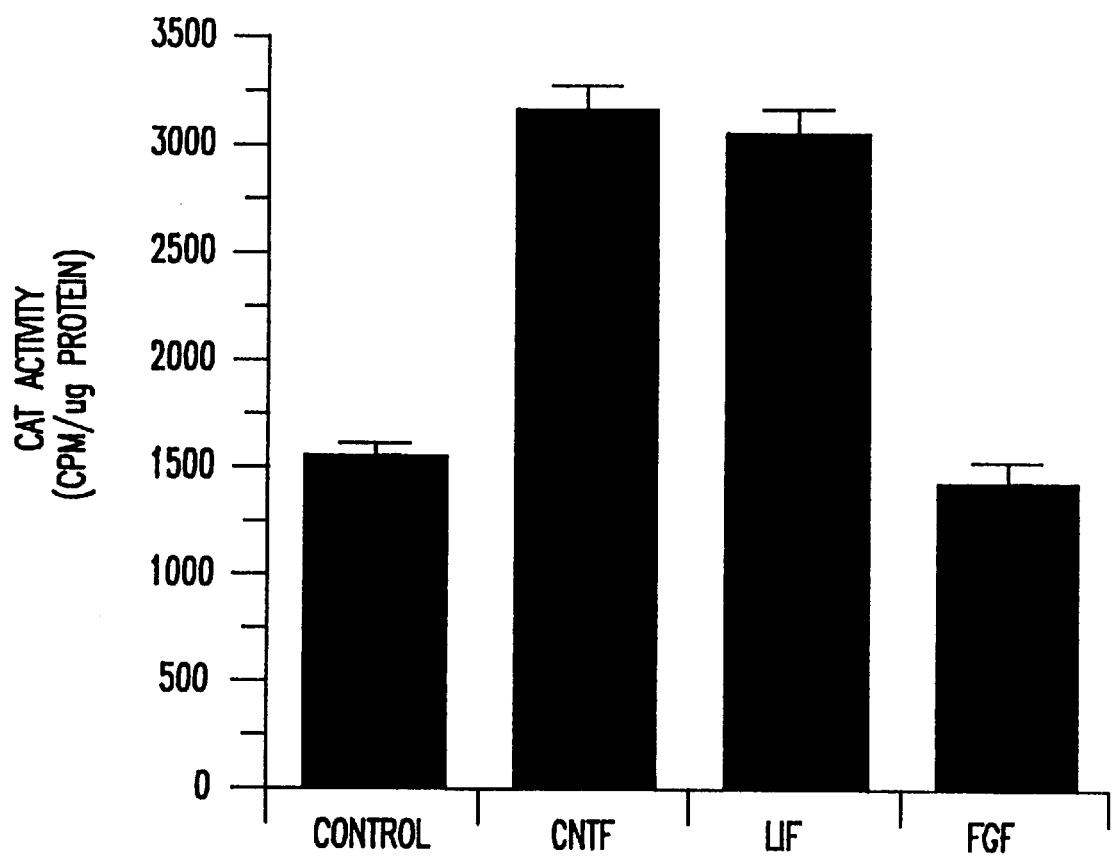
Figure 8B:
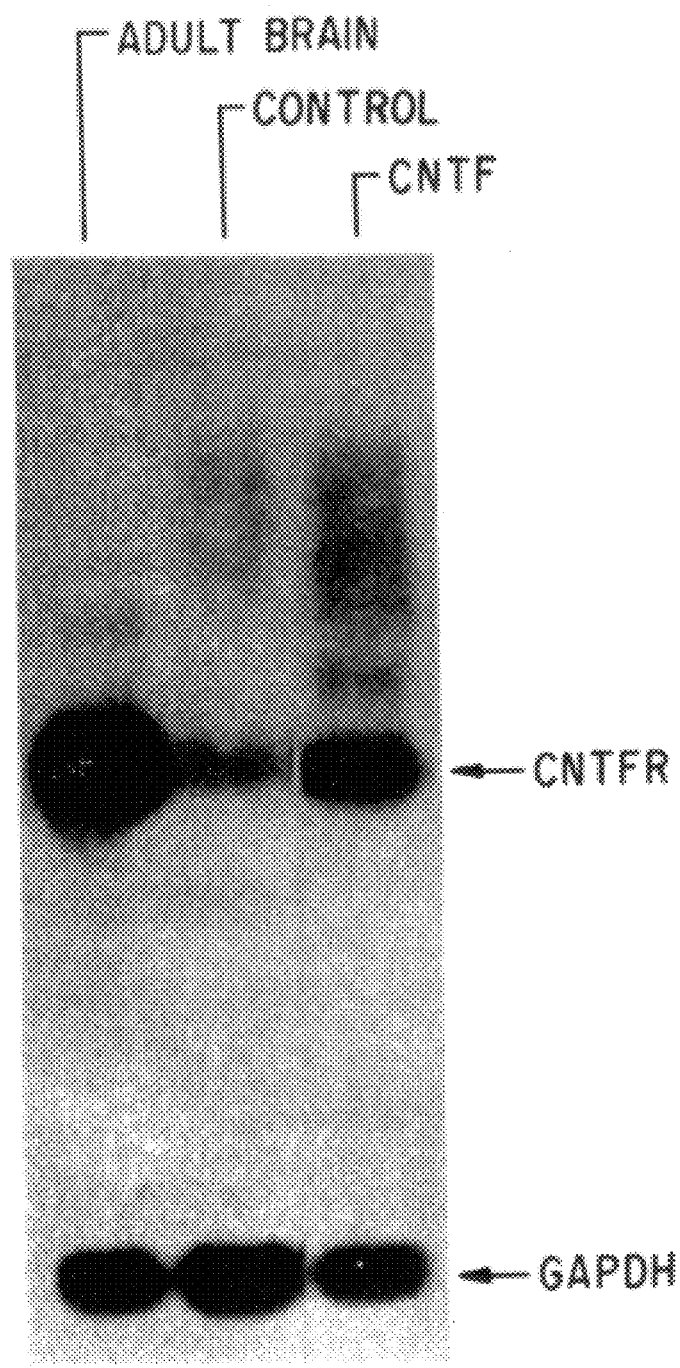

FIGS. 8A and 8B. CNTF affects neuronal differentiation. FIG. 8A. MAH cells were treated with CNTF (10 ng/ml), LIF (1 ng/ml) or FGF (10 ng/ml) for 48 hr, followed by measurement of CAT activity. FIG. 8B. MAH cells were treated with CNTF (10 ng/ml) for 24 hr. Total RNA was prepared and subjected to northern analysis using a CNTFR probe and a GAPDH probe. The transcript sizes for CNTFR and GAPDH were 2 kb.

Figure 9A:
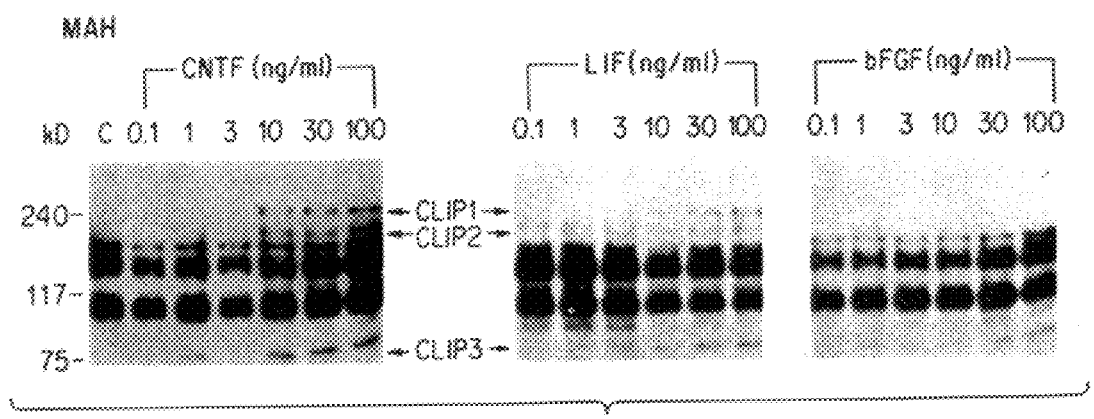
Figure 9B:
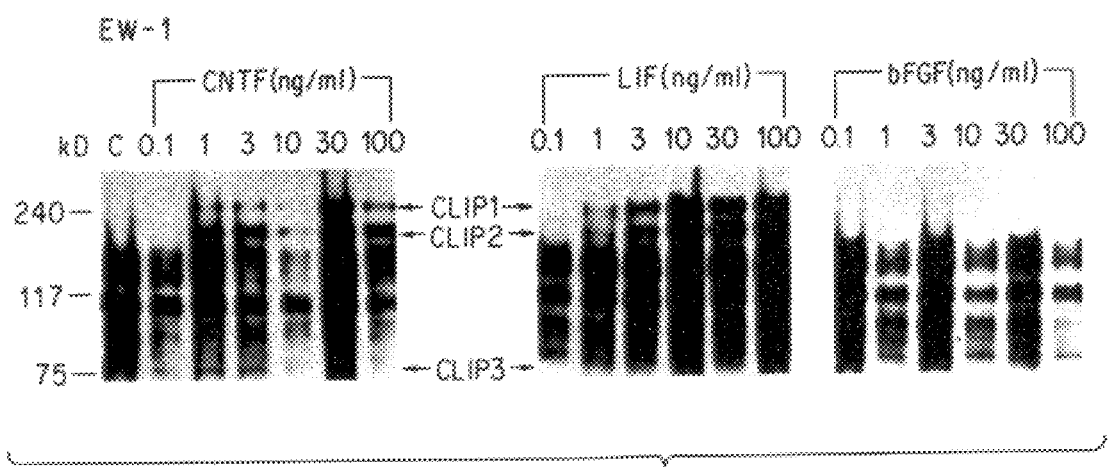
Figure 9C:
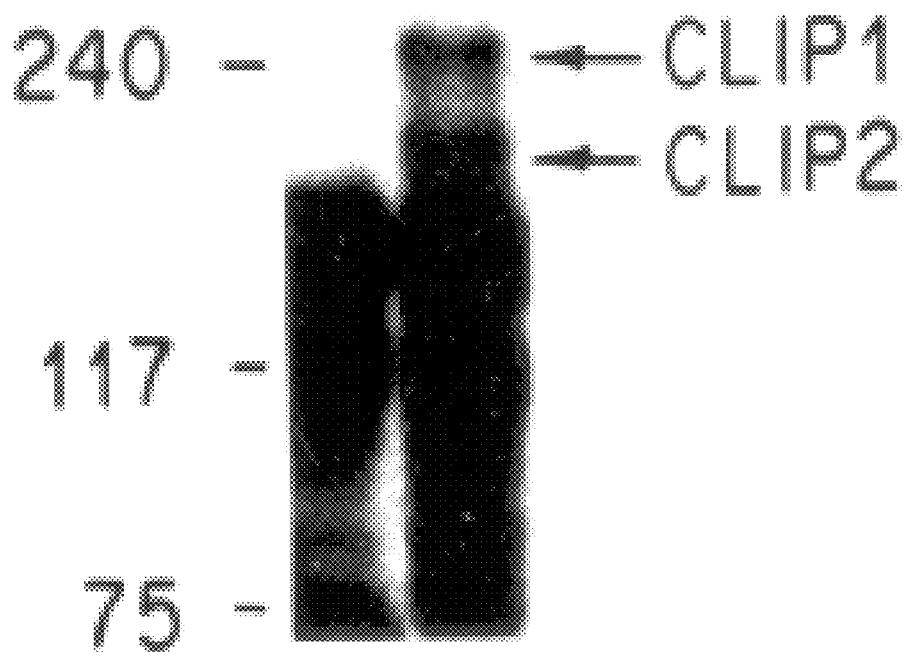

FIGS. 9A–9C. Dose-dependent tyrosine phosphorylation of proteins in response to CNTF, LIF and FGF. Total cell lysates were prepared from MAH cells (FIG. 9A) or EW-1 cells (FIG. 9B) following a 5 min treatment with various concentrations (0.1–100 ng/ml) of CNTF, LIF or FGF. Lysates were immunoprecipitated with anti-phosphotyrosine antibody, electrophoresed and immunoblotted with anti-phosphotyrosine antibody as described in Experimental procedures. (FIG. 9C) SK-N-LO cells were treated with 50 ng/ml of CNTF for 5 or 15 min prior to anti-phosphotyrosine immunoprecipitation and blotting as described above.

Figure 10A:
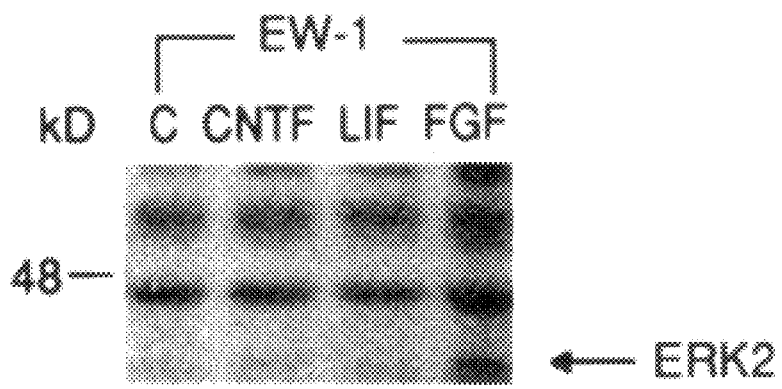
Figure 10B:
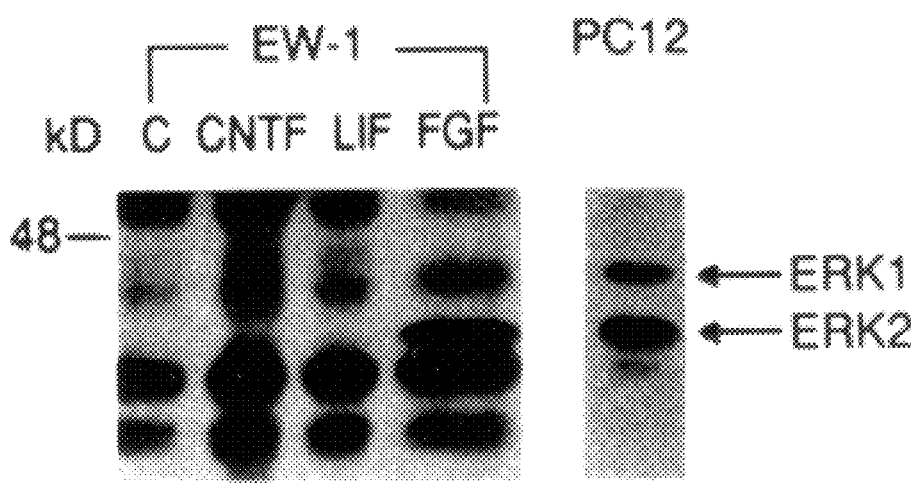
Figure 10C:
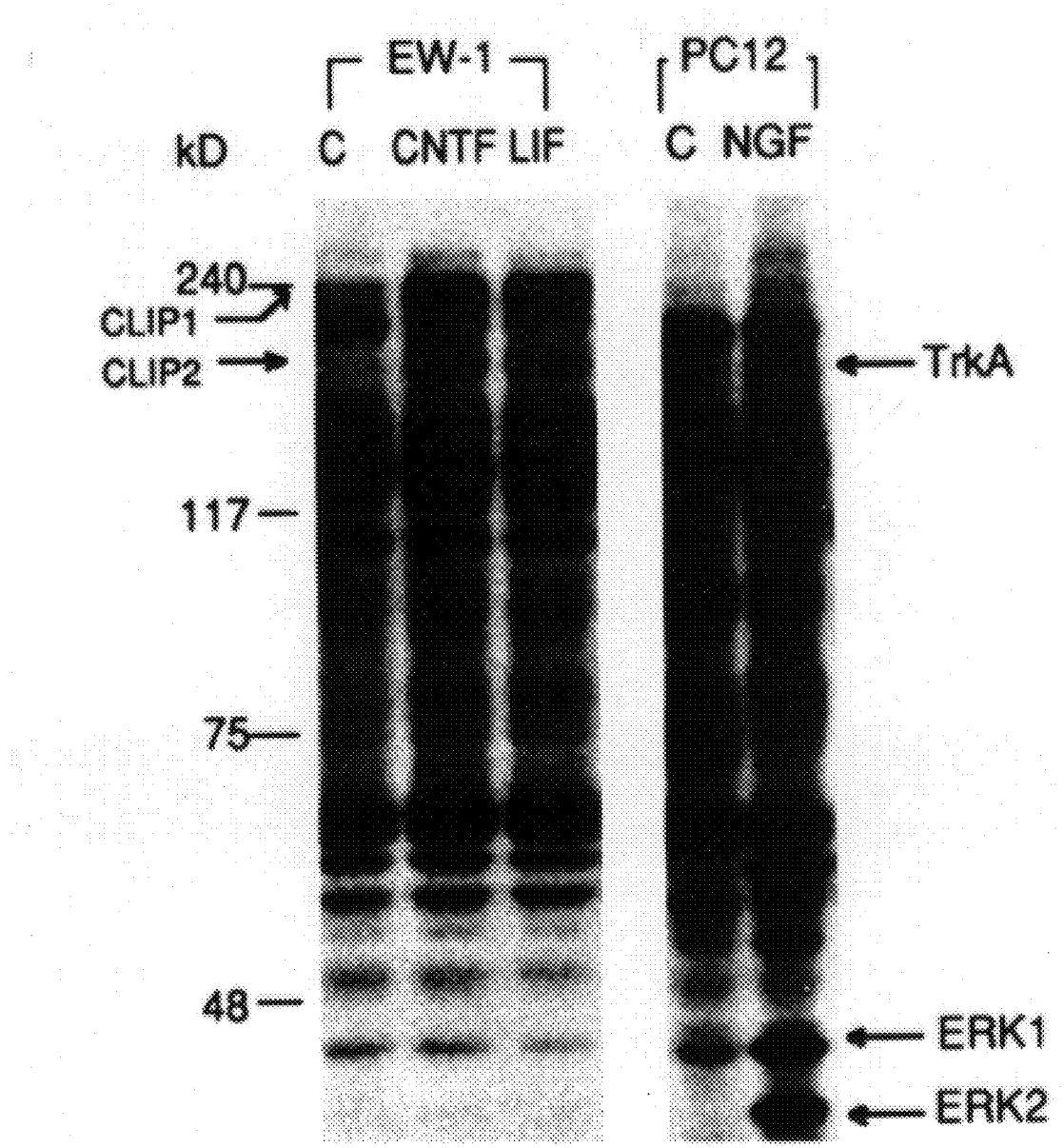

FIGS. 10A–10C. Unique protein tyrosine phosphorylation patterns of CNTF, or LIF treated cells compared to FGF or NGF treated cells. FIG. 10A. EW-1 cells were treated with 50 ng/ml of CNTF, LIF or FGF for 5 min. Total cell lysates were immunoblotted with anti-phosphotyrosine antibody. FIG. 10B. Total cell lysates prepared from EW-1 cells following treatment with 50 ng/ml of CNTF, LIF or FGF were immunoprecipitated using anti-phosphotyrosine antibody. As controls, ERK1 and ERK2 were precipitated from PC12 cell lysates using ERK-specific antibody. Immunoblotting was performed with ERK antibody. FIG. 10C. Total cell lysates were prepared from EW-1 cells treated with CNTF (50 ng/ml) or LIF (50 ng/ml) and PC12 cells treated with NGF (50 ng/ml). Lysates were electrophoresed and immunoblotted with anti-phosphotyrosine antibody.

Figure 11A:
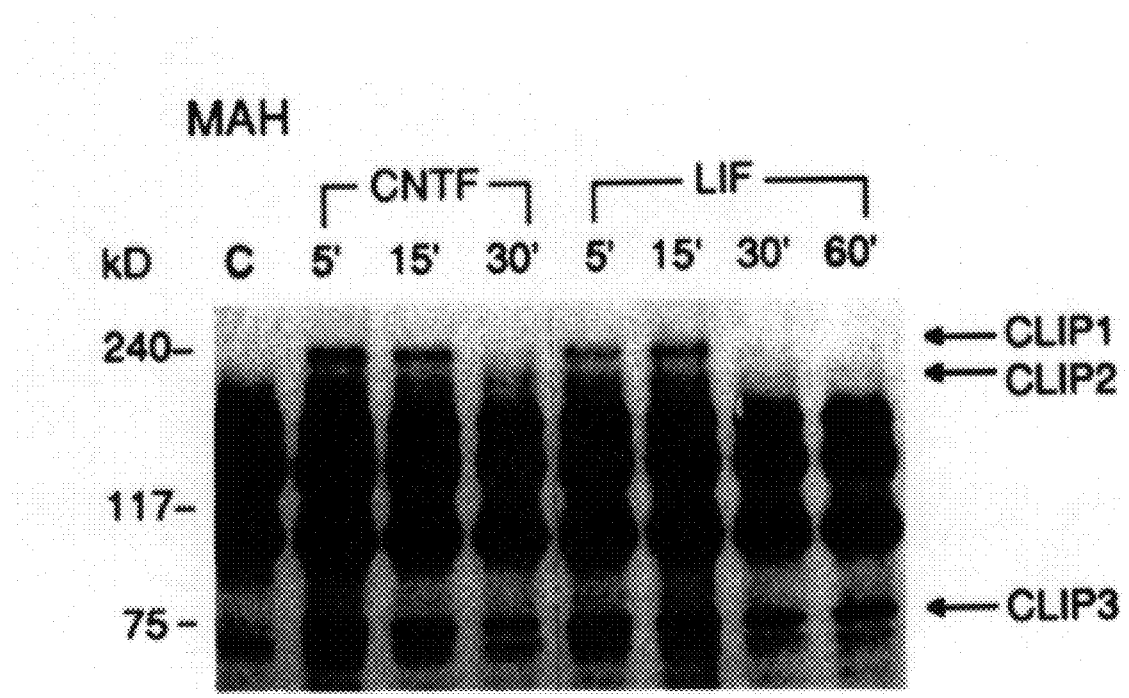
Figure 11B:
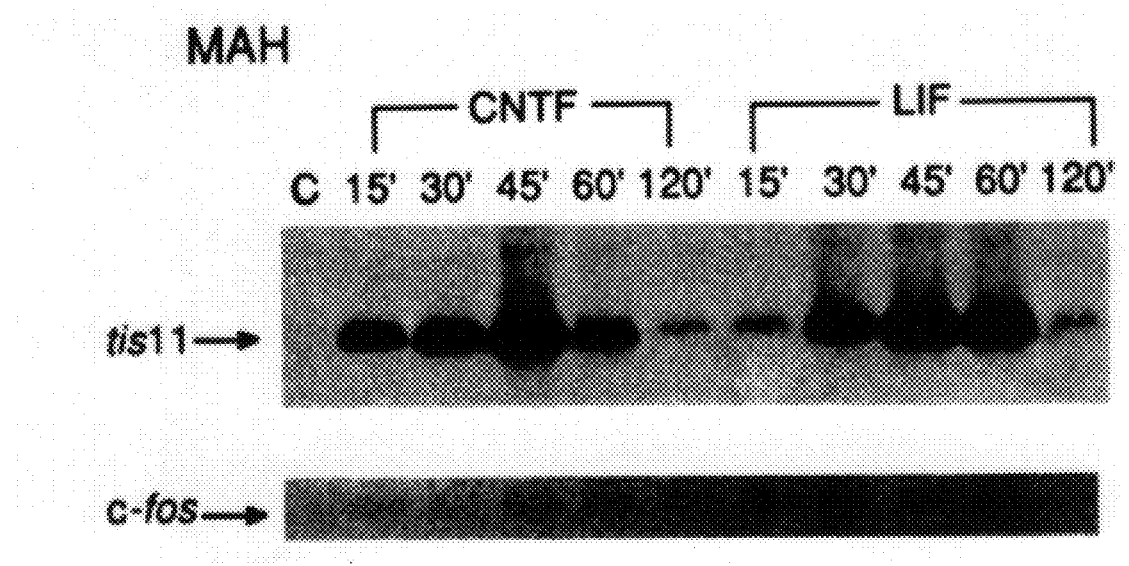
Figure 11C:
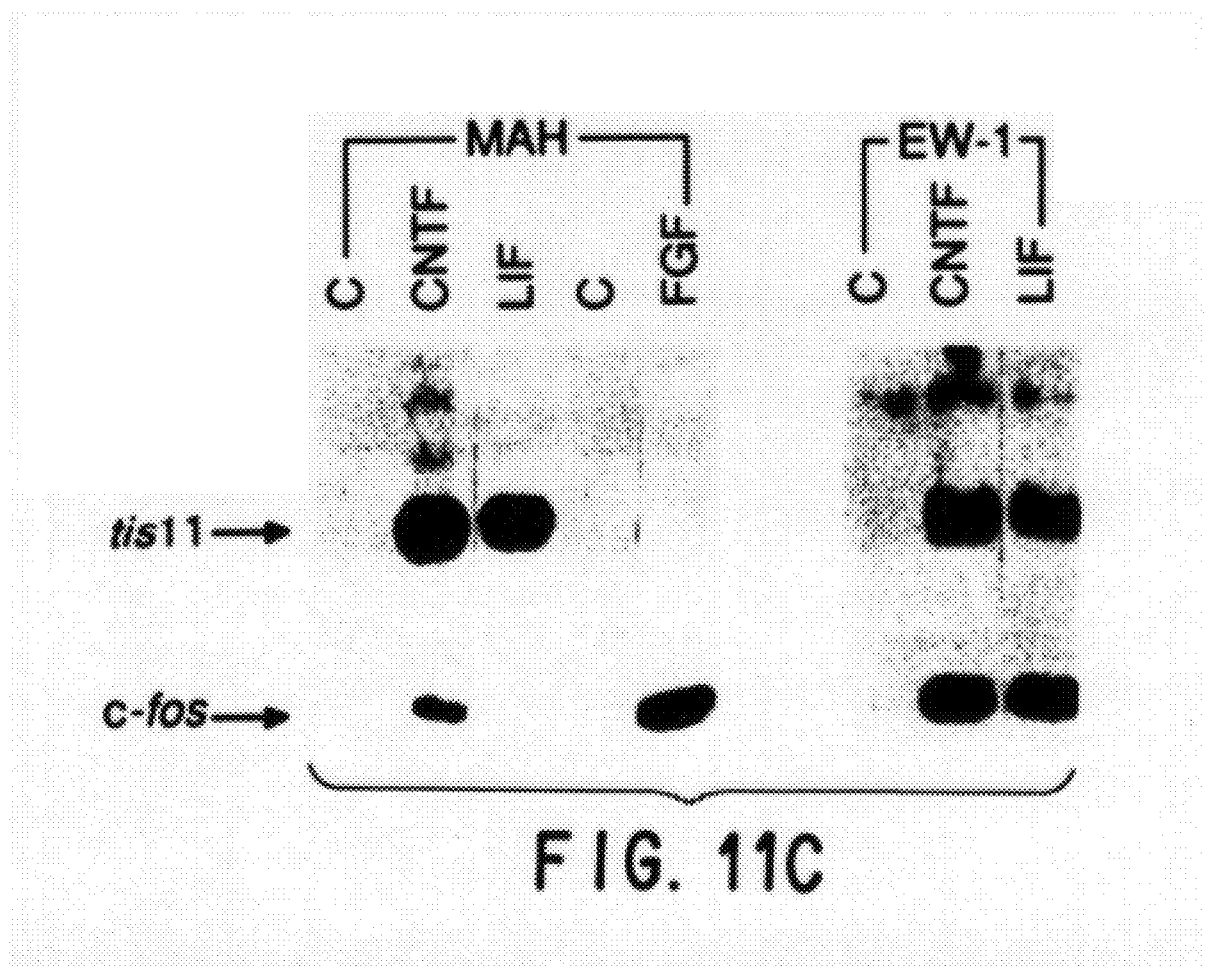

FIGS. 11A–11C. Time course comparison of protein tyrosine phosphorylation changes to tis11 induction in response to CNTF and LIF in MAH cells. FIG. 11A. MAH cells were treated with 50 ng/ml of CNTF or LIF for 5–60 min. Total cell lysates were immunoprecipitated and immunoblotted with anti-phosphotyrosine antibody as described in FIG. 3. FIG. 11B. MAH cells were similarly treated with CNTF or LIF for 15–120 min. Total RNA were prepared, fractionated by formaldehyde agarose gel electrophoresis and hybridized to tis11 and c-fos DNA probes as described in Experimental procedures. FIG. 11C. MAH or EW-1 cells were treated with CNTF (50 ng/ml), LIF (50 ng/ml) or FGF for 30 min. Total RNA were prepared, and expression of tis11 and c-fos were analyzed as above. The transcript sizes for tis11 and c-fos were 2.3 and 2 kb, respectively.

Figure 12:
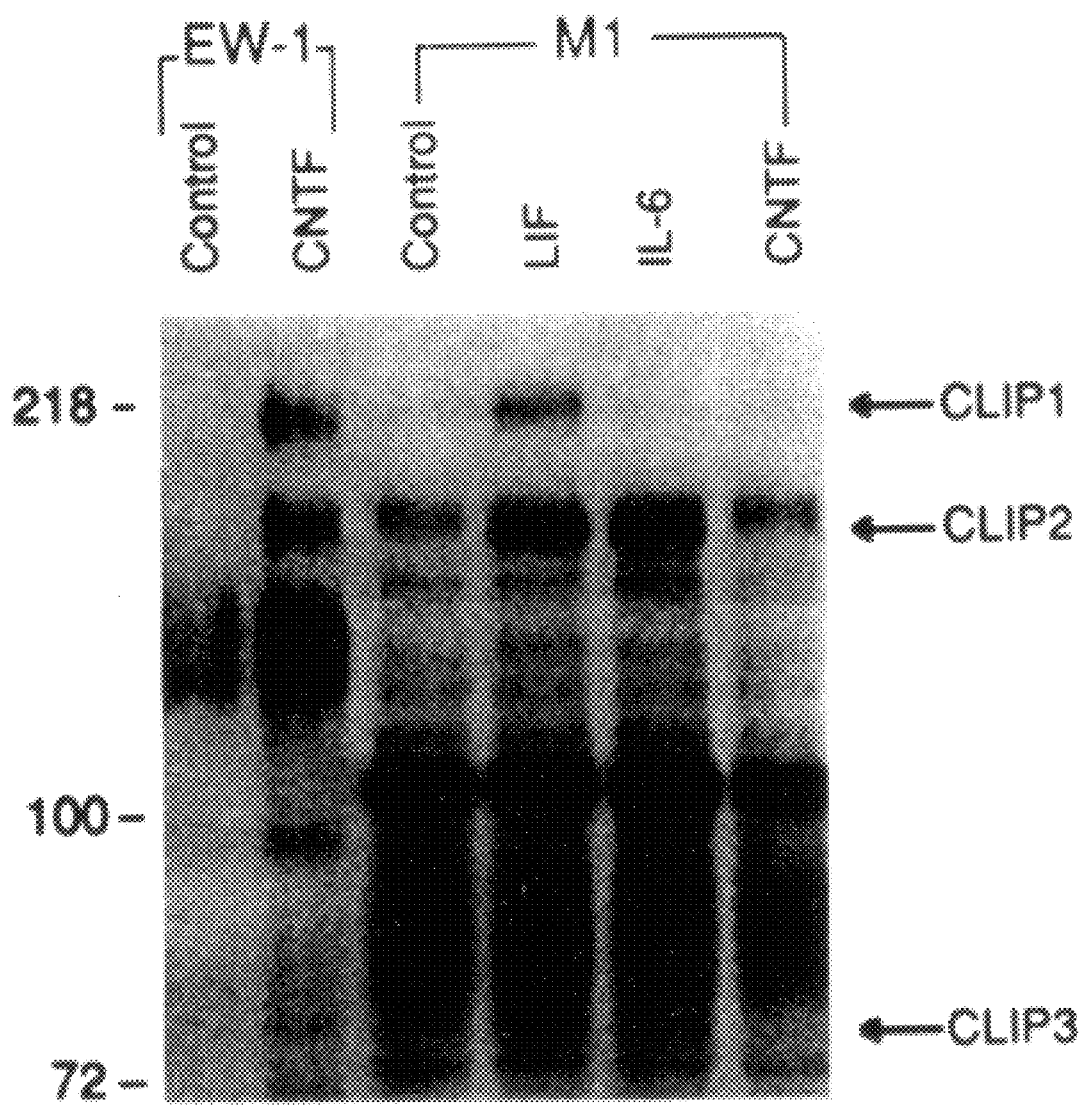
Figure 13A:
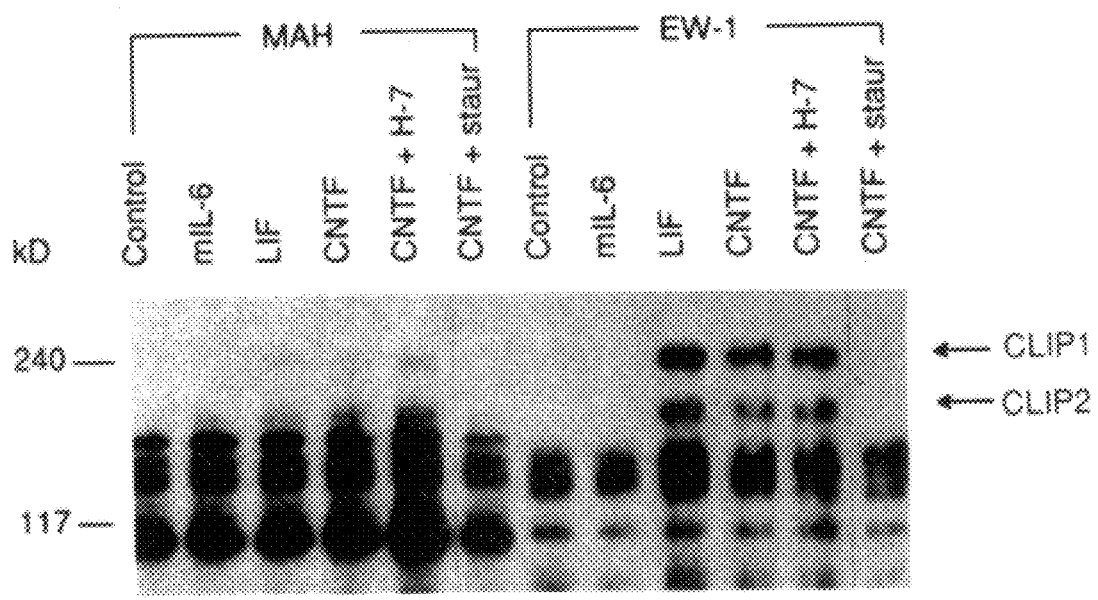
Figure 13B:
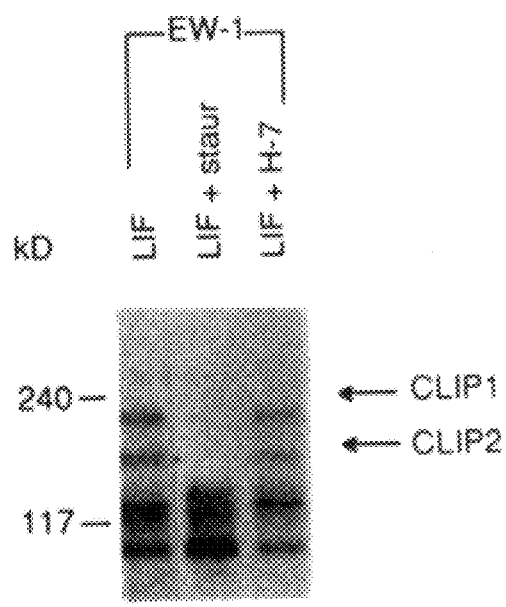
Figure 13C:
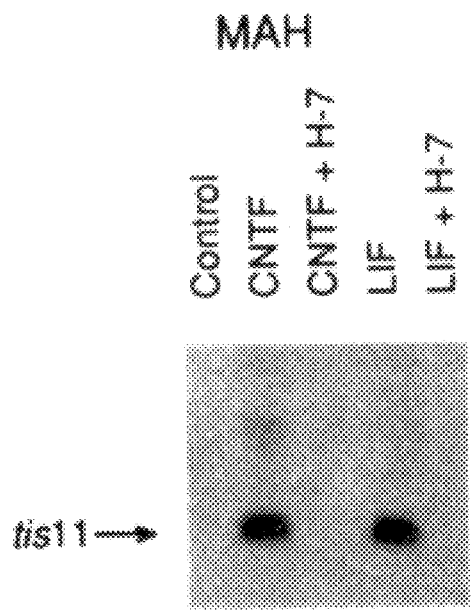
Figure 13D:
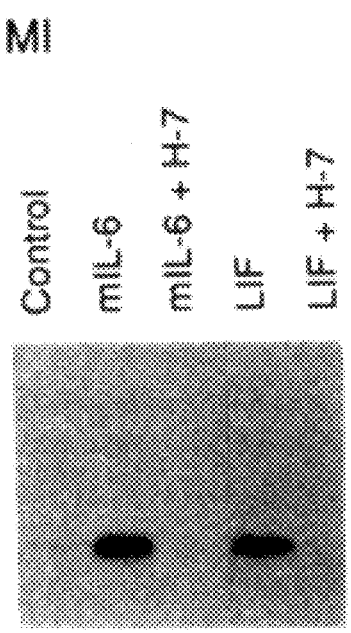

FIG. 12. Comparison of tyrosine phosphorylation changes in response to CNTF, LIF or IL-6 in EW-1 and M1 cells. EW-1 or M1 cells were treated with CNTF (50 ng/ml), LIF (50 ng/ml) or mIL-6 (100 ng/ml) for 5 minutes. Total cell lysates were immunoprecipitated and immunoblotted with antiphosphotyrosine antibody as described supra.

FIGS. 13A–13D. Effects of protein kinase inhibitors on CNTF- and LIF-induced protein tyrosine phosphorylation and tis11 gene expression MAH (FIG. 13A) or EW-1 (FIG. 13B) cells were treated with protein kinase inhibitors H-7 (40 ug/ml) or staurosporine (100 ng/ml) for 15 minutes prior to addition of CNTF (50 ng/ml), LIF (50 ng/ml) or mIL-6 (100 ng/ml). Total cell lysates were immunoprecipitated and immunoblotted with anti-phosphotyrosine antibody as described supra. To examine the effects of protein kinase inhibitor on tis11 induction, MAH(FIG. 13C) or M1(FIG. 13D) cells were treated with protein kinase inhibitors H-7 (40 ug/ml) for 30 min prior to addition of CNTF (50 ng/ml), LIF (50 ng/ml) or mIL-6 (100 ng/ml). Total RNA were prepared and subjected to northern analysis using a tis11 probe.

Figure 14A:
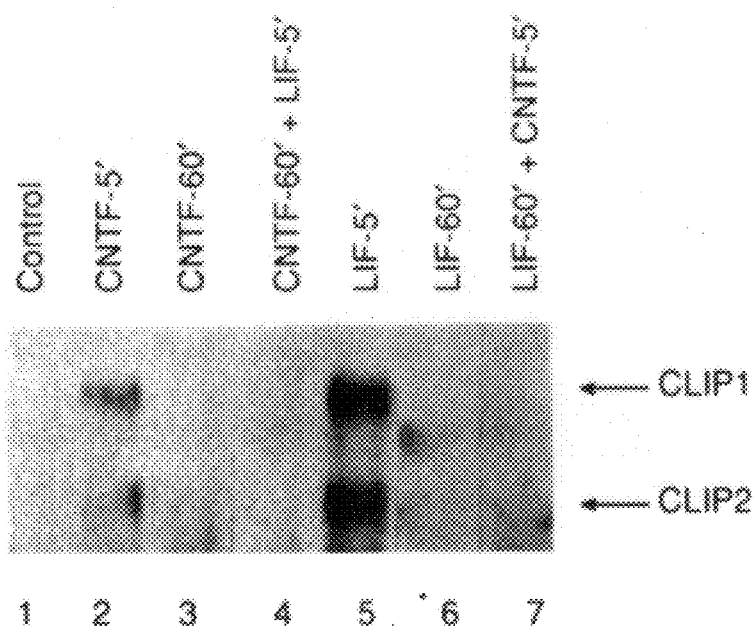
Figure 14B:
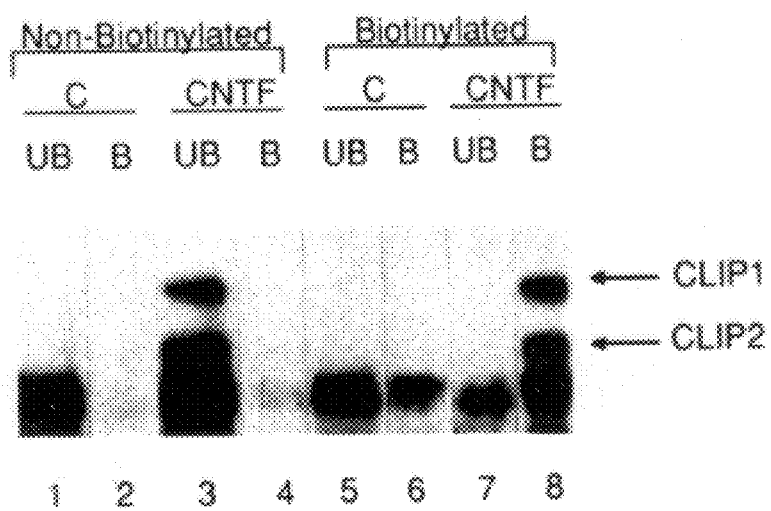
Figure 14C:
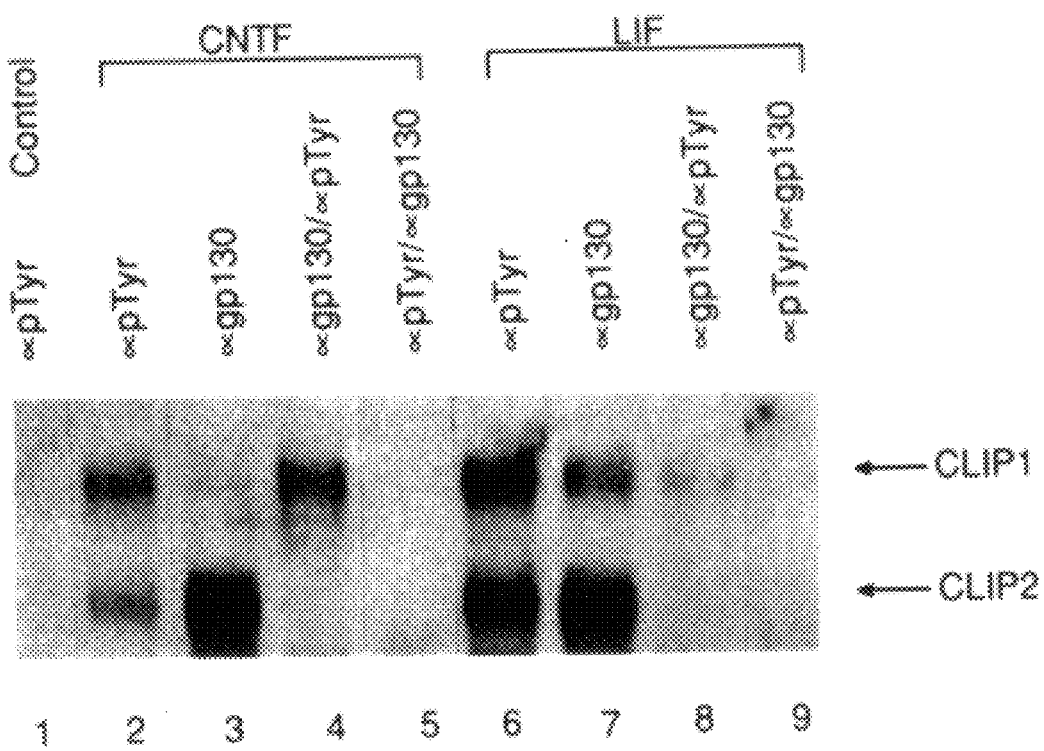

FIG. 14. The CLIPs are co-regulated by CNTF and LIF (FIG. 14A), are on the cell surface (FIG. 14B), and one of the CLIPs (CLIP2) is gp130. FIG. 14A. CLIP1 and CLIP2 are co-regulated by CNTF and LIF. EW-1 cells were treated for five or 60 minutes with either CNTF (50 ng/ml) or LIF (50 ng/ml), as indicated; after the 60 minute timepoints either additional CNTF (lanes 3 and 7) or LIF (lanes 4 and 6) were added to the cells for five additional minutes. Total cell lysates were then immunoprecipitated and immunoblotted with anti-phosphotyrosine antibody. FIG. 14B. Biotinylation assay reveals that CLIP1 and CLIP2 are on the cell surface. EW-1 cells were surface biotinylated as described herein. The figure shows the anti-phosphotyrosine immunoblot for control (FIG. 14C) or CNTF stimulated (CNTF) cells that were subsequently biotinylated or left non-biotinylated before separation into unbound (UB) or bound (B) fractions on streptavidin-agarose. C. CLIP2 is gp130. The figure shows the anti-phosphotyrosine immunoblot of lysates from control (C) or CNTF/LIF stimulated EW-1 cells that were immunoprecipitated with the anti-phosphotyrosine antibody (αpTyr) or the gp130-specific antibody (αgp130). The immunoprecipitating antibodies were either used individually or in sequential manner, as indicated.

Figure 15:
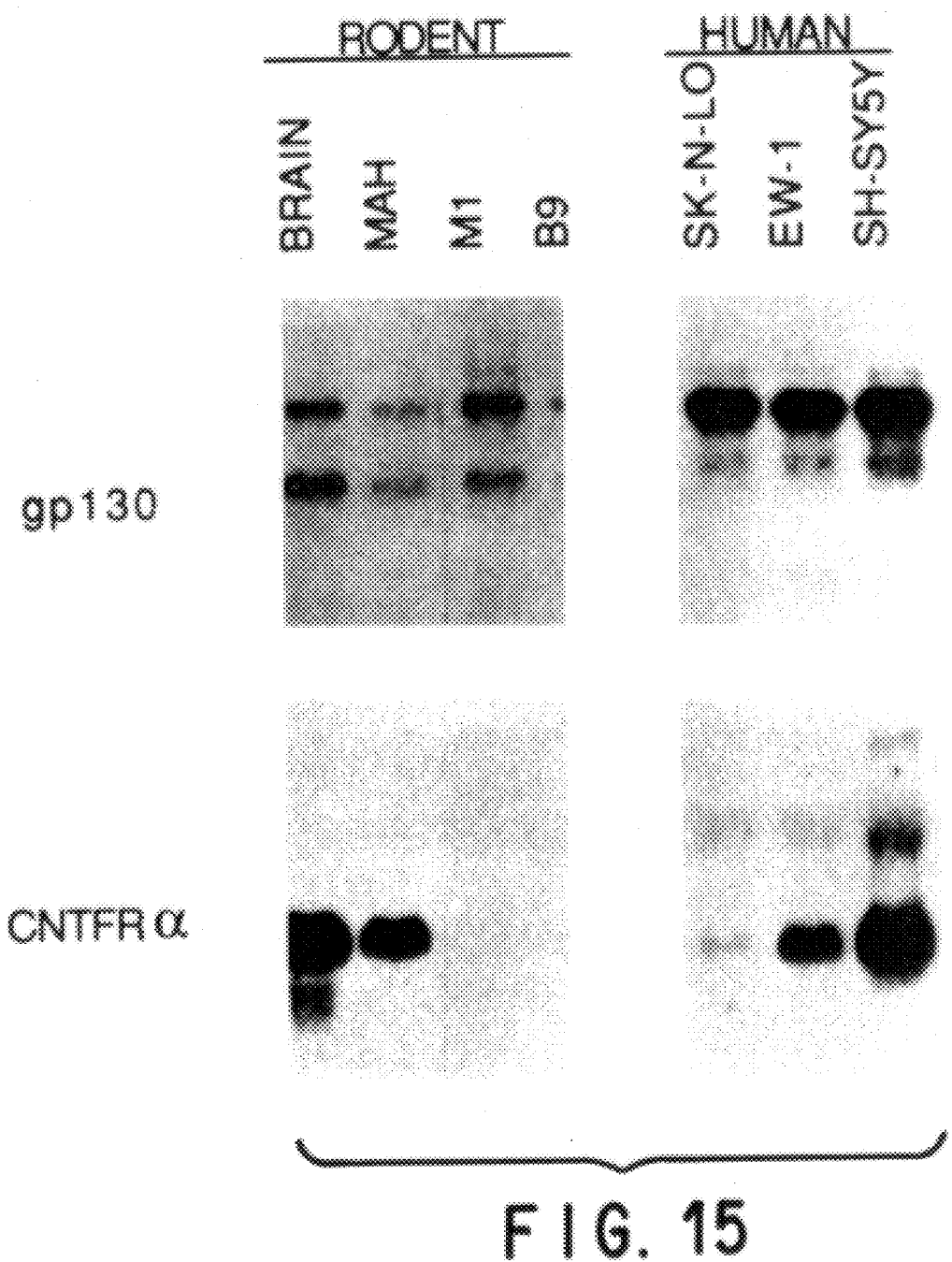

FIG. 15. Ubiquitous distribution of gp130 mRNA contrasts with restricted neuronal distribution of CNTFRα mRNA. Total RNA was prepared from the indicated lines and subjected to northern analysis using either a human gp130 cDNA probe (top panels), or a rat CNTFR cDNA probe (bottom panels); the weaker hybridization to the rodent lines with the gp130 probe is due to poor cross-species hybridization. SH-SY5Y, neuroblastoma; EW-1, ewing's sarcoma; SK-N-LO, neuroepithelioma; MAH, sympathoadrenal progenitor; M1, myeloid progenitor; B9, IL-6 dependent B cell hybridoma that does not respond to CNTF.

Figure 16:
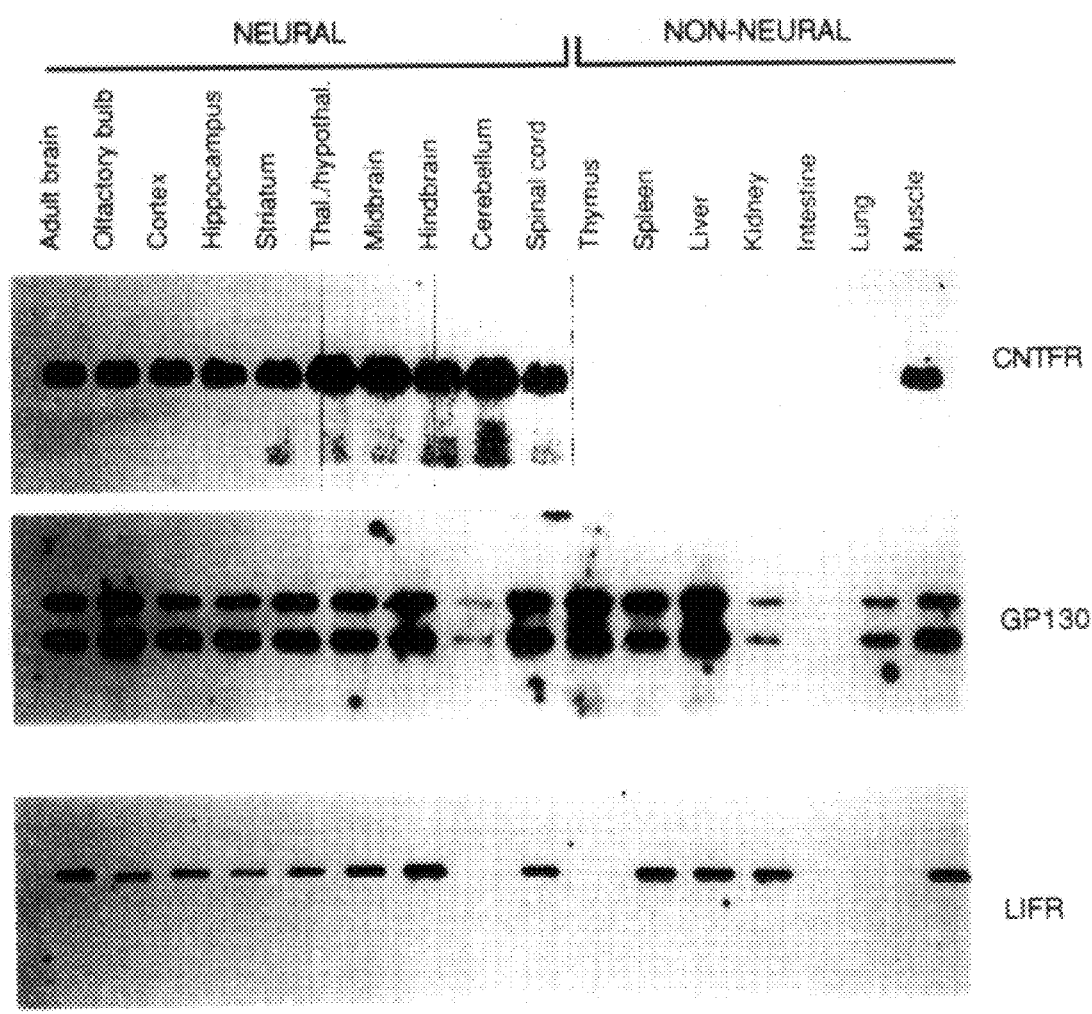

FIG. 16. Ubiquitous distribution of gp130 mRNA in tissues. Total RNA and northern analysis was conducted as in FIG. 15.

Figure 17A:
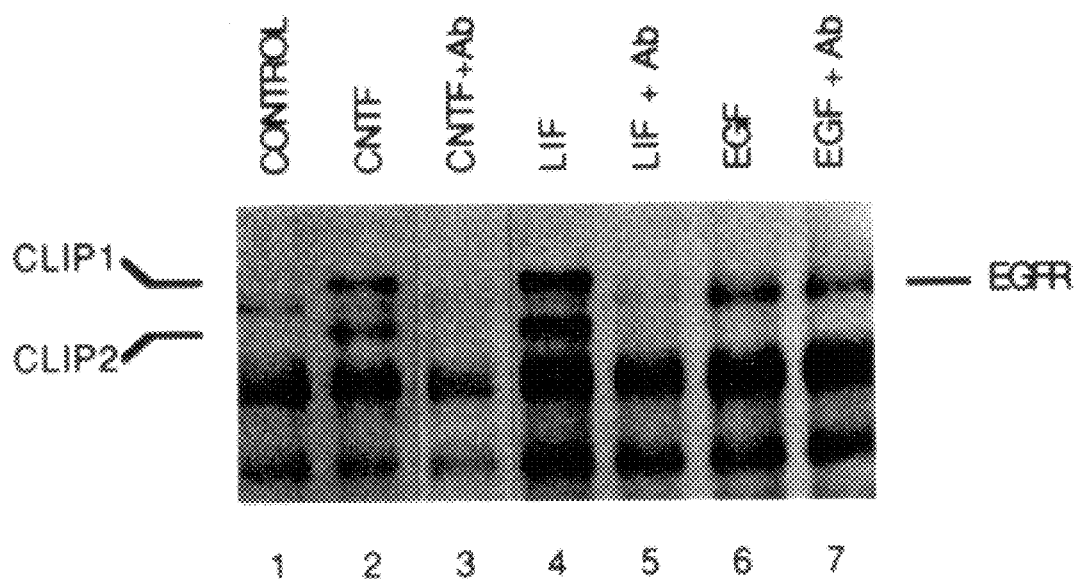
Figure 17B:
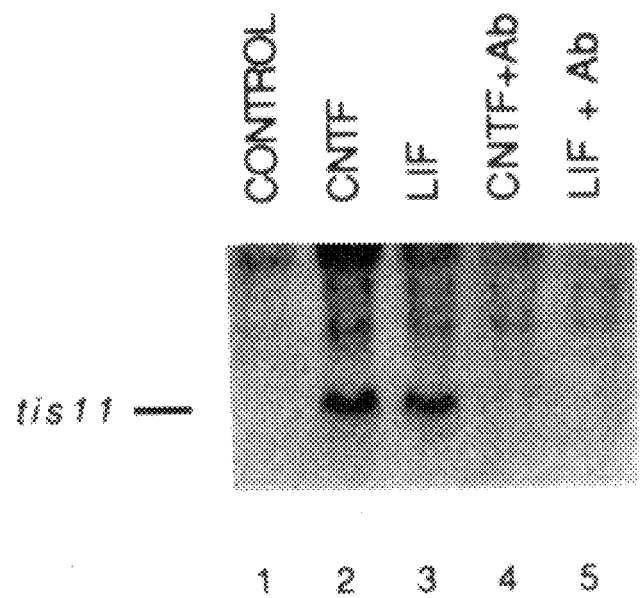

FIGS. 17A–B. gp130 blocking antibodies prevent CNTF/LIF induced tyrosine phosphorylations and gene inductions. Antibodies were examined for their ability to block tyrosine phosphorylations induced by CNTF and LIF in EW-1 cells. Tyrosine phosphorylations of CLIP 1 and CLIP2 (FIG. 17A), as well as tis 11 gene expression induced by CNTF or LIF (FIG. 17B) were both completely blocked by anti-gp130.

Figure 18A:
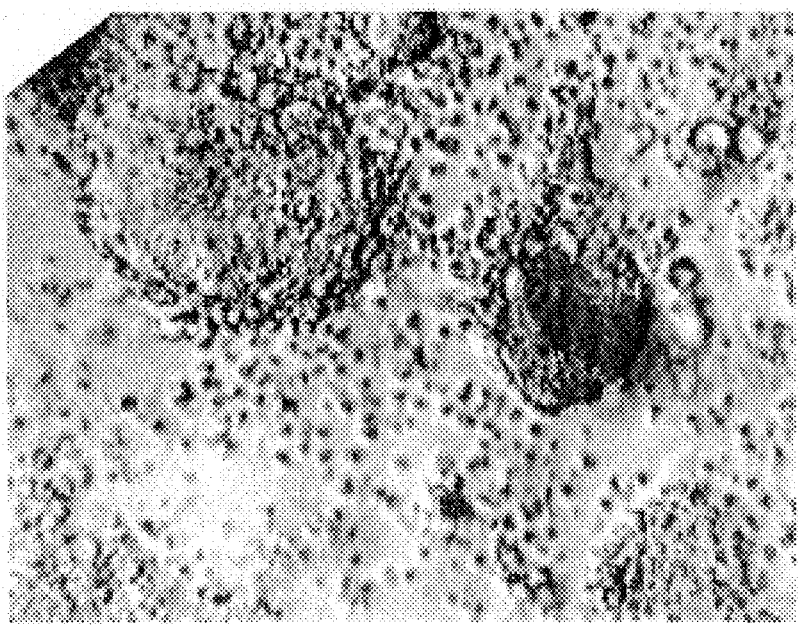
Figure 18B:
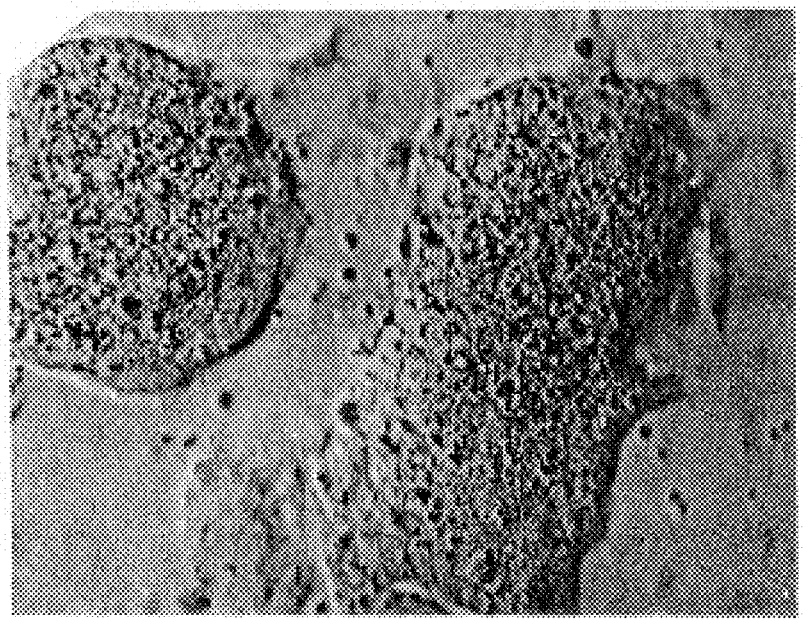
Figure 18C:
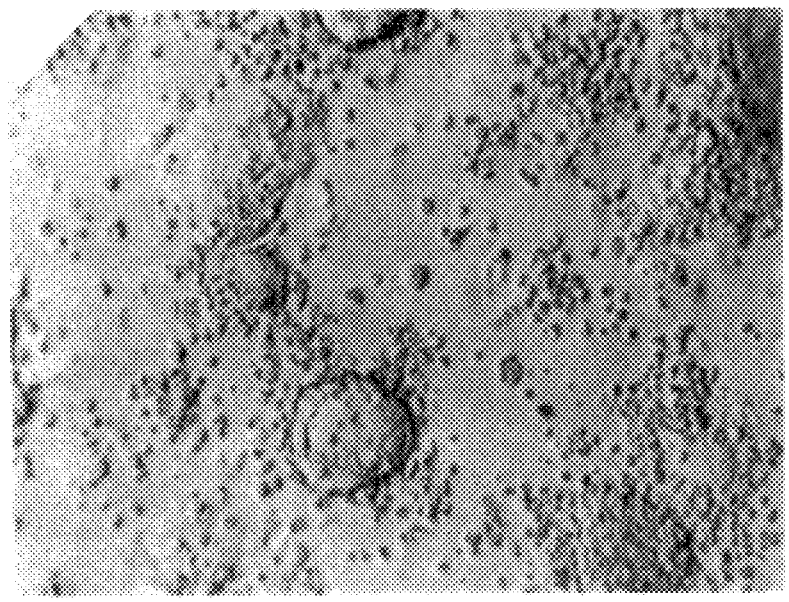
Figure 18D:
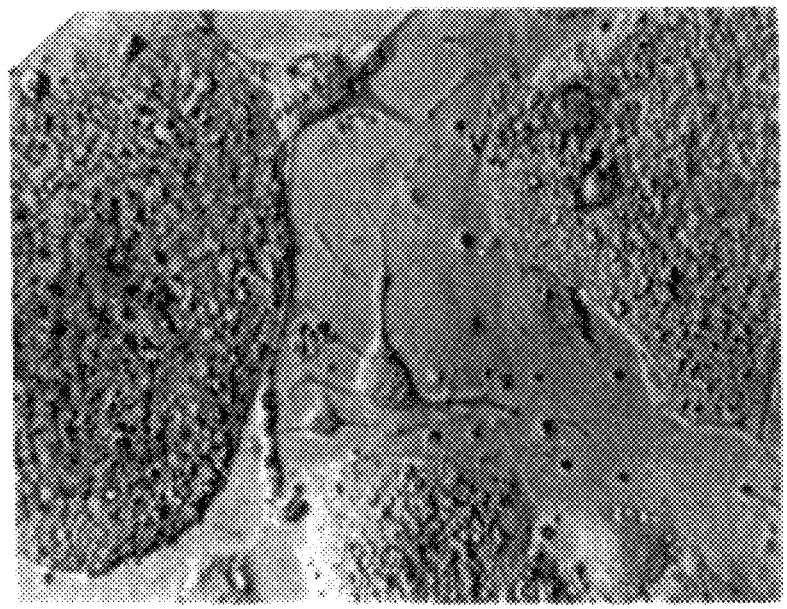

FIGS. 18A–18D. Effect of LIF and CNTF on ES cells. ES cells maintained in the absence of feeder cells, but in the presence of LIF (10–20 ng/ml) remained as undifferentiated, compact colonies of small cells. Lower concentrations of LIF (less than 10 ng/ml) resulted in the differentiation of the ES cells over a period of 2–7 days, as evidenced by the presence of endoderm-like cells and large, flat cells, with some cell death occurring (FIG. 18A). ES cells grown on gelatin plates with 5 pg/ml to 10 ng/ml CNTF, resulted in differentiation and some cell death. Concentrations of CNTF greater than 10 ng/ml up to 50 ng/ml CNTF maintained ES cells as small compact colonies of cells (FIG. 18B). ES cells maintained in the absence of either LIF or CNTF appeared endoderm-like or large and flat over a period of 2–7 days (FIG. 18C).

Figure 19:
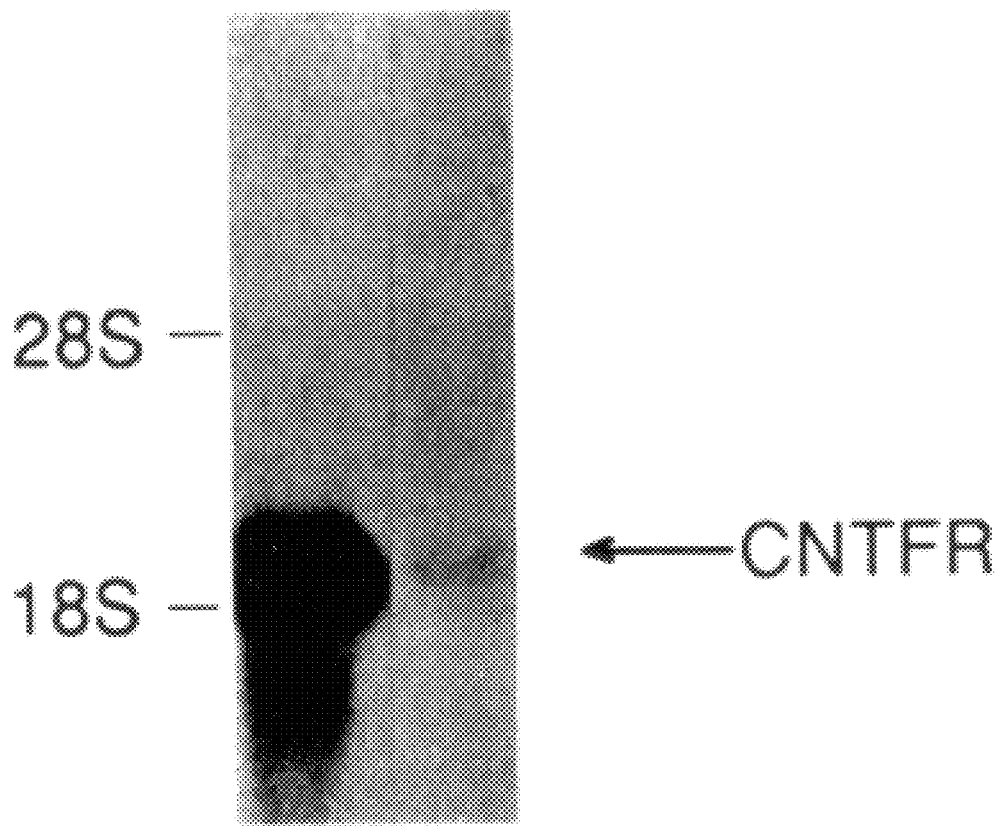

FIG. 19. Expression of CNTFR in ES cells. Northern analysis of RNA from ES cells and rat brain indicating expression of CNTFR.

Figure 20A:
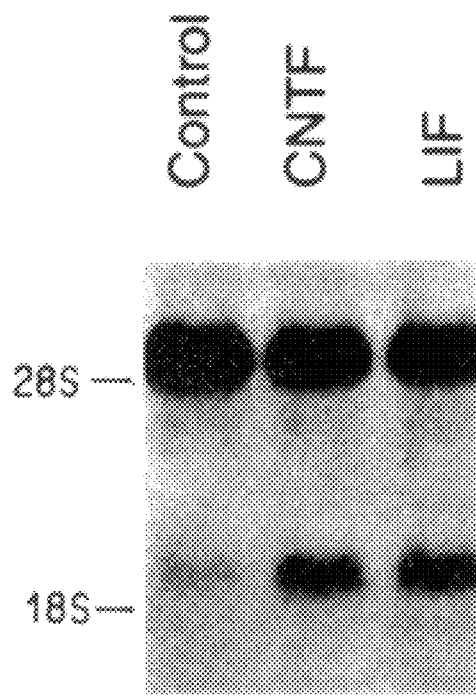
Figure 20B:
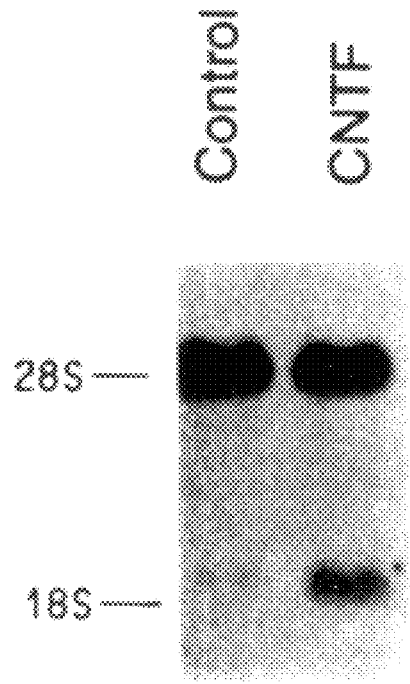

FIGS. 20A and 20B. Induction of tis II by CNTF and LIF in ES cells. ES cells were plated and maintained in an undifferentiated state in the presence of either CNTF (20 ng/ml) or LIF (20 ng/ml). Total cellular RNA was prepared, electrophoresed on a formaldehyde agarose gel, transferred to nylon membrane and hybridized to $^{32}$P-labelled tis11 probe. In ES cells, CNTF and LIF both produced similar inductions in tis11 gene expression.

Figure 21B:
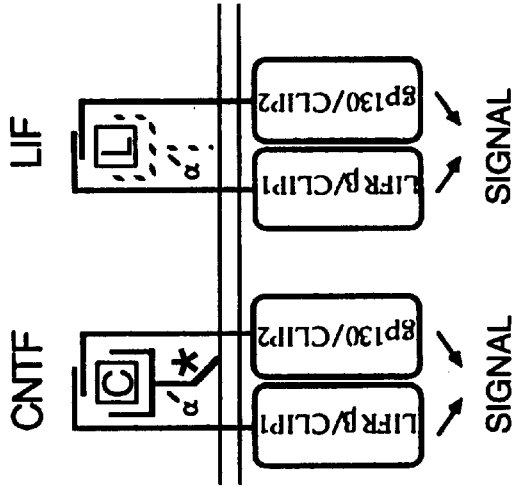
Figure 21A:
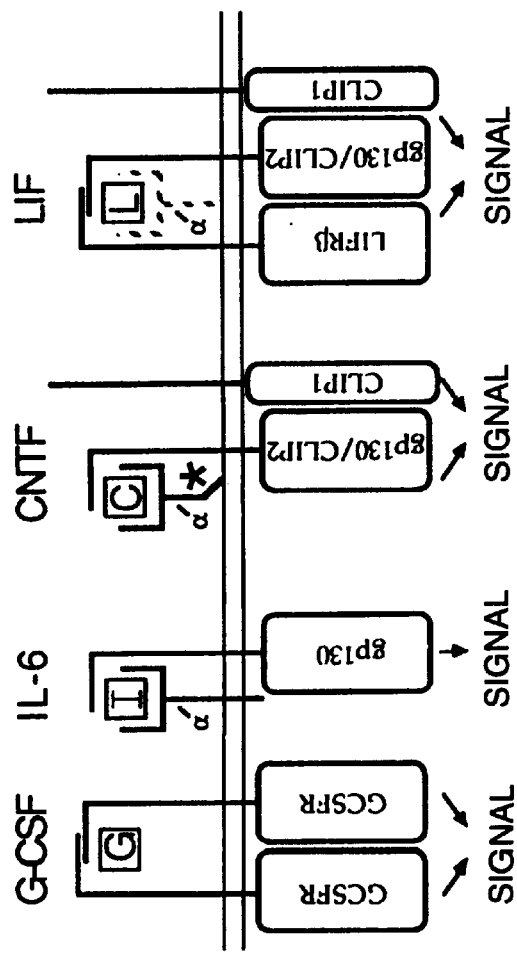

FIGS. 21A and 21B. Schematic models of G-CSF, IL-6, CNTF and LIF receptor complexes. FIG. 21A. Model depicting known components of indicated cytokine receptor complexes. FIG. 21B. Revised "unified" models of CNTF and LIF receptor complexes assuming that CLIP1 is LIFRβ. In the model presented in part FIG. 21B, CNTFRα is all that is required to convert a functional LIF receptor complex into a functional CNTF receptor complex. Factors represented as squares; α subunits are known to exist for the IL-6 and CNTF receptor complexes, and are thus depicted with solid lines (asterisk adjacent to CNTFRα/membrane junction indicates GPI-linkage), while potential LIFRα component is indicated by a dashed line. Although depicted as membrane bound, a subunits may also function as soluble co-factors.

Figure 22:
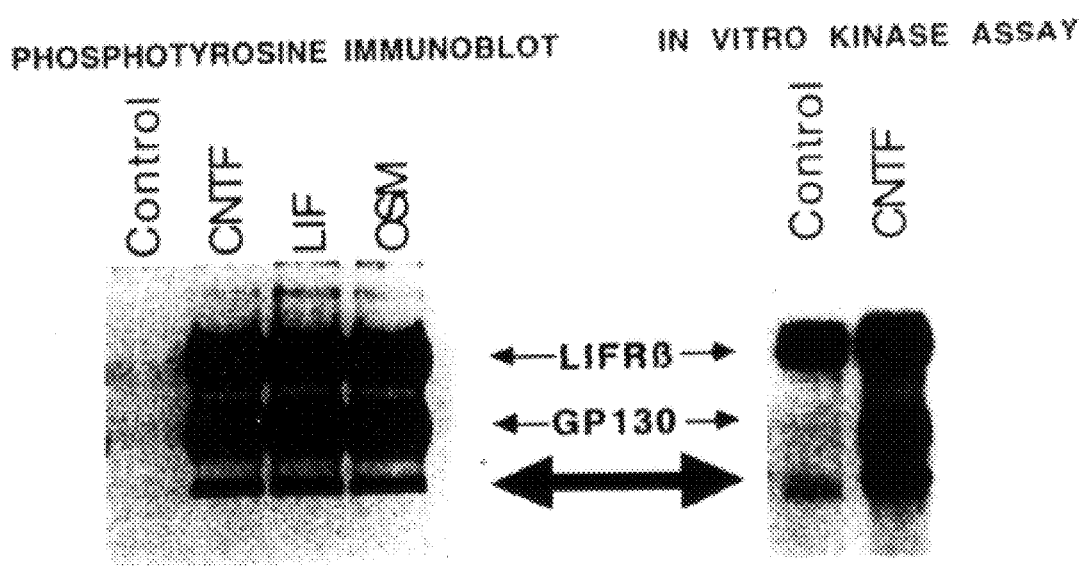

FIG. 22: A 130 kDa protein and tyrosine kinase activity copurify with CNTF receptor complexes. EW-1 cells were stimulated with the indicated factor, then the cells were lysed in Brij 96 detergent and immunoprecipitated with α-LIFRb. Samples in the left panel were immunoblotted with a-phosphotyrosine, while those in the right were tested for in vitro kinase activity as described in the Experimental section.

FIGS. 23A–23D: Jak1, Jak2, and Tyk2 become tyrosine phosphorylated in response to the CNTF family of factors. Either EW-1 (FIGS. 23A and 23B), U266 (FIG. 23C), or SK-MES cells (FIG. 23D) were stimulated with the indicated factor, immunoprecipitated with antisera against LIFRβ, Jak1 (J1), Jak2 (J2), or Tyk2 (T2), then immunoblotted with anti-phosphotyrosine.

Figure 24:
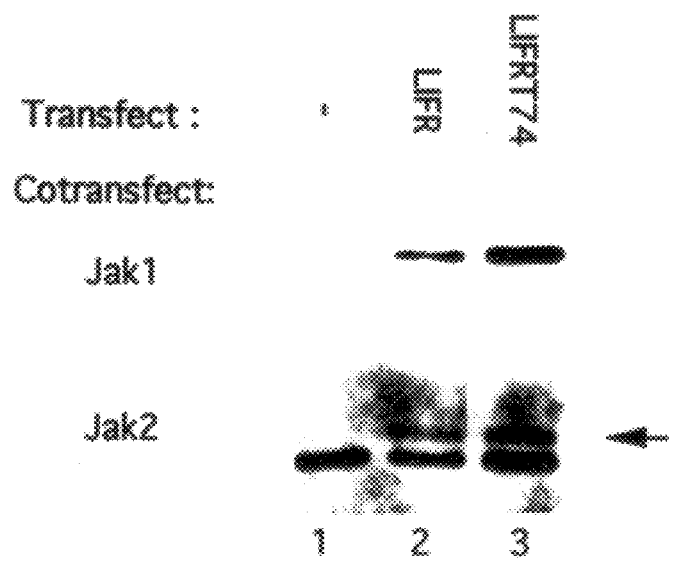

FIG. 24: LIFRβ binds Jak1 and Jak2 in the absence of factors. COS cells were cotransfected with plasmids encoding Jak1 or Jak2, along with those encoding either epitope-tagged LIFRβ-myc3 (LIFR) or a truncated version of LIFRβ, encoding only 74 amino acids of the cytoplasmic domain followed by the triple-myc tag. (LIFRT74). Following immunoprecipitation with the a-myc monoclonal 9E10, the samples were immunoblotted with antisera against Jak1 (top panel) or Jak2 (lower panel). The arrow in the bottom panel indicates the Jak2 band which migrates more slowly than the prominent nonspecific background band.

Figure 25:
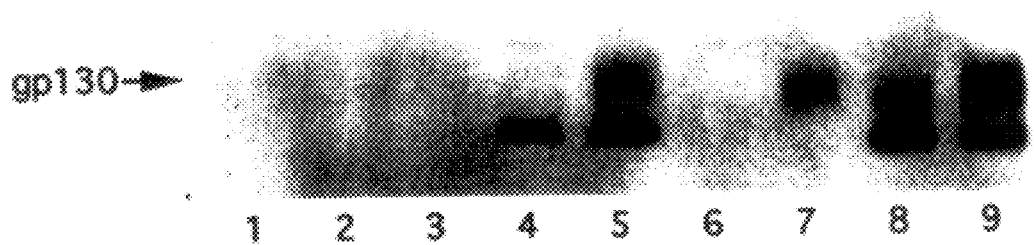

FIG. 25: Coexpression of either Jak1 or Jak2 with gp130 in COS enhance IL-6 dependent tyrosine phosphorylation of gp130. COS cells were cotransfected with 0.5 mg of Jak1 or Jak2 encoding plasmid as well as 10 mg of gp130FLAG encoding plasmid, then stimulated 48 hours later with IL6+ sIL6Rα as indicated. Cell lysates were immunoprecipitated with a-FLAG monoclonal antibodies (IBI), and immunoblotted with anti-phosphotyrosine.

5. DETAILED DESCRIPTION OF THE INVENTION

The present invention relates to a cell free CNTF/receptor complex and related compounds and their use in promoting the survival, differentiation, proliferation and/or growth of cells which may or may not express CNTFR. For purposes of clarity of disclosure, and not by way of limitation, the detailed description of the invention is divided into the following subsections:

(i) the CNTF/Receptor Complex.
(ii) characteristics of the CNTF/Receptor Complex; and
(iii) uses of the CNTF/Receptor Complex The present invention is based on the further discoveries that CNTF and LIF act on neuronal cells via a shared signalling pathways that involves the IL-6 signal transducing receptor component gp130 and that CNTF and LIF require a second, CLIPI/LIFRβ component to initiate signal transduction. It is also based on the discovery that these cytokines that share receptor components utilize shared signal transducing components. Thus, the detailed description of the invention is further divided into the following subsections:

(iv) CNTF, IL-6 and LIF Share Signal Transducing Components (v) uses of Shared and Unique Signal Transducing Components.

5.1 THE CNTF/RECEPTOR COMPLEX

The present invention relates to the formation of a stable, biologically active cell-free CNTF/receptor complex. It is based, in part, on the production and purification of useful amounts of CNTF and CNTFR and their ability to form a stable, biologically active complex under normal physiological conditions.

For example, useful amounts of CNTF and CNTFR may be prepared by first cloning and sequencing a gene encoding each respective protein. Each cloned gene may then be expressed in a prokaryotic or eukaryotic expression system. Any of a number of protocols available to one skilled in the art may be utilized to clone and sequence CNTF and CNTFR. For example, but not by way of limitation, CNTF may be cloned and sequenced preceding expression in a bacterial expression system, as described in U.S. patent application Ser. No. 07/570,651, entitled "Ciliary Neurotrophic Factor," filed Aug. 20, 1990 by Sendtner, et al., International Application No. PCT/US 90/05241, published as WO 91/04316 on Apr. 4, 1991, which are incorporated in their entirety by reference herein. In addition, CNTFR may, by way of example and not of limitation, be cloned and sequenced, as described in U.S. patent application Ser. No. 07/700,677, entitled "The Ciliary Neurotrophic Factor," filed May 15, 1991 by Davis, et al., now abandoned, refiled Jan. 11, 1996 as U.S. Ser. No. 08/585,258 now allowed, and International Application No. PCT/US 91/03896 by Davis et al., filed Jun. 3, 1991 published as WO91/19009 on Dec. 12, 1991. In preferred embodiments, CNTF having a sequence substantially as set forth in FIGS. 1A and 1B and CNTFR having a sequence substantially as set forth in FIGS. 2A–2D may be used.

The recombinant CNTFR gene may be expressed and purified utilizing any number of methods. In a preferred, nonlimiting embodiment of the invention, CNTFR may be prepared from bacterial cells that express recombinant CNTFR as follows. The gene encoding human CNTFR may be subcloned into a bacterial expression vector, such as for example, but not by way of limitation, pCP110. The resulting plasmid, pRPN151, encodes a recombinant, mature form of human CNTFR (huCNTFR), consisting of 327 amino acids of the mature huCNTFR coding region and three additional amino acids, Met Ser Thr, at the NH$_2$ terminus. Additional manipulations at the beginning of the coding region, as described in Example Section 6, further optimize huCNTFR expression without modifying the protein sequence. This recombinant plasmid may then be transformed into a suitable strain of bacteria, such as E. coli strain RFJ26 and grown under culture conditions known in the art to induce synthesis of recombinant protein, so as to obtain useful amounts of recombinant huCNTFR.

The recombinant huCNTFR may be purified by any technique which allows for the subsequent formation of a stable, biologically active CNTF/receptor complex. For example, and not by way of limitation, huCNTFR may be recovered from RFJ26/pRPN151 cells as inclusion bodies, followed by quantitative extraction in 8M guanadinium chloride and dialysis as in Section 7, infra. In order to further purify CNTFR, it may be undesirable to use methods such as conventional ion exchange chromatography, hydrophobic interaction chromatography, or reverse phase chromatography as active CNTFR may be difficult to isolate following these procedures. Rather, the present invention provides for a method of further purifying CNTFR comprising gel filtration. According to the present invention, proteins other than CNTFR that are expressed at low levels (e.g. <2%) may also be purified by this method.

The CNTF/receptor complex may be formed subsequent to the purification of CNTF and CNTFR. Any ratios of CNTF and CNTFR which produce a stable CNTF/receptor complex may be used, including but not limited to, 1:1, 2:1, 3:1, etc. For example, but not by way of limitation, equimolar amounts (e.g., 80 nM) of recombinant CNTF and recombinant CNTFR may be mixed in a physiological buffer solution (e.g., 100 mM Tris HCl, 50 mM NaCl, pH 8.0) at room temperature. The mixture may then be applied to a gel filtration column and the peak corresponding to the CNTF/receptor complex may be recovered for use in numerous assays described infra.

The present invention provides for complexes in which CNTF and CNTFR are covalently or, preferably, non-covalently linked.

The present invention further relates to any complex or molecule which may be used to either promote or, alternatively to antagonize cell differentiation. In particular embodiments of the invention, the CNTF/receptor complex imparting such an effect may be encoded by a hybrid or chimeric nucleic acid sequence. This hybrid or chimeric nucleic acid sequence may be constructed by any of the numerous recombinant DNA methods known in the art such that sequences encoding functional portions of both CNTF and CNTFR are translationally linked; subcloned into either a prokaryotic or eukaryotic expression plasmid such that expression of the hybrid or chimeric nucleic acid sequence is controlled by any of a number of promoter elements compatible with the prokaryotic or eukaryotic host system as well as the orientation of the hybrid gene within the expression plasmid. In a preferred embodiment of the invention, the nucleic acid sequences encoding functional portions of CNTF and CNTFR are subcloned in the same orientation and under control of the same regulatory sequences, resulting in a "dicistronic" construction. The nucleic acid region spanning the fusion junction of the CNTF and CNTFR gene will either possess a sequence promoting splicing of the initial transcript prior to translation or, alternatively, this region will encode a peptide sequence known in the art to promote post-translational proteolytic processing by a protease active in the host cell. The construction of such a hybrid or chimeric molecule promotes the expression of equimolar amounts of both functional components of the CNTF/receptor complex and allows for purification of the CNTF/receptor complex directly from either the prokaryotic or eukaryotic host cell. The present invention also relates to nucleic acid sequences that encode a mutant CNTFR. A given CNTFR gene can be mutated in vitro or in vivo, to create site-specific changes, additions or deletions in the coding region. Any technique for mutagenesis known in the art can be used, including but not limited to, in vitro site directed mutagenesis [Hutchinson, et al., J. Biol. Chem. 253:6651 (1978)], use of TAB linkers (Pharmacia), etc. In various nonlimiting embodiments of the invention, hybrid or mutant molecules or complexes prepared as above may possess a number of characteristics that differ from those of the native CNTF/receptor complex. For example, such a hybrid or mutant may be able to promote signal transduction in the absence of CNTF (i.e., without the formation of the CNTF/receptor complex).

As another example, a hybrid or mutant may be capable of binding CNTF without resulting in signal transduction. These CNTFR blocking mutants or hybrids may then be assayed for their ability to act as antagonists of signal transduction in the presence of CNTF in any of the assay systems described infra. In preferred embodiments, such CNTFR blocking mutants or hybrids may bind CNTF with a higher affinity than that of native CNTFR for CNTF. In yet another embodiment of the invention, a CNTF mutant may be produced that binds to the CNTFR such that the resulting complex is incapable of signal transduction.

5.2. CHARACTERISTICS OF THE CNTF/ RECEPTOR COMPLEX

The present invention relates to a stable CNTF/receptor complex. In a particular embodiment of the invention as described in Section 5.1 and Example Section 6, a biologically active CNTF/receptor complex is formed by adding equimolar amounts of CNTF and CNTFR in a physiological buffer solution at room temperature. The CNTF/receptor complex of this particular embodiment possesses a different mobility in native polyacrylamide gels than either purified fractions of CNTF or CNTFR.

The CNTF/receptor complex may also be characterized according to its biological activity. In CNTF responsive cells, the activity of the CNTF/receptor complex corresponds to that of CNTF.

CNTF promotes cell differentiation as well as the survival of primary neurons. Target cells for CNTF that express CNTFR, include, but are not limited to, cells of the ciliary ganglion, dorsal root ganglion, hippocampus, and motor neurons.

The biological response of CNTF in these target cells is imparted through CNTF/receptor complex participation in a signal transduction pathway (see, for example, Section 9, infra). For example, CNTF mediates growth arrest and differentiation of MAH cell lines. Exposure of a MAH cell line to CNTF rapidly induces a pattern of tyrosine phosphorylation of three distinct CLIP proteins. In addition, phosphorylation of these CLIP genes immediately precedes induction of a characteristic immediate early gene, tis11. These early phosphorylation events in response to CNTF are indicative of the presence of such a signal transduction pathway.

However, in another embodiment of the invention, the CNTF/receptor complex mediates similar effects as described supra on target cells which do not express the CNTF receptor (see, for example, Section 8, infra), provided such cells express a second component referred to herein as a "signal transducing component;" i.e., a second component that interacts with receptor molecules to induce signal transduction, e.g., gp130 associated with the IL 6 receptor system or the beta chain of the receptor for Leukemia Inhibitory Factor (LIF). Cells which express these signal transducing components are said herein to be CNTF/receptor complex responsive. A target cell for the CNTF/receptor complex may be any cell conducive to identification through a signal transduction assay in vitro (e.g., as discussed supra, such as a target cell which demonstrates a phenotypic differentiation, the expression of immediate early genes or the phosphorylation of CLIP proteins) in response to treatment with the CNTF/receptor complex, or a hybrid or mutant thereof that either mimics or alters the normal physiological effect of the CNTF/receptor complex.

The effect of CNTF/receptor complex, or a related hybrid or mutant compound, on target cells can be assayed by any of a number of phenotypic and/or biochemical responses which are characteristic of the specific cell type. If the target cells are responsive to CNTF, the activity of the complex may be measured as a function of CNTF-related biological effects, such as the survival of ciliary ganglion neurons, dorsal root ganglion neurons, or motor neurons, etc.

If the target cells are not responsive to CNTF, but are CNTF/receptor complex responsive, they may be assayed for other markers of differentiation. For example, but not by way of limitation, an M1 cell line may be utilized to test the ability of the CNTF/receptor complex, or a hybrid or mutant protein thereof, to promote differentiation in a manner similar to the IL-6 or LIF-receptor pathway. Undifferentiated M1 cells are round and phase bright arid do not adhere to the substrate. Upon differentiation, as promoted through the CNTF/IL-6/LIF receptor family, the M1 cells become more differentiated and adhere to the substrate. Therefore, M1 cultures may easily be scored for this differentiation phenotype.

Cell specific markers may also be utilized, as was described supra for MAH cells, such as an alteration in patterns of CLIP or JAK proteins or other patterns of phosphorylation and the activation of immediate early genes (e.g., tis 11; See Section 9, infra).

The ability of the CNTF/receptor complex to promote phenotypic differentiation in M1 cells (e.g., belonging to the IL-6/LIF receptor family) indicates that any other target cell responding to this complex is a target cell for the CNTF/ receptor. In addition to myeloid leukemia cells such the M1 cell line, other potential target cells for the CNTF/receptor, or hybrids and mutants thereof include leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

A target cell for the CNTF/receptor complex may be any cell conducive to identification through a signal transduction assay in vitro (e.g., as discussed supra, such as a target cell which demonstrates a phenotypic differentiation, the expression of immediate early genes or the phosphorylation of CLIP or JAK proteins) in response to treatment with the CNTF/receptor complex, or a hybrid or mutant thereof that either mimics or alters the normal physiological effect of the CNTF/receptor complex.

5.2.1. DIRECT $^{125}$I-hCNTF BINDING ASSAY

As discussed supra, another embodiment of the invention relates to the isolation of CNTFR mutants that are altered in their binding capacity for CNTF. In a preferred embodiment of the invention, mutagenesis of pCMX-hCNTFR(I2) (assigned accession number NRRL B-18789) is followed by a direct $^{125}$I-hCNTF binding assay as described in U.S. patent application Ser. No. 07/700,677, entitled "The Ciliary Neurotrophic Factor," filed May 15, 1991 by Davis et al., now abandoned. Briefly, 10 μg hCNTF (560 μg/ml in 10 mM NaPO$_4$, pH 7.4) may be iodinated with 1 mCi $^{125}$INa using lactoperoxidase 6 ng/μl (Sigma) for 15 minutes at 20° C. After 15 minutes the reaction may be quenched with an equal volume of buffer containing 0.1M NaI, 0.1% BSA and 0.1% cytochrome C, 0.3% HOAc, 0.05% phenol red and 0.02% $NaN_3$. Aliquots may be removed for determination of TCA precipitatable counts. The remainder may be loaded onto a BioRad PD—10 Biogel column equilibrated with 0.05M $NaPO_4$, 0.1M NaCl, 0.5 mg/ml protamine sulfate and 1 mg/ml BSA. Fractions may be collected and TCA precipitable counts determined. Next, COS cells may be transfected with mutagenized plasmid DNA. After 48 hours, the media may be removed and replaced with 0.25 ml of binding buffer (RPM1 1640 with 10% FBS and 0.1% $NaN_3$) containing $^{125}$I-hCNTF alone or with unlabelled hCNTF. Incubations with $^{125}$I-hCNTF may be for 60 minutes at room temperature. After incubations are complete, the $^{125}$I-hCNTF solution is removed and the cells washed three times with 1.0 ml of binding buffer and then lysed with 0.25 ml of 0.1N NaOH. This lysate may be transferred to a 12×75 mm polystyrene tube and placed in a gamma counter. Non-specific binding may be determined by the addition of at least 100 fold excess unlabelled hCNTF. After the last wash the plates may be autoradiographed.

CNTFR mutants exhibiting either high or little or no CNTF binding may be selected for further analysis. Supernatants from transfected cell lines of interest may be utilized in any number of differentiation assays to determine the ability of each mutant to promote signal transduction.

5.2.2. SIGNAL TRANSDUCTION ASSAY

As discussed supra, the M1 cell assay system is useful for measuring the signal transducing ability of members of the CNTF/IL-6/LIF receptor family.

This assay system is also useful to practice further embodiments of the invention, namely to identify mutant CNTF receptors that transduce signals without binding CNTF, and mutant CNTF receptors that bind CNTF but do not induce signal transduction. For example, if a CNTFR mutant gives a weak or non existent signal in the $^{125}$I-hCNTF direct binding assay, then this mutant receptor is scored in the M1 assay for the ability to promote phenotypic differentiation. Conversely, a CNTFR mutant showing increased binding may also be assayed in the M1 system. The mutant CNTF receptor may be mixed with varying amounts of unlabeled CNTF and scored in the M1 assay for the ability to inhibit phenotypic differentiation (e.g, the mutant CNTFR acts as an antagonist to signal transduction pathway).

In a further embodiment of the invention, different target cells of the CNTF/IL-6/LIF family may be identified using the same type of assay as described for M1 cells.

Alternatively, target cells may be identified in an assay system that demonstrates signal transduction, such as phosphorylation of CLIP or JAK proteins or immediate early gene induction, as described in Section 9, infra. For example, a culture of putative target cells may be exposed to an effective concentration of CNTF/receptor complex and then evaluated for phosphorylation of CLIP or JAK proteins, induction of tis11 immediate early gene expression, etc., in which such evidence of signal transduction indicates that the cells are indeed targets for CNTF/receptor complex.

5.3. UTILITY OF THE CNTF/RECEPTOR COMPLEX

According to the present invention, the CNTF/receptor complex, or a hybrid or mutant thereof, may be used to promote differentiation, proliferation or survival in vitro or in vivo of cells that are responsive to the CNTF/receptor complex including cells that express receptors of the CNTF/IL-6/LIF receptor family, or any cells that express the appropriate signal transducing component as evidenced by the characteristics (e.g., phosphorylation of CLIP or JAK proteins and/or immediate early gene induction) set forth in section 5.2, supra. Mutants or hybrids may alternatively antagonize cell differentiation or survival.

5.3.1. IN VITRO APPLICATIONS

The present invention may be utilized to identify new target cells for potential therapeutic or diagnostic applications of the CNTF/receptor complex. For example, but not by way of limitation, assays identifying changes in morphology (e.g. progression from rounded to flat cells and the extension of cellular processes and the transition from free-floating to attached cells) or biochemical markers (e.g., the expression of cell specific markers, the activation of cellular genes, such as the immediate early gene, tis 11, or the alteration in phosphorylation patterns, such as the CLIP or JAK proteins) or cell growth or proliferation may be utilized to identify such novel target cells.

Conversely, cells responsive to the CNTF/receptor complex may be used to identify CNTF/receptor complex related hybrid or mutant compounds. For example, such cells may be exposed to varying concentrations of CNTF/receptor complex related hybrid or mutant compound, and then the presence or absence and magnitude of physiological effects, such as cell proliferation, cellular morphology, phosphorylation of CLIP or JAK proteins, immediate early gene induction, etc. may be determined. If the hybrid or mutant acts as an agonist of CNTF/receptor complex action, physiological changes should be similar to those produced by CNTF/receptor complex. Alternatively, if the hybrid or mutant acts as an antagonist of CNTF/receptor complex action, the physiological changes associated with CNTF/receptor complex action should be diminished or eliminate ed.

Any such target cell identified as a cell responsive to the CNTF/receptor complex through alterations of morphological or biochemical patterns is a candidate for use in diagnostic assays. Such assays involve testing cells biopsied from patients for sensitivity to a particular treatment protocol involving the CNTF/receptor complex, or a hybrid or mutant thereof which promotes or antagonizes the signal transduction within this family of receptors.

The present invention may be utilized to diagnose diseases and disorders of the nervous system which may be associated with alterations in the pattern of CNTF or CNTFR expression, and hence, formation of the CNTF/receptor complex. For example, an abnormal response to CNTF/receptor complex in cells taken from a patient may support a diagnosis of a neurological disorder in the patient.

Such cell biopsies can be used to detect, prognose, diagnose, or monitor conditions, disorders, or disease states associated with changes in CNTF expression, including in particular, conditions resulting in damage and degeneration of neurons known to respond to CNTF, such as parasympathetic neurons, cholinergic neurons, spinal cord neurons, neuroblastoma cells and cells of the adrenal medulla. such diseases and conditions include but are not limited to central nervous system trauma, infarction, infection, degenerative nerve disease, malignancy, or post-operative changes including but not limited to Alzheimer's Disease, Parkinson's Disease, Huntington's Chorea, and amyotrophic lateral sclerosis.

In a further embodiment, the present invention has utility regarding any target cell identified through a bioassay system as described supra. Any such target cell is a candidate for use in an in vitro system to detect, prognose, diagnose, or monitor the condition of the differentiation disorder or disease including, but not limited to malignant or neoplastic conditions, and in particular diseases or disorders involving the following cells: leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

5.3.2. IN VIVO APPLICATIONS

The present invention may be used to treat disorders of any cell responsive to the CNTF/receptor complex, including cells that are responsive to CNTF, as well as cells that are not. In preferred embodiments of the invention, disorders of cells that express members of the CNTF/IL-6/LIF family may be treated according to these methods. Examples of such disorders include but are not limited to those involving the following cells: leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

Accordingly, the present invention provides for methods in which a patient suffering from a CNTF-related neurological or differentiation disorder or disease is treated with an effective amount of the CNTF/receptor complex, or a hybrid or mutant thereof. The CNTF/receptor complex or appropriate hybrids or mutants thereof, may be utilized to treat disorders or diseases as described for CNTF in International Application PCT/US90/05241 published as WO91/104316 on Apr. 4, 1991 by Sendtner, et al. and for CNTFR in U.S. patent application Ser. No. 07/700,677, entitled "The Ciliary Neurological Receptor," filed May 15, 1991 by Davis et al., now abandoned. Therapeutic methods comprising administering the CNTF/receptor complex, a CNTFR mutant inducing signal transduction without binding CNTF or a CNTF/receptor complex antagonist (e.g., a CNTFR mutant with a high CNTF binding affinity that does not induce signal transduction), are within the scope of the invention.

The present invention also provides for pharmaceutical compositions comprising the CNTF/receptor complex, hybrid or mutant thereof in a suitable pharmacologic carrier.

The CNTF/receptor complex, hybrid or mutant thereof may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

5.3.2.1. FORMATION OF THE ACTIVE INGREDIENT

The active ingredient, which may comprise the stable CNTF/receptor complex, or a hybrid or mutant thereof, should be formulated in a suitable pharmaceutical carrier for administration in vivo by any appropriate route including, but not limited to injection (e.g., intravenous, intraperitoneal, intramuscular, subcutaneous, endoneural, perineural, intraspinal, intraventricular, intrathecal etc.), by absorption through epithelial or mucocutaneous linings (e.g., oral mucosa, rectal and intestinal mucosa, etc.); or by a sustained release implant, including a cellular or tissue implant.

Depending upon the mode of administration, the active ingredient may be formulated in a liquid carrier such as saline, incorporated into liposomes, microcapsules, polymer or wax-based and controlled release preparations, or formulated into tablet, pill or capsule forms.

The concentration of the active ingredient used in the formulation will depend upon the effective dose required and the mode of administration used. The dose used should be sufficient to achieve circulating plasma concentrations of active ingredient that are efficacious. For example, when CNTF/receptor complex is the active ingredient, a circulating serum concentration level ranging from about 50 picomolar to 100 nanomolar may be used. Effective doses may be extrapolated from dose-response curves derived from in vitro or animal model test systems.

In an alternative embodiment CNTF/receptor complex preparations are provided, in which more than one CNTF/receptor complex are linked together either directly or through another member, such as a bead.

5.4 CNTF, IL-6 AND LIF SHARE SIGNAL TRANSDUCING COMPONENTS

Signal transduction pathways activated by both CNTF and LIF in the MAH cell line, as well as in other neuronal cell lines, were compared to those activated by LIF and IL-6 in hemopoietic cell lines. In U.S. patent application Ser. No. 676,847 filed Mar. 28, 1991, which is incorporated by reference herein, we described the possible interaction between CNTF, the CNTF receptor and the signal transducer gp130. The studies described herein confirmed the finding that the CNTF signalling pathway involves gp130 and further revealed that LIF also utilizes a signalling pathway that involves the IL-6 signal transducer, gp130. Also described herein is the discovery that CNTF and LIF share a second gp130-like receptor component. This suggests that CNTFR (CNTFRA) is all that is required to change the LIF receptor complex into a functional CNTF-responsive receptor complex.

In the case of IL-6, a complex between IL-6 and its receptor component binds gp130, which then somehow activates the signal transduction process [Taga et al., Cell 58:573–581 (1989); Hibi et al., Cell 63:1149–1157 (1990)]. The ability of gp130 to transduce functional signals correlates with its ability to be phosphorylated on tyrosine [Murakami et al., Proc. Natl. Acad. Sci. U.S.A. 88:11349–11353 (1991)]. Here we have identified cell lines that allow for comparison of responses to CNTF and LIF, distant relatives of IL-6. Strikingly, the CNTF responsive neuronal cell lines examined displayed indistinguishable phenotypic and biochemical responses to LIF; in contrast, LIF responsive hemopoietic cells did not respond to CNTF. CNTF and LIF responses in neuronal cells appear to initiate with the tyrosine phosphorylation of the three CLIPs, at least two of which (CLIP1 and CLIP2) are cell surface proteins that can interact to form a stable, immunoprecipitable complex.

The CLIP phosphorylations precede and, based on kinase inhibitor studies, are apparently required for subsequent characteristic gene inductions. LIF and CNTF display parallel dose responses, time courses and inhibitor profiles with respect to these phosphorylations and gene inductions, and prior treatment with either factor will down-regulate responses to the other. Not only are the CNTF and LIF induced signalling events essentially indistinguishable in neuronal cells, but they appear identical to those induced by LIF in hemopoietic cells. These events are also very similar to those induced by IL-6 in hemopoietic cells, except that CLIP1 phosphorylation is specifically characteristic of CNTF and LIF responses. We provide a basis for the similarities in the CNTF, LIF and IL-6 signalling pathways by presenting evidence that one of the CLIPs (CLIP2) is the IL-6 signal transducer gp130.

Our findings raise many questions concerning the interactions of the various CNTF and LIF receptor components with gp130/CLIP2. CNTF can bind directly to the IL6R-related CNTFR [Davis et al., Science 253:59–63 (1991)] that, based on our data and by analogy to the IL-6 system (FIG. 21A), then presumably interacts with gp130. However, the CNTF receptor complex apparently also includes another cell surface protein, CLIP1, that is tyrosine phosphorylated in response to CNTF and can directly interact with gp130 (FIG. 21A). LIF is known to bind a recently cloned gp130-related receptor component with a molecular weight of approximately 190 kD (hereon LIFR), and the existence of a LIF-receptor β (hereon LIFR) has also been proposed [Gearing et al, Cell 66:9–10 (1991)]. Our data indicates that the LIF receptor complex also includes CLIP1 and gp130 (FIG. 21A). Finally, the receptor complex for IL-6/CNTF/LIF-related G-CSF is apparently a homodimer of the gp130-related G-CSF receptor [Fukunaga et al, EMBO J. 10:2855–2865 (1991)] (FIG. 21A).

Although the receptor complexes portrayed in FIG. 21A mediate binding to structurally related ligands, as depicted they are unsatisfyingly different. It is possible to propose more "uniform" receptor models, however, if one considers the possibility that CLIP1, which is similar in size to LIFRβ, is indeed LIFRβ (FIG. 21B). Thus, the CNTF and LIF receptor complexes would each utilize two different gp130-like components, LIFRβ/CLIP1 as well as gp130 itself. These two β components would directly interact based on our co-precipitation data, and they would both be inducibly phosphorylated on tyrosine. Supporting such a receptor structure, recent crosslinking data [Godard et al., J. Biol. Chem. 267, (in press)] reveal that LIF can be bound to two distinct proteins with sizes that would correspond to those of LIFRβ/CLIP1 and gp130. The involvement of two β components in the LIF and CNTF receptor complexes would be reminiscent of the G-CSF receptor structure (FIG. 21B) ad raises the possibility that the IL-6 receptor complex may also involve a homodimer of gp130. In fact, it may be that β-subunit dimerization and/or activation leads to activation of the signalling process, as proposed for receptor tyrosine kinases and some cytokine receptors [Aaronson et al., Science 254:1146–1153 (1991); De Vos et al., Science 255:306–312 (1992)].

In the model presented in FIG. 21B, the β receptor components would act to modulate the binding of the factors to the β components, and thus be responsible for conferring ligand specificity upon the shared transducing machinery. Cross-linking data [Godard et al., J. Biol. Chem. 267 (in press)] might suggest that for LIF, as with G-CSF, such components may not be required. Thus, the CNTFR component would be all that is required to convert a functional LIF receptor into a functional CNTF receptor. The latter possibility, together with the restricted expression of CNTFR to the nervous system, adrenal gland, sciatic nerve and skeletal muscle [Davis et al., Science 253:59–63 (1991)], could explain why all CNTF-responsive neuronal cells also respond identically to LIF [see above; also Rao et al., Dev. Biol. 139:65–74 (1990)], whereas LIF responsive cells outside of the nervous system do not respond to CNTF.

Interestingly, the components for IL-6 or CNTF do not have to be membrane bound in order to interact with their transducing components [Taga et al., Cell 58:573–581 (1989)]. Thus, complexes containing these factors together with soluble forms of their receptors may act as heterodimeric factors for cells that are not capable of responding to the factor alone (because they do not express the appropriate receptor), but which do express the appropriate transducing components. The possibility that such heterodimeric complexes actually operate as soluble factors in vivo is supported by the homology between the receptor components and one of the two subunits of natural killer cell stimulatory factor, a normally occurring heterodimeric factor [Gearing and Cosman, Cell 66:9–10 (1991)]. Furthermore, the unusual and readily cleavable glycosylphosphatidylinositol linkage of the CNTFR to the cell surface points toward a role for regulated release of this receptor component [Davis et al., Science 253:59–63 (1991)].

While the receptor models presented above need further experimental verification, they clearly have relevant precedents. A plethora of G-protein coupled receptors similarly interact with a small number of signal transducing heterotrimeric G-proteins, allowing a vast array of different signals (eg. neurotransmitters, polypeptide hormones and odorants) to converge on a relatively modest number of signalling pathways [Gilman, Ann. Rev. Biochem. 56:615–647 (1987)]. More directly relevant to the gp130-coupled receptor systems are those of IL-3, IL-5 and GM-CSF. The overlapping activities and similar tyrosine phosphorylations induced by IL-3, IL-5 and GM-CSF led to the finding that these factors use distinct receptor components but share components (reviewed in Nicola and Metcalf, Cell 67:1–4 (1991); Miyajima et al. Annu. Rev. Immunol. 10:295–331 (1992). Once again, the receptor components are primarily involved in binding the factors, but lack extensive cytoplasmic domains and thus do not appear to have signal transducing capabilities. The shared subunits appear to be required for high affinity binding, and are responsible for initiating signal transduction events that involve tyrosine phosphorylations. As with gp130 (and presumably LIFR/CLIP1), the subunits are themselves tyrosine phosphorylated, but do not appear to have inherent kinase activity. Although little is known about the mechanisms by which these subunits are tyrosine phosphorylated, the multicomponent IL2 receptor also utilizes a subunit (IL2R) that is responsible for high affinity binding and signal transduction, and this chain is tyrosine phosphorylated by a src-like tyrosine kinase (lck) with which it physically associates (reviewed in Miyajima et al., in press). Interestingly, CLIP phosphorylation and IL-2 induced lck phosphorylation display similar susceptibility profiles to kinase inhibitors [Hatakeyama et al., Science 252:1523–1528 (1991)]. That is, both phosphorylations are susceptible to staurosporine but not to H-7, suggesting that similar tyrosine kinases may be involved; CLIP3 may be a candidate for such a src-related kinase.

In several important ways, CNTF appears to be quite unusual compared to its distant cytokine relatives. Most importantly, CNTF has a very restricted receptor component distribution and, thus far, it is primarily cells of the nervous system that appear responsive to CNTF [Davis et al., Science 253:59–63 (1991)]. This restriction contrasts with the broad actions the cytokines related to CNTF; the CNTF example suggests that additional related cytokines displaying a very restricted range of actions may exist. Identification of the MAH cell line provides a neuronal precursor cell line which displays physiologically relevant responses to CNTF and LIF as well as to factors using unrelated receptor systems, such as FGF and NGF. Use of the MAH cell line should contribute to the understanding of how different factors, utilizing distinct signalling pathways, can interact to effect the growth and differentiation of neuronal progenitor cells. Contrasting the responses of MAH cells and hemopoietic cell lines to the cytokines should also provide insight into the mechanisms by which distinct cellular contexts alter the perception and interpretation of a very similar initial signal.

5.5 USES OF COMMON AND UNIQUE RECEPTOR COMPONENTS

As described herein, CNTF and LIF share components of a receptor complex/signal transduction pathway. Accordingly, CNTF alone, or in combination with CNTFR (CNTFα), may prove to be useful as a means of initiating a response in a cell normally responsive to LIF. Depending on the receptor components a cell has, it may respond to CNTF or to a combination of CNTF and CNTFR. If a cell has gp130, LIFRβ and CNTFα (as appears to be the case with ES cells), CNTF alone will have the same effect at LIF. If the cell has only gp130 and LIFRβ, CNTF and CNTFR in combination would mimic the effect of LIF.

5.5.1 USE OF CNTF TO PREVENT THE DIFFERENTIATION OF EMBRYONIC STEM CELLS

We have recently determined that CNTF can be utilized in place of LIF to prevent the differentiation of ES cell. Embryonic stem (ES) cells, totipotent cells isolated from pre-implantation-stage mouse embryos, can be cultured and manipulated in vitro and then reincorporated into a host embryo where they can develop normally and contribute to all cell lineages including the germ line. ES cells, thereby, provide an ideal vector system for the introduction of a specific mutation into mice.

Maintenance of the totipotent ES cells in culture requires either the presence of a feeder layer of fibroblasts (eg., STO cells) or the soluble factor leukemic inhibitory factor (LIF) Smith, et al. Nature 336, 688–690 (1988); Williams, et al. Nature 3365, 684–687 (1988). The use of feeder cells is very reliable, but the preparation of the feeder layers is time-consuming. STO cells must be treated for 2–3 hrs. with mitomycin C to arrest their growth, then after several washes with PBS the STO cells can be plated onto gelatin-coated plates. The plates can be used the following day, but are only good for 1 week after plating (Robertson, Nature 323, 445–448 (1987). To circumvent the problem of feeder layers, Williams et al., Nature (1988) supra and Pease and Williams, Exp. Cell Res. 190, 209–211., (1990) found that ES cells maintained in the absence of feeder cells retained their potential to form germ-line chimeras, provided LIF was included in the culture media.

ES cells cultured in the presence of CNTF, but in the absence of feeder cells and LIF, will retain the characteristic stem-cell morphology of compact colonies of small cells. This is the first example of a factor other than LIF which will prevent the differentiation of ES cells. The existence of two factors which elicit a similar response, provide further opportunity to study the regulatory mechanisms by which ES cells are diverted from differentiation.

5.5.2 ACTIVATION OF LIF RESPONSIVE CELLS USING CNTF/CNTFR

As described herein, the combination of CNTF and CNTFR or soluble CNTFR (sCNTFR) should bind to and activate any cell that responds to LIF. LIF responsive cells are, however, fairly ubiquitous, thus the use of CNTF and its soluble receptor to activate such cells would not be expected to provide any foreseeable advantages as far as enhanced specificity. In addition, the efficiency of the soluble receptor/CNTF complex appears to be much lower than if the CNTFR is attached to the cell surface by the GPI anchor.

To increase both the specificity of the CNTF/CNTFR complex as well as its efficiency, the present invention contemplates the targeting of cells by complexing the CNTFR to the surface of a target cell and subsequently using CNTF to activate such a cell. In an alternative embodiment, the CNTF/CNTFR complex is modified in such a way as to make it specific for a particular target cell.

Methods of targeting proteins, such as CNTFR, to cell surfaces are known to those skilled in the art. In general, such proteins are attached to cell surfaces using a linking molecule, a molecule that is capable of binding to both the CNTFR as well as the target cell. Preferably, such a linking molecule would allow flexible binding to a naturally occurring receptor on a target cell. For example, attachment of a linking molecule with a terminal galactose to CNTFR would allow for attachment of such a complex to asialoglycoprotein receptors in the liver. Another example might include attachment of an Fc containing linking molecule to CNTFR that would allow attachment of CNTFR to target cells containing Fc receptors.

Alternatively, antibodies, preferably monoclonal antibodies, would be effective as linking molecules. For example, antibodies that recognize a particular cell surface receptor could be linked to the CNTFR. Alternatively, an epitope could be attached to CNTFR, wherein such an epitope is recognized by a linking antibody that binds both the CTNFR-epitope complex and an epitope on a target cell. If an antibody directed against a target cell binds to an unknown epitope, it could be identified by panning random peptide expression libraries [see, for example PNAS 89:1865 (1992)].

If CNTFR is attached to the surface of a target cell, the cell can then be activated by the addition of CNTF. Alternatively, CNTFR attached to a linking molecule (a molecule capable of attaching it to the surface of a target cell) can be combined with CNTF. In such a case, the active agent would be the CNTF/CNTFR/linking molecule complex.

5.5.3 IDENTIFICATION OF CNTFR ANTAGONISTS

Based on the identification herein of signal transduction pathways shared by IL-6, LIF and CNTF, it would follow that the identification of a soluble CNTFR analog that would bind to CNTF, and interact with LIFRβ and gp130 to form a complex, but not be capable of transducing a signal, would also function as an effective inhibitor of activation by LIF or IL-6. Mutants of CNTF may also display these activities.

In a specific embodiment, HepG2 cells, which respond to LIF and IL6 in the "acute phase response" involving the transcriptional upregulation of a variety of genes including fibrinogen are used to provide an assay system for CNTF agonists or antagonists. It has been demonstrated that reporter constructs consisting of ChAT and the responsive gene's upstream sequences (i.e. the fibrinogen promoter) will accurately report functional signalling by IL-6 by upregulating ChAT activity. A reported construct linked to a secreted or cell surface enzyme (such as alkaline phosphatase) could be used to screen mutants of CNTF-sCNTFR for the ability to block LIF or IL6 activation of the reporter. The mutants could be transfected into the HepG-2 cells and screened in 96 well plates.

Alternatively, HepG-2 cells transfected with CNTFR would provide a valuable assay system for screening for CNTF activators and/or inhibitors.

5.5.4 ASSAY SYSTEMS

The present invention provides for assay systems and methods that may be used to detect and/or measure CNTF activity or to identify agents that act as agonists or antagonists of CNTF or other cytokine members of the CNTF receptor family. This activity may be construed to be the biological activity of CNTF or the related cytokine, or of other, heretofore unidentified factors which utilize receptor components or signal transduction pathways in common with the CNTF receptor family. The biological activities of CNTF have been described in International Application No. PCT/U.S. 90/05241, filed Sep. 14, 1990 by Sendtner et al; of IL-6 in Kishimoto, et al. Science 258:593 (1992); of OSM in Rose and Bruce, Proc. Natl. Acad. Sci. U.S.A., 88:8641–8645 (1991); Grove, et al. J. Biol. Chem. 266:18194–18199 (1991); Liu, et al., J. Biol. Chem. 267:16763–16766 (1992) and of LIF in Chang and Gough, Focus 14:6–9 (1991); Escary, et al. Nature 363:361–363 (1993). Henceforth, both CNTF receptor family members and agents which act as agonists or antagonists of such activity will be referred to as test agents.

Accordingly, the present invention provides for methods of detecting or measuring the activity of a test agent. Each such method involves, at a minimum, a cell that expresses the β-component(s) of the receptor as well as a signal transduction component selected from the group consisting of Jak1, Jak2 and Tyk2 or any other signal transduction component, such as the CLIPs, that are determined to be phosphorylated in response to a member of the CNTF receptor family.

A cell that expressed the β-receptor component(s) and signal transduction component(s) described herein may either do so naturally or be genetically engineered to do so. For example, Jak1-encoding nucleic acid sequences obtained as described in section 12.1, infra, may be introduced into a cell by transduction, transfection, microinjection, electroporation, via a transgenic animal, etc., using any known method known in the art. See for example, the transfection of COS cells as described in section 12.1.2, infra.

According to the invention, the cells are exposed to a test agent and the tyrosine phosphorylation of either the β-component(s) or the signal transduction component(s) are compared to the tyrosine phosphorylation of the same component(s) in the absence of the test agent.

In another embodiment of the invention, the tyrosine phosphorylation that results from contacting the above cells with the test agent is compared to the tyrosine phosphorylation of the same cells exposed to the CNTF receptor family member. In such assays, the cell must either express the extracellular receptor (α-component) or the cells may be exposed to the test agent in the presence of the soluble receptor component. Thus, for example, in an assay system designed to identify agonists or antagonists of CNTF, the cell may express the α-component CNTFRα, the β-components gp130 and LIFRβ and a signal transducing component such as Jak1. The cell is exposed to test agents, and the tyrosine phosphorylation of either the β-components or the signal transducing component is compared to the phosphorylation pattern produced in the presence of CNTF. Alternatively, the tyrosine phosphorylation which results from exposure to a test agent is compared to the phosphorylation which occurs in the absence of the test agent. Alternatively, an assay system, for example, for IL-6 may involve exposing a cell that expresses the β-component gp130 and a signal transducing protein such as Jak1, Jak2 or Tyk2 to a test agent in conjunction with the soluble IL-6 receptor 9 (see section 12.2.4, infra.).

In another embodiment of the invention, no α-receptor components are present. Such assay systems are useful to identify small molecules that are capable of initiating or blocking signal transduction absent binding to a cell surface receptor component.

In another embodiment of the invention, cells expressing the β-component of a specific receptor and one or more signal transducing components, may exhibit tyrosine phosphorylation of the β-component in the absence of any transduction inducing ligand. Such cells are useful to determine the ability of a test agent to inhibit this step in the signal transduction pathway by contacting the cells with test agents and measuring the effect of the test agents on the tyrosine phosphorylation.

6. EXAMPLE: PRODUCTION OF HUMAN CNTF RECEPTOR IN E. COLI

1. Material and Methods

1. Construction of pCP110

The parental plasmid expression vector, pCP110, is described in Masiakowski, et al., J. Neurochem. 57:1003–1012 (1991).

2. Construction of a Vector For Expression of huCNTFR 1

Plasmid pRPN151 was generated by replacing the DNA between the unique SalI and EagI restriction sites in pCP110 with a PCR fragment copied from plasmid pCMX-hCNTFR (I2) with the use of the DNA primers shown in FIG. 3. Human CNTFR consists of the 327 amino acids of the mature huCNTFR sequence and three additional amino acids of the sequence Met-Ser-Thr at the $NH_2$-terminus. The three additional amino acids were included in order to signal translation initiation at the desired amino acid position and in order to simplify subsequent genetic engineering manipulations. At the same time, the DNA sequence was further modified at the beginning of the coding region in order to optimize expression without modification of the protein sequence. This was accomplished by incorporating the desired changes into the sense PCR primer (FIG. 3). Plasmid pRPN151 was then transfected into the E. coli strain, RFJ26. Under appropriate induction conditions of RFJ26/pRPN151 cells, huCNTFR reached levels representing 10–20% of total protein.

3. Purification of hucntfr

The majority of the receptor synthesized in RFJ26/pRPN151 cells was localized in inclusion bodies from which it was quantitatively extracted in 8M guanidinium chloride and recovered in soluble form by dialysis, as described for recombinant rat and human CNTF (International Application No. PCT/U.S. 90/05241, filed Sep. 14, 1990 by Sendtner et al.). The recovery of active, correctly folded receptor was accomplished by gel filtration such that correctly folded Cntfr molecules would elute at their true size, away from the aggregated protein in the void volume.

6.2. RESULTS

Analysis by absorbance at 280 nm and electrophoresis on reducing SDS-PAGE gels of the proteins eluting from such a column revealed that even though most of the receptor eluted in the void volume (30–40% pure) apparently in aggregate form, some receptor eluted in a distinct, sharp peak (80–90% pure), at the proper molecular weight position (40 kD). The receptor in the latter peak represented 10–50% of the receptor in the starting material, depending on the refolding conditions (FIGS. 5A and 5B).

Analysis of the elution profile on native gels showed that the receptor protein in the void peak did not enter the gel, as would be expected for aggregated protein, whereas receptor in the 40 kD peak migrated as a sharp band, as would be expected for a population of molecules having a common conformation.

7. EXAMPLE: FORMATION OF THE CNTF/RECEPTOR COMPLEX

The 40 kD peak recovered as described in Section 6.1.3. was utilized in a mixing experiment with purified rat CNTF.

7.1. MATERIALS AND METHODS

A constant amount of receptor with increasing amounts of rat CNTF were mixed and the samples run on a pH 7.4 native gel system as described by Goldenberg [Analysis of Protein Conformation by Gel Electrophoresis, in: "Protein Structure", ed: Creighton; IRL Press, Oxford (1989)].

Additionally, purified receptor and rat CNTF were mixed in a physiological buffer solution (100 mM Tris-HCl, 50 mM NaCl, pH 8.0) at room temperature and loaded on a Superdex-75 column (Pharmacia). An absorbance peak corresponding to the receptor-CNTF complex was recovered and stored at 5° C. for 48 hours, at which time a portion of the sample was again subjected to gel filtration as described supra.

7.2. RESULTS

When receptor from the void peak was mixed with rat CNTF and analyzed on native gels, the receptor remained in the well, along with some of the CNTF. In contrast, when receptor from the 40 kD peak was mixed with rat CNTF, the two proteins migrated as a single band in a new position of the gel (FIG. 6). The shift in gel mobility appears complete at approximately equimolar concentrations of CNTF and CNTF receptor. These results indicate that hucntfr associates tightly with CNTF.

At that time, analysis of a portion of the sample on the same gel filtration column described above indicates that all the protein eluting in a major absorbance peak corresponds to the receptor-CNTF complex, with no evidence of peaks corresponding to the individual protein components. As a control, a second portion of the sample was analyzed by reverse phase chromatography using a C8 cartridge (Applied Biosystems) in 0.1% trifluoroacetic acid-acetonitrile. As expected, and previously observed with other receptors [Cunningham, et al., Science, 254, 821–825 (1991)] in this strong acid-organic solvent mixture the receptor-CNTF complex dissociates to its two individual components, confirming its composition.

These results indicated that under the conditions of these experiments, i.e., at a receptor and CNTF concentration of 80 nM and nearly physiological ionic strength, pH and temperature conditions, recombinant CNTF receptor forms a stable complex with CNTF.

8. EXAMPLE: THE CNTF/RECEPTOR COMPLEX PROMOTES DIFFERENTIATION OF MYELOID LEUKEMIA CELLS

8.1. MATERIALS AND METHODS

8.1.1. CELL CULTURE CONDITIONS

M1 cells, a myeloid leukemia-derived cell line, were cultured in Dulbecco's Modified Eagle's Medium and 10% horse serum. They were seeded at a density of 50,000 cells per well in NUNC 24 well plates. Cytokines and/or CNTF receptor were added to each well and cultures were scored for differentiated phenotype 5 days later. Soluble CNTF receptor was produced in $E.\ coli$ and purified to homogeneity.

8.1.2 SCORING BY PHENOTYPE

Undifferentiated M1 cells are round and phase bright and do not adhere to the substrate. These are scored (−). As the cells become more differentiated, they adhere to the substrate, become less phase bright, assume irregular to spindle shaped morphology, and extend processes. Cultures are scored (+) to (++++) depending on the extent to which they have these features. Under optimal conditions, IL-6 treatment gives a score of (++) and LIF gives a score of (+++). Extremely high concentrations of CNTF and CNTFR gives the strongest expression of these characteristics and were scored (++++).

8.2. RESULTS

At concentrations of 20 ng/ml, maximal responses of the cells was observed to IL-6 (++) and to LIF (+++). Table 1 shows the response of M1 cells treated with varying combinations of rat CNTF and soluble human receptor. Table 2 shows the response of the cells to varying combinations of human CNTF with human receptor. Clearly, the combination of CNTF with its receptor is much more effective than either one alone in eliciting a response. The receptor alone did not cause differentiation at any concentration tested, although at very high concentrations, CNTF alone did seem to cause a response. Finally, for some experiments the native receptor was produced in COS cells and cleaved from the cell surface by treatment with phospholipase C. In these experiments, the concentrations of soluble receptor was not determined. The combination of this receptor with 200 ng/ml rat CNTF also caused differentiation, whereas neither CNTF nor CNTFR alone had this effect.

TABLE 1

| human CNTFR (ng/ml) | rat CNTF (ng/ml) | | | |
|---|---|---|---|---|
| | 0 | 20 | 100 | 500 |
| 0 | − | − | − | +/− |
| 40 | − | + | + | + |
| 200 | − | + | ++ | +++ |
| 1000 | − | ++ | +++ | +++ |

TABLE 2

| human CNTFR (ng/ml) | human CNTF (ng/ml) | | | | | | | |
|---|---|---|---|---|---|---|---|---|
| | 0 | 20 | 100 | 500 | 1000 | 5000 | 10000 | 25000 |
| 0 | − | − | − | − | +/− | + | + | ++ |
| 40 | − | − | − | +/− | ND | ND | ND | ND |
| 200 | − | − | +/− | + | ND | ND | ND | ND |
| 1000 | − | − | + | ++ | +++ | +++ | +++ | ++++ |

9. EXAMPLE: CNTF RESEMBLES LIF IN MEDIATING PHOSPHORYLATION OF CLIP PROTEINS AND EXPRESSION OF IMMEDIATE EARLY GENES

9.1. MATERIALS AND METHODS

9.1.1. REAGENTS

Preparation and purification of recombinant rat CNTF used in this study have been previously described

[Masiakowski et. al., J. Neurochem. 57:1003–1012 (1991)]. Murine IL-6 (mIL-6) was purchased from UBI (Upstate Biotech., Inc. NY), while recombinant human LIF was from Amgen Biologicals (Calif.). bFGF purified from bovine brain was purchased from R&D Systems, while NGF was purified from mouse submaxillary gland. Protein Kinase inhibitors used include H-7 [1-(5-Isoquinolinesulfonyl)-2-methylpiperaine dihydrochloride, Seikagaku Kogyo Co.) and staurosporine (Kamiya Biomed. Co.). Antiphosphotyrosine monoclonal antibodies conjugated to agarose beads was from Upstate Biotech., Inc. (NY).

9.1.2. CELL STRUCTURE

MAH cells were maintained in culture as previously described [Birren et. al., Neuron 4:189–201 (1990)]. Briefly, cells were plated onto dishes precoated with poly-D-lysine (100 ug/ml) and laminin (10 ug/ml), at a density of 6 K/6 mm well, or 40 K/16 mm well. Medium used was modified L15-$CO_2$ medium supplemented with 10% FBS and dexamethasone (5 uM). IARC-EW-1 (Ewing sarcoma cells) and SK-N-LO (neuroepithelioma cells) was cultured in RPMI medium with 10% fetal bovine serum supplemented with 2 mM L-glutamine and 100 units/ml penicillin and streptomycin. PC12 cells were cultured in Dulbecco's modified Eagle's medium supplemented with 6% horse serum, 6% calf serum, 2 mM L-glutamine and 100 units/ml penicillin and streptomycin.

9.1.3. MTT ASSAY, $^3$H-THYMIDINE INCORPORATION ASSAY AND ChAT ASSAY

MAH cells were treated with factors for various periods of time, prior to the addition of MTT dye (final concentration of 0.5 mg/ml). Incubation was continued for 8 hrs, and DMSO was added to solubilize the dye product taken up by vital cells. The optical density at 570–650 nm was quantitated using the Flow Titretek multiscan apparatus. For $^3$H-thymidine incorporation assay, cells were treated with various factors for different periods of time, and $^3$H-thymidine (NEN-NET-027E) was added at a final concentration of 1 uCi/ml and incubated for 4 hrs at 37° C. Cells were then washed three times with PBS, lysed with NaOH (0.5N) for 2 hrs at room temperature and 3H-DNA was counted. ChAT were performed using standard techniques. Briefly, cells were treated with various factors, washed with ice cold PBS, ChAT harvest buffer containing 20 mM Tris-HCl (pH 8.6) and 0.1% Triton X-100 was added and incubated for 15 min. on ice. Cell extracts were then incubated for 60 min. at 37° C. with a reaction mixture containing 11 mM choline chloride, 0.2 mM 14C-acetyl CoA, 0.14 mM physostigmine, 300 mM NaCl. 50 mM $Na_2PO_4$, 20 mM EDTA. An aliquot of this mixture was mixed with scintillation fluid containing acetonitrile/teraphenylboron (5 mg/ml), and counted.

9.1.4. RNA ISOLATION AND ANALYSIS

Cells were plated at a density of $5 \times 10^6$ cells on 100 mm dishes, and treated with factors for various periods of time. Total RNA was prepared by guanidinium thiocyanate method as described previously [Chomczynski et al., Anal. Biochem. 162:156–159 (1987)]. Ten ug RNA was electrophoresed on a formaldehyde agarose gel, transferred to a nylon membrane (MSI), and hybridized to 32p-probes labelled by random oligo-priming (Stratagene). The probes used included tis11 (2.3 kb EcoR1 fragment), c-fos (1 kb Pst fragment), rat CNTF receptor (rCNTFR, 0.4 kb Pst fragment), and GAPDH (1.25 kb Pst fragment).

9.1.5. PROTEIN ISOLATION, IMMUNOPRECIPITATION AND IMMUNOBLOTTING

For the detection of protein tyrosine phosphorylation, approximately $1–2 \times 10^6$ cells were starved for 60 min. in serum-free, defined medium, treated with various factors for 5 min., and protein lysates prepared with RIPA buffer (supplemented with proteinase and phosphatase inhibitors) as previously described [Glass et al., Cell 66:405–413 (1991)]. To prepare total protein samples, protein loading dye was added directly to the RIPA lysate supernatants and boiled for 3 min. at 90° C. Alternatively, supernatants from the RIPA lysates were precipitated overnight at 4° C. with 100 ul of agarose conjugated anti-phosphotyrosine antibodies (4G10), washed 3x with the RIPA buffer. Proteins were eluted from the agarose beads wit 200 ul of 1x protein loading dye and boiled for 3 min. Fifty microliter of either the total protein samples or the immunoprecipitate was electrophoresed on 10% SDS-polyacrylamide gels, immunoblotted with anti-phosphotyrosine antibodies as previously described [Glass et al., Cell 66:405–413] and specific proteins detected with 125I-labeled goat anti-mouse polyclonal antibody (1 ul of 4.91 uCi/ug per 1 ml buffer, DuPont). For the immunoprecipitation of ERK proteins in PC12 cells, the cell lysate was immunoprecipitated with an ERK-specific antibody (Zymed, Inc.), followed by a Goat anti-mouse IgG antibody conjugated to agarose. The precipitate was electrophoresed as above and immunoblotted with the same ERK antibody.

9.1.6 CELL SURFACE BIOTINYLATION ASSAY

Following a 5 minute incubation with LIF or CNTF to induce CLIP phosphorylation, cells were washed in 5 ml PBS supplemented with 1 mM orthovanadate (PBSV), then incubated for 10 minutes on ice in PBSV containing 1 mg/ml NHS-SS-biotin (3-sulfosuccinimido 3-[2-(biotinamido)ethyl]dithio]propionate; Pierce), a membrane-impermeant reagent. The plates of cells were then washed with tris-buffered saline containing orthovanadate and lysed with RIPA buffer as described above. Lysates were precipitated with immobilized anti-phosphotyrosine antibody as described, then bound phosphoproteins were removed from the beads by boiling for 5 minutes in 50 mM tris pH 8.2 containing 1% SDS. Biotinylated proteins were precipitated from this solution by incubation for 1 hour with 20 L streptavidin-agarose (Pierce). The supernatant containing the non-biotinylated proteins was subjected to SDS PAGE after the addition of sample buffer. The beads containing biotinylated proteins were washed once in the binding buffer, then the bound biotinylated proteins were eluted from the beads by boiling for 5 minutes in 2x SDS PAGE sample buffer containing 10% β-mercaptoethanol. Anti-phosphotyrosine immunoblotting on these samples was performed as described above.

9.2. RESULTS

9.2.1. CNTF AND LIF MEDIATE GROWTH ARREST AND DIFFERENTIATION OF MAH CELLS

The MAH cell line utilized in this example was derived by immortalizing sympathoadrenal progenitors with the v-myc oncogene [Birren et al., Neuron 4:189–201 (1990)]. Treatment of MAH cells with CNTF dramatically blocked the increase in cell number that normally occurs upon the culture of these cells. LIF, which has effects on mature sympathetic neurons similar to those of CNTF, also blocked the normally occurring increase in MAH cell number of cells in CNTF- or LIF-treated cultures remained essentially constant over a 4 day period, while the control cultures continued to accumulate at an exponential rate (FIG. 7B). The effects of both CNTF and LIF displayed a very similar dose-dependency, with $EC_{50}$ values of approximately 50 pg/ml (or 2 pM) (FIG. 7C); this dose-dependency is similar to that observed for the survival effect of CNTF on ciliary neurons [Masiakowski et al., J. Neurochem 57:1003–1012 (1991)]. Unlike either CNTF or LIF, basic fibroblast growth factor (FGF) acted as a potent mitogenic agent for these cells (FIG. 7C, inset), as shown previously [Birren et al., Neuron 4:189–201 (1990)].

Neither CNTF nor LIF induced neurite extension, or other morphological changes characteristic of neuronal differentiation, in MAH cells. However, cell cycle analysis showed that CNTF-treated MAH cells were arrested in the G1 phase of the cell cycle reminiscent of many factors that induce a transition between a proliferative state and cell differentiation. CNTF has been shown to induce cholinergic differentiation of sympathetic progenitors, and both CNTF and LIF induce cholinergic differentiation of mature sympathetic neurons. In order to pursue the possibility that CNTF and LIF may have a differentiative effect on MAH cells, we assayed for the induction of choline acetyltransferase (ChAT) activity in response to these ligands. As shown in FIG. 8A, treatment of MAH cells with CNTF or LIF resulted in an approximate 2-fold increase in ChAT activity while bFGF had no effect. Furthermore, exposure of MAH cells to CNTF for 24 hours led to an increase of low-affinity NGF receptor mRNA upon stimulation of PC12 cell differentiation by NGF.

Together, the above data suggests that CNTF acts as a growth arrest/differentiative factor for sympathoadrenal progenitor cells. These actions appear quite distinct from those of FGF. In addition to acting as a mitogenic agent for MAH cells, FGF induces neurite outgrowth and initiates neuronal differentiation (but not cholinergic differentiation) of these cells; FGF-induced differentiation may yield an NGF-dependent cell. Thus multiple factors may normally be capable of effecting the differentiation of neuronal progenitors. MAH cells appear to be a very useful model system in which to dissect the roles of various factors in mediating various aspects of neuronal differentiation.

9.2.2. CNTF AND LIF RAPIDLY INDUCE INDISTINGUISHABLE PATTERNS OF TYROSINE PHOSPHORYLATION OF CELLULAR PROTEINS

Although cytokines do not utilize receptors which contain intrinsic tyrosine kinase activity, tyrosine phosphorylation is rapidly induced by a variety of different cytokines. To determine whether CNTF induces tyrosine phosphorylation in responsive cells, and to compare these phosphorylations with those induced by its distant structural relatives, we first examined CNTF and LIF responses in MAH cells as well as in neuroepitheliomas and Ewing's sarcoma. As shown in FIGS. 9A–9C, both CNTF and LIF rapidly induced tyrosine phosphorylation of three proteins (designated as $p200^{CLIP1}$, $p160^{CLIP2}$, and $p75^{CLIP3}$ for CNTF- and LIF-inducible phosphoproteins) in MAH cells, Ewing's sarcoma (EW-1), and neuroepithelioma (SK-N-LO). The induced phosphorylation patterns were indistinguishable for either factor in the different lines examined. Thus, CNTF-receptor positive cell lines with different phenotypic responses to CNTF (i.e., with respect to cell growth) displayed indistinguishable phosphorylation patterns in response to CNTF. The observed tyrosine phosphorylation responses were dose-dependent, with maximal induction obtained at 10 ng/ml for both CNTF and LIF.

To determine whether CLIP phosphorylations were specifically characteristic of CNTF and LIF responses, we compared CNTF and LIF phosphorylation patterns with those of FGF and NGF. Although both MAH and EW-1 cells are responsive to FGF, the CLIPs are not phosphorylated in response to FGF in either line (FIGS. 9A–9C). Similarly, the CLIPs are not phosphorylated in response to NGF in the NGF-responsive pheochromocytoma cell line, PC12 (FIG. 10C).

A family of serine/threonine protein kinases designated as extracellular signal-regulated kinases, or ERKs, have recently been identified, characterized and molecularly cloned [Boulton et al., Cell 65:663–675 (1991)]. Activation of the ERKs, also known as MAP or MBP kinases, requires tyrosine phosphorylation [Boulton et al., Cell 65:663–675 (1991)] and rapidly occurs following the binding of receptor tyrosine kinases to their cognate ligands (e.g., for NGF, see FIG. 10C). The ERKs are also activated in response to a diverse set of both mitogenic and differentiative agents that do not utilize receptor tyrosine kinases. We chose to examine ERK phosphorylation in response to CNTF, LIF and FGF in EW-1 cells. In contrast to FGF, CNTF or LIF did not induce the rapid tyrosine phosphorylation of a 40 kD protein (FIG. 10A) that could be identified as ERK2 (FIG. 10B).

Our findings demonstrate that induction of $p200^{CLIP1}$, $p160^{CLIP2}$, and $p75^{CLIP3}$ tyrosine phosphorylation is characteristic of, and relatively specific for, the signal transduction pathways activated by CNTF and LIF. A protein similar in size to $p160^{CLIP2}$ is phosphorylated on tyrosine in response to both IL-6 and LIF [Nakajima and Wall, Mol. Cell. Biol. 11:1409–1418 (1991); Lord et al., Mol. Cell. Biol. 11:4371–4379 (1991)]; a possible relationship between these induced proteins will be addressed below. Unlike responses mediated by the CNTF and LIF receptors, responses which activate tyrosine kinase receptors, such as those induced by FGF and NGF, do not result in CLIP phosphorylation. Conversely, stimulation of tyrosine kinase receptors results in rapid activation of the ERKs, which are not rapidly phosphorylated by either CNTF or LIF.

9.2.3. THE RAPID AND TRANSIENT PHOSPHORYLATION OF CLIPS PRECEDES INDUCTION OF A CHARACTERISTIC IMMEDIATE EARLY RESPONSE GENE. TIS11

The induction of a signal transduction cascade initiated by ligand receptor interaction often proceeds with the activation of tyrosine phosphorylation and is then followed by the activation of immediate-early response genes. It has been previously reported that the activation of the immediate-early gene expression by both LIF and IL-6 is preceded by the rapid and transient tyrosine phosphorylation of p160 [Nakajima and Wall, Mol. Cell. Biol. 11:1409–1418 (1991); Lord et al., Mol. Cell. Biol. 11:4371–4379 (1991)]. In FIGS. 11A–11C, we have compared the time course of CNTF- and LIF-induced tyrosine phosphorylation of the CLIPs with the activation of immediate-early gene expression. We specifically examined the expression of one immediate early response gene, tis11, which appears to be characteristic of IL-6 mediated responses, as well as another immediate early response gene, c-fos, which does not appear to be specific for IL-6 responses. The induction of tyrosine phosphorylation of all three CLIPs by both CNTF and LIF in MAH cells was rapid, occurring within 5 minutes and were significantly decreased by 30 minutes (FIGS. 11A–11C). The phosphorylation kinetics for both factors were similar in EW-1 cells.

In MAH cells, CNTF and LIF both produced an induction in tis11 gene expression which followed the induction of CLIP phosphorylation. Maximal activation occurred at 45 minutes and returned to control levels by 120 minutes (FIG. 11B). Similar gene activation kinetics for tis11 were observed in EW-1 cells. No induction of c-fos expression was observed in MAH cells with either CNTF or LIF (FIG. 11B). However, bFGF, unlike CNTF and LIF, induced c-fos gene expression in the absence of tis11 gene induction in MAH cells (FIG. 11C). CNTF and LIF induced both tis11 and c-fos (FIG. 11C) in EW-1 cells.

Our results suggest that rapid phosphorylation of the three CLIPS, followed by the induction of tis11 gene expression, characterizes both CNTF and LIF responses in neuronal cell lines.

Our results suggest that rapid phosphorylation of the three CLIPS, followed by the induction of tis11 gene expression, characterize both CNTF and LIF responses in neuronal cell lines. The timing of these events, together with the involvement of both a 160 kD phosphoprotein (CLIP2) as well as tis11, suggests similarities between the transduction pathway utilized by CNTF and LIF in neuronal cells and the pathway activated by IL-6 and LIF in hemopoietic cells. A direct comparison of the tyrosine phosphorylation events reveals striking similarities and differences. LIF induces the tyrosine phosphorylation of proteins identical in size to CLIP1, CLIP2 and CLIP3 in the M1 myeloid progenitor cell line, whereas IL-6 induces the tyrosine phosphorylation of only two of these proteins, corresponding to CLIP2 (presumably p160) and CLIP3; CNTF does not induce any detectable tyrosine phosphorylation in M1 cells (FIG. 12).

Specific phosphorylation events can be distinguished using different proteins kinase inhibitors. We utilized the protein kinase inhibitors staurosporine and H-7 to provide further evidence that CNTF- and LIF-induced phosphorylations are identical, and to determine whether the kinase cascades leading to tis11 activation are similar for CNTF, LIF and IL-6; H-7 was used because it specifically blocks a downstream kinase required for tis11 gene induction by IL-6 without affecting the initial tyrosine phosphorylation events [Nakajima and Wall, Mol. Cell. Biol. 11:1409–1418 (1991); Lord et al., Mol. Cell. Biol. 11:4371–4379 (1991)]. As shown in FIGS. 13A–13D, both CNTF and LIF-induced tyrosine phosphorylation events were blocked by staurosporine, but not by H-7, in either MAH cells or EW-1 cells. However, H7 similarly blocked the induction of tis11 gene induction by CNTF and LIF in MAH cells (FIG. 13 C) or by IL-6 and LIF in M1 cells (FIG. 13 D); as expected from the phosphorylation data, staurosporine also blocked tis11 gene induction.

Thus a direct comparison of phosphorylation events, together with the use of protein kinase inhibitors, demonstrates that the signalling pathway activated by CNTF and LIF in neuronal cell lines corresponds to that utilized by LIF in hemopoietic cells. Furthermore, this pathway is distinguishable from, but shares many of the novel features of the IL-6 activated pathway in hemopoietic cells.

Thus the tis11 induction appears to be characteristic of responses to several of these distantly related cytokines, and the mechanism of induction by these different cytokines displays a similar sensitivity to protein kinase inhibitors.

The M1 cells did not express CNTF receptors and did not respond to CNTF, while the MAH, Ewing's sarcoma and neuroepithelioma cell lines examined did not respond to IL-6. The finding that cell lines can be found which segregate responsiveness to CNTF, LIF or IL-6 suggests that no two of these factors utilize an identical receptor.

9.2.4 DOWNREGULATION OF CLIP1 AND CLIP2 DUE TO PRETREATMENT WITH CNTF OR LIF CANNOT BE REVERSED BY CNTF OR LIF ADDITION

As would be expected if CNTF and LIF share signal transducing components, down-regulation of CLIP1 and CLIP2 phosphorylation due to pretreatment with CNTF or LIF could not be overcome by subsequent addition of the other factor (FIG. 14A). Furthermore, sub-saturating concentrations of these factors displayed additive effects for MAH cell growth inhibition while saturating concentrations were no longer additive.

9.2.5 EXPRESSION OF CLIPS ON THE CELL SURFACE

To determine whether the CLIPs were expressed on the cell surface, we utilized an assay that specifically results in the biotinylation of cell surface proteins [Stahl et al., Biochemistry 29, 5405–5412 (1990)]. This assay revealed that CLIP1 and CLIP2 did indeed express extracellular domains that could be biotinylated (FIG. 14B); the surface location of CLIP1 was also consistent with the finding that its apparent size decreased upon peptide-N-glycosidase F treatment.

10. EXAMPLE: CHARACTERIZATION OF CLIP

10.1 CLIP2 IS IDENTICAL TO gp130

The possibility that IL-6, CNTF and LIF share gp130 was investigated by using a monoclonal antibody (AM64) specific for human gp130 [Hibi et al., Cell 63:1149–1157 (1990)] in concert with a human cell line responsive to both CNTF and LIF. This antibody does not bind any gp130-related proteins, nor does it bind gp130 from rodent species. Immunoprecipitation of gp130 revealed that it was strongly tyrosine phosphorylated in response to either CNTF or LIF in EW-1 cells, and that this phosphorylated gp130 co-migrated with CLIP2 (compare lanes 3 and 7 with lanes 2 and 6 in FIG. 14C). Furthermore, the anti-gp130 antibody could be used to completely deplete CLIP2 from extracts of CNTF/LIF-induced EW-1 cells (compare lanes 4 and 8 with lanes 2 and 6 in FIG. 14C). From these data we infer that CLIP2 is indeed gp130, and thus that gp130 is tyrosine phosphorylated in response to both CNTF and LIF. Interestingly, CLIP1 partially co-precipitates with gp130 when using the AM64 antibody, suggesting that the two molecules may be found in a complex; less severe lysis conditions (e.g. using digitonin) were able to increase the amount of CLIP1 co-precipitating with gp130 in response to CNTF treatment.

10.2 ANTI-gp130 ANTIBODY SELECTIVELY BLOCKED TYROSINE PHOSPHORYLATION OF CLIPs and tis11 INDUCTION EW-1 cells were starved for 1 hour in defined medium in the presence or absence of a cocktail of anti-gp130 antibodies (2 ug/ml). The cells were treated for 5 minutes or 45 minutes with various factors prior to tyrosine phosphorylation assays and RNA analysis, respectively.

Anti-gp130 antibodies, which have been shown to inhibit IL-6 responses in hepatoma cell lines, were examined for their ability to block tyrosine phosphorylations induced by CNTF and LIF in EW-1 cells. The data demonstrates that tyrosine phosphorylations of CLIP1 and CLIP2 (FIG. 17A) as well as tis11 gene expression (FIG. 17B), induced by CNTF or LIF were both completely blocked by anti-gp130 antibody. On the other hand, tyrosine phosphorylation induced by an unrelated ligand, EGF, was not affected.

10.3 gp130 IS EXPRESSED UBIQUITOUSLY WHEREAS CNTFR EXPRESSION IS MORE LIMITED

It had previously been speculated that gp130 might function as a transducer for factors other than IL-6 based on the finding that gp130 transcripts were much more widely distributed than those for IL-6R [Hibi et al., Cell 63:1149–1157 (1990)]. Consistent with this notion and our finding that gp130 is shared by the CNTF and LIF signalling systems, we find that gp130 transcripts are expressed in both hemopoietic lines responsive to IL-6 (but not CNTF) (FIG. 15, note M1 and B9 cell lines), as well as in adult brain tissue (FIG. 16) and neuronal lines responsive to CNTF and LIF (but not IL-6 ) (FIG. 15, note MAH, EW-1, SK-N-LO and SH-SY5Y cell lines). In contrast, CNTFR mRNA displays a restricted distribution and, in this experiment, is only expressed in the brain and in neuronal lines responsive to CNTF (FIG. 15).

EXAMPLE 11. RESPONSE OF ES CELLS TO CNTF

11.1 ES CELL CULTURE WITH LIF OR CNTF

The 129/Sv//Ev XY ES cell line (gift from Elizabeth Robertson) used in this study was derived from a black, agouti (BB AA) mouse (Robertson et al. Nature 323, 445–448 (1986). Typically, ES cells were grown on a feeder layer of STO cells (growth-arrested with mitomycin C, Sigma Chemical Co.) and maintained in Dulbecco's modified Eagle media (DMEM, Irvine Scientific) supplemented with 10% FBS (Lot #11111020, Hyclone,), 0.1 mM β-mercaptoethanol (Sigma Chemical Co.), 292 mg/ml of L-glutamine, 100 U/ml penicillin G, and 100 mcg/ml streptomycin sulfate (100× stock of L-glutamine, penicillin and streptomycin sulfate, Irvine Scientific). As a precautionary step, LIF (recombinant human LIF, Amgen Biologicals) was added at a concentration of 10 ng/ml to prevent differentiation. ES cells were passaged every 3–4 days onto newly-made feeder cell plates as described previously ((Robertson et al. Nature 323, 445–448 (1986).

To determine the effect of CNTF on ES cells, STO cells and LIF were eliminated from the ES cell culture. ES cells were passaged 2 times, in the presence of LIF (20 ng/ml), onto gelatin-coated plates (0.1% gelatin from porcine skin, Sigma Chemical Co.), few STO cells remained after the second passage. The ES cells were grown for 1 day in the presence of LIF (20 ng/ml), washed free of LIF, and then cultured in the presence of either CNTF, LIF or no factor for 7 days.

11.2 RNA ANALYSIS

Total RNA was prepared from ES cells, grown in the absence of STO feeder cells and maintained in the presence of LIF (20 ng/ml), by the guanidinium thiocyanate method as described (Chomczynski et al., Anal. Biochem. 162, 156–159 (1987). Ten micrograms of RNA was electrophoresed on a formaldehyde agarose gel, transferred to a nylon membrane (MSI), and hybridized to $^{32}$P labelled CNTF receptor cDNA probe (800 bp, Pst1 fragment) labelled by random oligo-priming (Stratagene).

11.3 CNTF BINDING TO ES CELLS

Recombinant rat CNTF was iodinated using the Bolton-Hunter method (Bolton and Hunter, Biochem J. 133:529–539. (1973). ES cells were plated at a density of $2.5 \times 10^6$ cells/35 mm well on gelatin plates and grown in the presence of 20 ng/ml LIF 4 days prior to binding. Media was removed from the wells and the cells were washed once with assay buffer (PBS, pH 7.4, containing BSA (1 mg/ml), 0.1 mM bacitracin, 1 mM PMSF and leupeptin (1 $\mu$g/ml)). The cells were incubated with $^{125}$I-rCNTF (700 pM) for 2 hrs at room temperature, followed by two quick washes with assay buffer. The cells were lysed with PBS containing 1% SDS and monitored for radioactivity.

11.4 RESULTS

11.4.1 ES CELL CULTURE

ES cells maintained in the absence of feeder cells, but in the presence of LIF (10–20 ng/ml) remained as undifferentiated, compact colonies of small cells. However, lower concentrations of LIF (less than 10 ng/ml) resulted in the differentiation of the ES cells over a period of 2–7 days, as evidenced by the presence of endoderm-like cells and large, flat cells. Some cell death also occurred (FIG. 18A). To determine whether CNTF could also sustain ES cells in an undifferentiated state in the absence of feeder cells, ES cells were grown on gelatin plates with varying concentrations of CNTF. Low concentrations of CNTF, 5 pg/ml to 10 ng/ml CNTF, resulted in differentiation and some cell death. However, concentrations of greater than 10 ng/ml up to 50 ng/ml CNTF maintained ES cells as small compact colonies of cells (FIG. 18B). ES cells maintained in the absence of either LIF or CNTF appeared endoderm-like or large and flat over a period of 2–7 days (FIG. 18C).

11.4.2 EXPRESSION OF CNTFR IN ES CELLS

Northern analysis of RNA from ES cells indicated that CNTF receptor mRNA is present, albeit at low levels compared to adult rat brain (FIG. 19).

11.4.3 BINDING OF CNTF TO ES CELLS

ES cells exhibited 85% specific binding of $^{125}$I-rCNTF, with the total bound $cpm_{ave.}=10235+157$ and the non-specific $cpm_{ave.}=1517+163$.

11.4.4 INDUCTION OF tis11 BY CNTF AND LIF IN ES CELLS

ES cells were plated onto gelatin-coated dishes and maintained in undifferentiated state in the presence of either CNTF (20 ng/ml) or LIF (20 ng/ml). The cells were washed twice in defined medium, starved for 2 hours in defined medium prior to the addition of CNTF (50ng/ml) or LIF (50 ng/ml) for 45 minutes. Total cellular RNA was prepared, electrophoresed on a formaldehyde agarose gel, transferred to a nylon membrane (MSI), and hybridized to $^{32}$P-labelled tis11 probe FIGS. 20A 20B. In ES cells, CNTF and LIF both produced similar inductions in tis11 gene expression, indicating responsiveness of ES cells to both of these cytokines.

12. EXAMPLE: THE JAK FAMILY OF KINASES ARE INVOLVED IN SIGNAL TRANSDUCTION BY THE CNTF FAMILY OF FACTORS

12.1. MATERIALS AND METHODS

12.1.1. REAGENTS

Antisera specific for LIFRP (Stahl, et al., J. Biol Chem. 26:8–7631 (1993), gp130 (Davis et al., Science 260:1805–1808 (1993), Jak1 and Jak2 (Silvennoinen et al., Proc. Natl. Acad. Sci. U.S.A., 1993 (in press) have been described. The rabbit antiserum against Tyk2 was raised and purified against a portion of Tyk2 expressed as a glutathione-S-transferase (GST) fusion protein (Velazquez et al., Cell 70:313–322 (1992); S. Pellegrini, unpublished results). Expression plasmids appropriate for COS expression of epitope-tagged LIFRβ and gp130 were previously described (Davis et al., Science 260:1805–1808 (1993), except that the LIFRβ coding sequence was modified to contain 3 successive copies of the myc epitope to improve detectability. Full length cDNA for murine Jak1 and Jak2 were provided in the plasmid pRK5 (J. Ihle et al., unpublished).

12.1.2 METHODS

Cell lines were passaged and maintained as previously described (Ip et al., Cell 69:1121–1132 (1992). COS cell transfections were carried out by a DEAE protocol [Davis et al., Science 260:1805–1808 (1993)]. Plates of cells were starved in serum-free RPMI medium for 2–4 hours, then stimulated with 50 ng/mL of the indicated factor for 5 minutes. Cells were harvested and lysed as previously described [Stahl, et al., J. Biol Chem. 268:7628–7631 (1993)], except that 1% Brij 96 (Sigma) or 1% NP-40 (Boehringer) was used as indicated. Immunoprecipitation, electrophoresis, and anti-phosphotyrosine immunoblotting with monoclonal antibody 4G10 (Upstate Biotechnology) and detection via enhanced chemiluminescence (Amersham) was carried out as previously described (Id). For in vitro kinase assays, the washed beads were incubated for 15 min at room temperature in 20 mM Hepes (pH 7.2), 10 mM MnCl2, 30 mM sodium orthovanadate and 10 mCi of [g-$^{32}$P]ATP (NEN Dupont). Electrophoresis sample buffer was added and the samples were boiled, subjected to SDS PAGE, and electroblotted to PVDF. The membrane was then incubated in 1M NaOH at 65° C. for 60 min to destroy serine and threonine phosphate before autoradiography.

12.2. RESULTS

12.2.1. CNTF-INDUCED RESPONSES ARE ASSOCIATED WITH A 130 kDa PROTEIN

Following addition of CNTF, a receptor complex forms that consists of CNTF, CNTFRα, gp130, and LIFRβ. Immunoprecipitation (IP) of the receptor complex with antibodies against LIFRβ (FIG. 22) or gp130 (not shown) following cell lysis in the detergent Brij 96 results in the copurification of a 130 kDa protein that is tyrosine phosphorylated. LIF and OSM, which also bind to and heterodimerize gp130 and LIFRβ [Gearing et al., Science 255:1434–1437 (1992); Baumann et al., J. Biol. Chem. 268:8414–8417 (1993); Davis et al., Science 260:1805–1808 (1993)], also show association and tyrosine phosphorylation of a protein with an identical appearance (FIG. 22). The purified receptor complex also shows associated protein tyrosine kinase activity in vitro giving rise to tyrosine phosphorylation of both gp130 and LIFRβ, as well as the associated 130 kDa protein. Tyrosine kinase activity is also associated with LIFRβ in the absence of CNTF, although the 130 kDa protein is either not present or not significantly phosphorylated in the absence of the factor. Other experiments showing that this in vitro kinase activity has the same sensitivity to staurosporine as that observed upon addition of CNTF to intact cells suggested that this associated tyrosine kinase activity is relevant to that which is required in the cell to mediate CNTF-induced responses. Furthermore, the 130 kDa protein appears to be a good candidate for this kinase since lysis of the cells in NP-40 does not give copurification of either the 130 kDa protein or tyrosine kinase activity (not shown).

12.2.2. CNTF AND RELATED FACTORS INDUCE TYROSINE PHOSPHORYLATION OF JAK 1, JAK2 and TYK2

Experiments using specific antisera raised against portions of Jak1, Jak2, or Tyk2 reveal that all 3 of these kinases can become tyrosine phosphorylated following stimulation by CNTF, LIF, OSM, and IL6. FIG. 23A shows that CNTF induces tyrosine phosphorylation of both Jak1 and Jak2 in EW1 cells, and these proteins appear to comigrate with 130 and 131 kDa proteins that copurify with the receptor complex immunoprecipitated with a-LIFRβ. Furthermore, the addition of IL6+sIL6Rα (FIG. 23B), as well as LIF and OSM (not shown) to EW-1 cells also results in phosphorylation of Jak1 and Jak2 but not Tyk2. In contrast, IL6 stimulated U266 cells give tyrosine phosphorylation of Tyk2 and Jak1 without apparent change in the phosphorylation status of Jak2. OSM treated SK-MES cells reveal tyrosine phosphorylation of primarily Jak2, with smaller changes in Tyk2 and Jak1. In each of these cases, tyrosine phosphorylation of the Jaks or Tyk2 is associated with an increase in their in vitro tyrosine kinase activity (not shown). These results stand in contrast to previous results showing that stimulation with GM-CSF, EPO, G-CSF, IFN-γ, or IL-3 only result in tyrosine phosphorylation of Jak2 [(Argetsinger et al., Cell 74:237–244 (1993); Silvennoinen et al., Proc. Natl. Acad Sci. U.S.A. (in press;1993); Witthuhn et al., Cell 74:227–236 (1993)]. We conclude from these experiments that the CNTF family of factors can activate Jak1, Jak2, and Tyk2, although there is some variability in which Jak/Tyk family member is activated in a particular cell.

12.2.3. THE JAKS ASSOCIATE WITH CNTF β RECEPTOR COMPONENTS

Transient transfections in COS cells were used to determine whether the Jaks could associate with the β receptor components in the absence of factors. These experiments used carboxy terminally epitope-tagged versions of LIFRβ containing the 10 amino acid portion of c-myc that is recognized by the monoclonal antibody 9E10 [Davis et al., Science 253:59–63 (1991)]. COS cells were cotransfected with appropriate expression vectors encoding full length versions of LIFRβ and Jak1 or Jak2, and Brij 96 lysates were immunoprecipitated with 9E10 and then blotted with the antisera against either Jak1 or Jak2 (FIG. 24). These experiments show that either Jak can associate with LIFRβ in the absence of any added ligand. Furthermore, a truncated version of LIFRβ which retains only the first 76 amino acids of the cytoplasmic domain is fully capable of binding to Jak1 and Jak2 as well. This implicates the membrane proximal region of LIFRβ as the Jak binding domain, which is consistent with the homology between this region of the receptor with those in gp130 and EPOR that have been shown to be required for signal transduction upon factor binding [Murakami et al., Science 260:11349–11353 (1991); Witthuhn et al., Cell 74:227–236 (1993)].

12.2.4 COTRANSFECTION WITH RECEPTOR β-COMPONENTS AND JAKS RESULTS IN LIGAND INDUCED FUNCTIONAL RESPONSE

Further experiments in COS cells were undertaken to establish whether cotransfection of the receptor β-components with the Jaks could reconstruct a ligand-induced functional response. Epitope-tagged gp130FLAG and IL6 were chosen for these experiments, since gp130 homodimerizes and becomes tyrosine phosphorylated in response to IL6+soluble IL6Rα, obviating the need for cotransfection with LIFRβ[Murakami et al., Proc. Natl. Acad. Sci. 88:11349–11353 (1993); Davis et al., Science 260:1805–1808 (1993)]. Following stimulation with IL6+ sIL6Rα, neither mock transfected (lane 1) nor gp130FLAG transfected COS cells (lanes 2–3) revealed substantial tyrosine phosphorylation of gp130 following immunoprecipitation with anti-FLAG and α-PTyr immunoblotting (FIG. 25). In contrast, cotransfection with either Jak1 (lanes 4–5), Jak2 (lanes 6–7), or both Jak1 and Jak2 (lanes 8–9) gives rise to a substantial increase in the induced tyrosine phosphorylation of gp130 upon stimulation with IL6+ sIL6Rα.

12.3 DISCUSSION

Altogether, these results indicate that the Jaks can associate with the CNTF receptor β components, and become tyrosine phosphorylated in response to CNTF, LIF, IL6, or OSM, with concomitant activation of the tyrosine kinase. This most likely occurs through transphosphorylation as ligand-induced hetero- or homo-dimerization of the β components brings their bound Jaks into close apposition [Stahl and Yancopoulos, Cell 74:587–590 (1993)]. The functional reconstruction in COS cells of ligand-induced tyrosine phosphorylation of gp130 upon cotransfection with either Jak1 or Jak2 is consistent with the notion that Jak1, Jak2, or Tyk2 can function as the first kinases activated inside the cell upon receptor β subunit dimerization, thus placing the Jak family of kinases as the most proximal intracellular step in mediating signal transduction of the CNTF family of factors.

REFERENCES

Various publications have been cited herein that are hereby incorporated by reference in their entirety.

---

What is claimed is:

1. A method of measuring the ability of a test agent to act as an agonist of a member of the CNTF receptor family comprising:
(a) providing a cell that co-expresses
(i) gp130, or gp130 and LIFRβ; and
(ii) one or more members of the Jak/Tyk family of kinases;
(b) contacting the cell of step (a) with the test agent;
(c) determining the amount of tyrosine phosphorylation of the member of the Jak/Tyk family in said cell as an indication of the ability of the test agent to act as an agonist of the CNTF receptor family member.

2. A method according to claim 1 wherein the cell of step (a) further coexpresses the α-component of the CNTF receptor family member receptor.

3. A method according to claim 1 wherein the contacting in step (b) is conducted in the presence of the α-component of the CNTF receptor family member receptor.

4. The method according to claim 2 or 3 wherein said α-component is CNTFRα or IL-6Rα.

5. The method according to claim 2 or 3, wherein said CNTF receptor family member is CNTF, wherein the cell in (a) co-expresses in (i) gp130 and LIFRβ, wherein said Jak/Tyk family member is one or more members selected from the group consisting of Jak1, Jak2 and Tyk2 and wherein said α-component is CNTFRα.

6. The method according to claim 2 or 3, wherein said CNTF receptor family member is IL-6, wherein the cell in (a) co-expresses in (i) gp130, wherein said Jak/Tyk family member is one or more members selected from the group consisting of Jak1, Jak2 and Tyk2 and wherein said α-component is IL-6Rα.

7. The method according to claim 1 wherein said CNTF receptor family member is selected from the group consisting of CNTF, LIF, OSM and IL-6.

8. The method according to claim 1 wherein said member of the Jak/Tyk family is selected from the group consisting of Jak1, Jak2 and Tyk2.

9. The method according to claim 1, wherein said CNTF receptor family member is LIF or OSM, wherein the cell in (a) co-expresses in (i) gp130 and LIFRβ, and wherein said Jak/Tyk family member is one or more members selected from the group consisting of Jak1, Jak2 and Tyk2.

10. A method of measuring the ability of a test agent to act as an antagonist of a member of the CNTF receptor family comprising;
(a) providing a cell that co-expresses
(i) gp130, or gp130 and LIFRβ; and
(ii) one or more members of the Jak/Tyk family;
(b) contacting a cell of step (a) with a CNTF receptor family member and determining the amount of tyrosine phosphorylation of said Jak/Tyk family member;
(c) contacting a cell of step (a) with a CNTF receptor family member and the test agent and determining the amount of tyrosine phosphorylation of said Jak/Tyk family member; and
(d) determining the phosphorylation in step (c) as compared to the phosphorylation obtained in step (b) as an indication of the ability of the test agent to act as an antagonist of said CNTF receptor family member.

11. A method according to claim 10 wherein the cell of step (a) further coexpresses the β-component of the CNTF receptor family member receptor.

12. A method according to claim 10 wherein the contacting of steps (b) and (c) are conducted in the presence of α-component of the CNTF receptor family member receptor.

13. The method according to claim 11 or 12 wherein said α-component is CNTFRα or IL-6Rα.

14. The method according to claim 11 or 12, wherein said CNTF receptor family member is CNTF, wherein the cell in (a) co-expresses in (i) gp130 and LIFRβ, wherein said Jak/Tyk family member is one or more members selected from the group consisting of Jak1, Jak2 and Tyk2 and wherein said α-receptor component is CNTFRα.

15. The method according to claim 11 or 12, wherein said CNTF receptor family member is IL-6, wherein the cell in (a) co-expresses in (i) gp130, wherein said Jak/Tyk family member is one or more members selected from the group consisting of Jak1, Jak2 and Tyk2 and wherein said α-receptor component is IL-6Rα.

16. The method according to claim 10 wherein said CNTF receptor family member is selected from the group consisting of CNTF, LIF, OSM and IL-6.

17. The method according to claim 10 wherein said member of the Jak/Tyk family is selected from the group consisting of Jak1, Jak2 and Tyk2.

18. The method according to claim 16, wherein said CNTF receptor family member is LIF or OSM, wherein the cell in (a) co-expresses in (i) gp130 and LIFRβ, and wherein said Jak/Tyk family member is one or more members selected from the group consisting of Jak1, Jak2 and Tyk2.

19. A method of determining whether a test agent is an inhibitor of the binding of a β-component of a CNTF receptor family member to a member of the Jak/Tyk family comprising:
a) measuring the amount of binding of a β-component of the CNTF receptor family member to a member of the Jak/Tyk family in the absence of the test agent;
b) measuring the amount of binding of the β-component of said CNTF receptor family member to the member of the Jak/Tyk family in the presence of the test agent; and
c) identifying as an inhibitor that test agent that reduces the amount of binding of the β-component in step b) as compared to the amount of binding of the β-component in step a).

20. A method according to claim 19 wherein said binding is measured by quantitation of coimmunoprecipitated β component/Jak complexes.

* * * * *